United States Patent
Grotenbreg et al.

(10) Patent No.: US 10,400,024 B2
(45) Date of Patent: Sep. 3, 2019

(54) CLEAVAGE AND EXCHANGE OF MAJOR HISTOCOMPATIBILITY COMPLEX LIGANDS EMPLOYING AZOBENZENE-CONTAINING PEPTIDES

(71) Applicant: SANQUIN REAGENTS B.V., Amsterdam (NL)

(72) Inventors: Gijsbert Marnix Grotenbreg, Singapore (SG); Steven Hendrik Leonard Verhelst, Freising (DE); Ai Ling Joanna Choo, Singapore (SG); Sock Yue Thong, Singapore (SG); Jiawei Yap, Singapore (SG); Wilhelmus Johannes Elisabeth Van Esch, Amsterdam (NL)

(73) Assignee: SANQUIN REAGENTS B.V., Amsterdam (NL)

( * ) Notice: Subject to any disclaimer, the term of this patent is extended or adjusted under 35 U.S.C. 154(b) by 123 days.

(21) Appl. No.: 15/316,824

(22) PCT Filed: Jun. 5, 2015

(86) PCT No.: PCT/NL2015/050407
§ 371 (c)(1),
(2) Date: Dec. 6, 2016

(87) PCT Pub. No.: WO2015/187019
PCT Pub. Date: Dec. 10, 2015

(65) Prior Publication Data
US 2017/0101459 A1    Apr. 13, 2017

(30) Foreign Application Priority Data
Jun. 6, 2014   (EP) .................................. 14171590

(51) Int. Cl.
| | |
|---|---|
| *C07K 5/09* | (2006.01) |
| *C07K 7/06* | (2006.01) |
| *C07K 1/107* | (2006.01) |
| *C07K 14/74* | (2006.01) |
| *C07K 5/065* | (2006.01) |
| *C07K 5/072* | (2006.01) |
| *C07K 5/083* | (2006.01) |
| *G01N 33/68* | (2006.01) |
| *C07C 245/08* | (2006.01) |

(52) U.S. Cl.
CPC ...... *C07K 14/70539* (2013.01); *C07C 245/08* (2013.01); *C07K 1/1075* (2013.01); *C07K 1/1077* (2013.01); *C07K 7/06* (2013.01); *G01N 33/6872* (2013.01); *C07K 5/06078* (2013.01); *C07K 5/06104* (2013.01); *C07K 5/0806* (2013.01); *C07K 5/0815* (2013.01); *G01N 2333/70539* (2013.01)

(58) Field of Classification Search
CPC .................... C07K 14/70539; C07C 245/08
See application file for complete search history.

(56) References Cited

U.S. PATENT DOCUMENTS 5,827,073 A    10/1998 Luescher et al.

FOREIGN PATENT DOCUMENTS

WO     2015187019     12/2015

OTHER PUBLICATIONS

Yilmaz et al. "Resolution of (6)-b-Methylphenylethylamine by a Novel Chiral Stationary Phase for Pirkle-Type Column Chromatography" Chirality, 2010, vol. 22, pp. 252-257.*
Bakker et al., Conditional MHC class I ligands and peptide exchange technology for the human MHC gene products HLA-A1, -A3, -A11, and -B7, PNAS, Mar. 11, 2008, pp. 3825-3830, vol. 105, No. 10.
Leriche et al., Cleavable linkers in chemical biology, Bioorganic & Medicinal Chemistry, 2012, pp. 571-582. vol. 20, Elsevier Ltd.
Toebes et al., Design and use of conditional MHC class I ligands, Nature Medicine, Feb. 2006, pp. 246-251, vol. 12, No. 2, Nature Publishing Group.
Satzger et al., Picosecond dynamics in water-soluble azobenzene-peptides, Chemical Physics Letters, 2004, pp. 191-197, vol. 396.
PCT International Search Report, PCT/NL2015/050407.
PCT Written Opinion of the International Searching Authority, PCT/NL2015/050407.
Boulegue et al., Redox Potential of Azobenzene as an Amino Acid Residue in Peptides, ChemBioChem, 2007, pp. 591-594, vol. 8, Wiley-VCH Verlag GmbH & Co. KGaA, Weinheim, Germany.

* cited by examiner

*Primary Examiner* — Joseph R Kosack
(74) *Attorney, Agent, or Firm* — TraskBritt

(57) ABSTRACT

In one aspect, the disclosure relates to major histocompatibility complex (MHC) molecules comprising a ligand in the peptide binding groove of the MHC molecule, whereby the ligand comprises an azobenzene (Abc), and at least two amino acid residues separated by the azo-group of the Abc, and wherein the amino acid residues are positioned to interact with the peptide binding groove of the MHC molecule. The disclosure also relates, among others, to means and methods for producing and using such MHC molecules, and the ligands therefor.

13 Claims, 28 Drawing Sheets
Specification includes a Sequence Listing.

FIG. 5A (Figure S1)
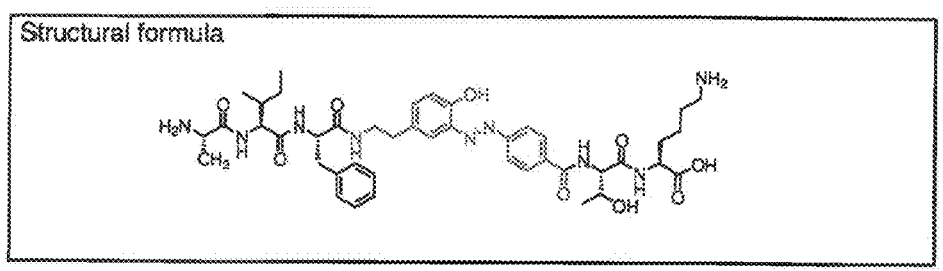
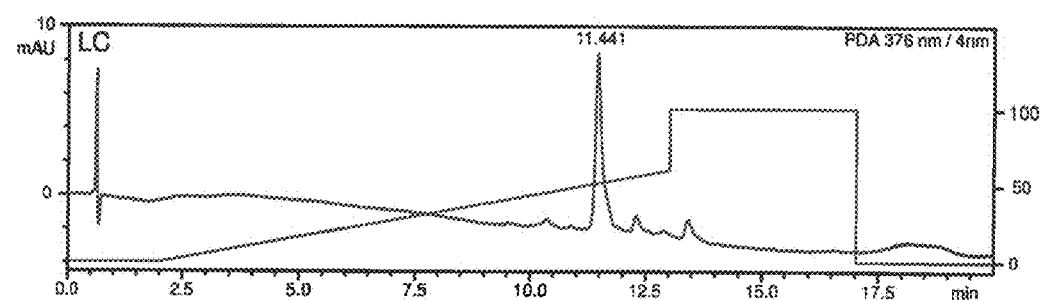
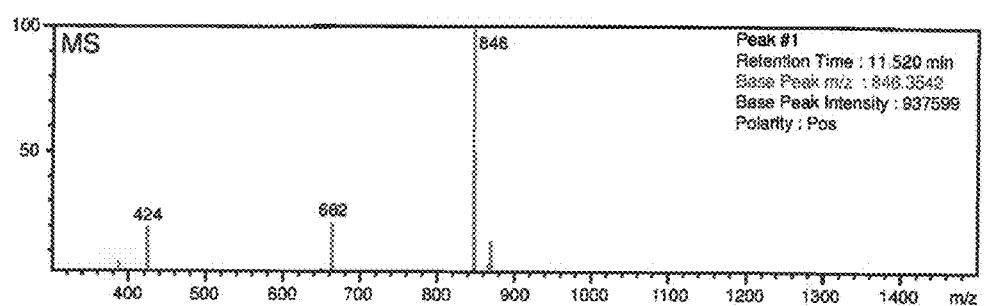

FIG. 5B (Figure S1)
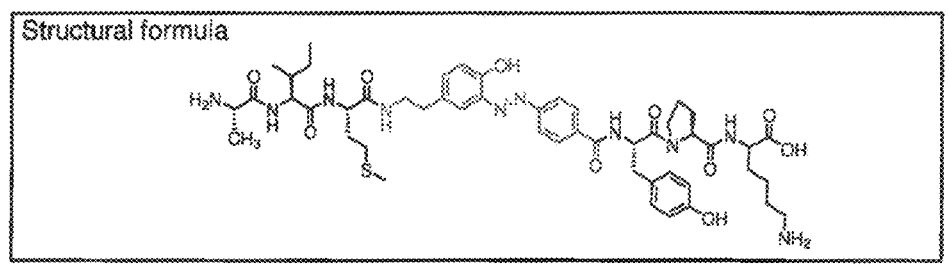
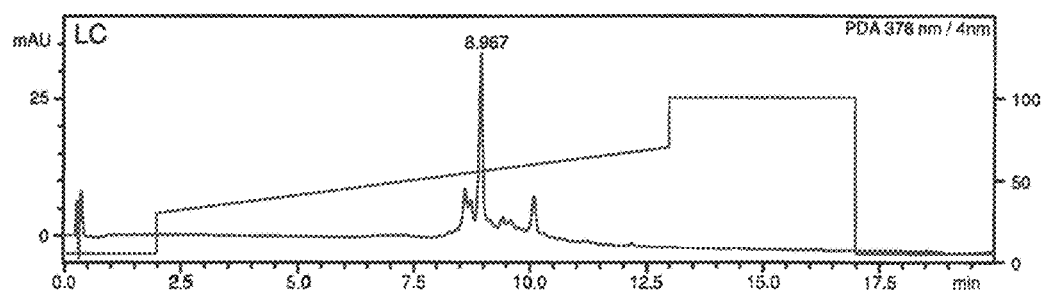
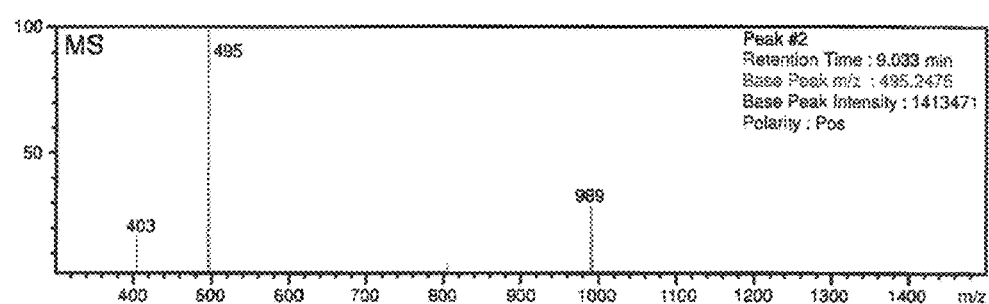

FIG. 5C (Figure S1)
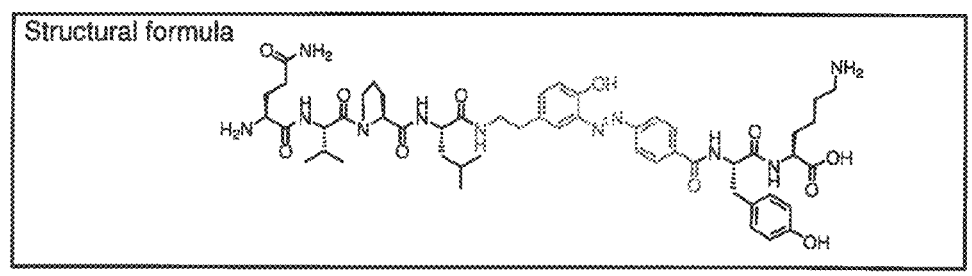
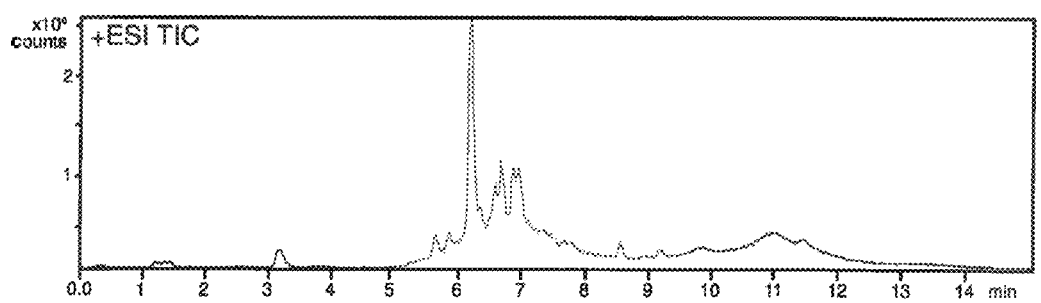
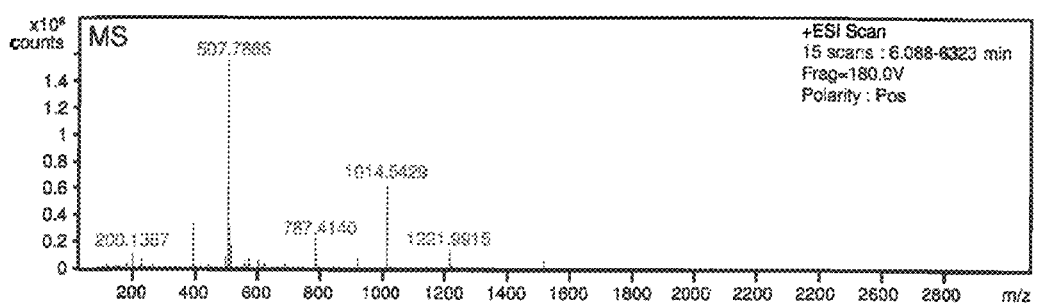

FIG. 5D (Figure S1)
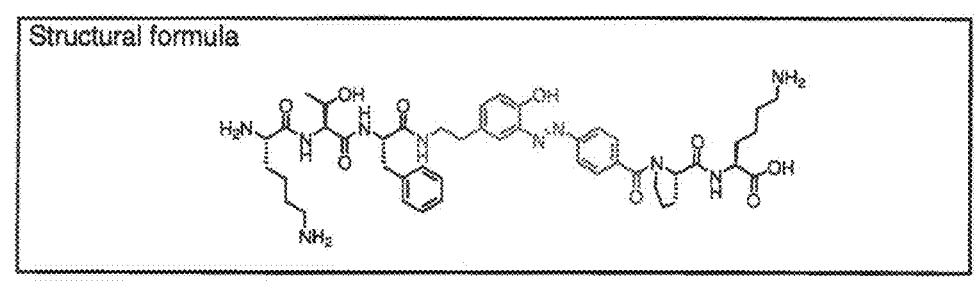
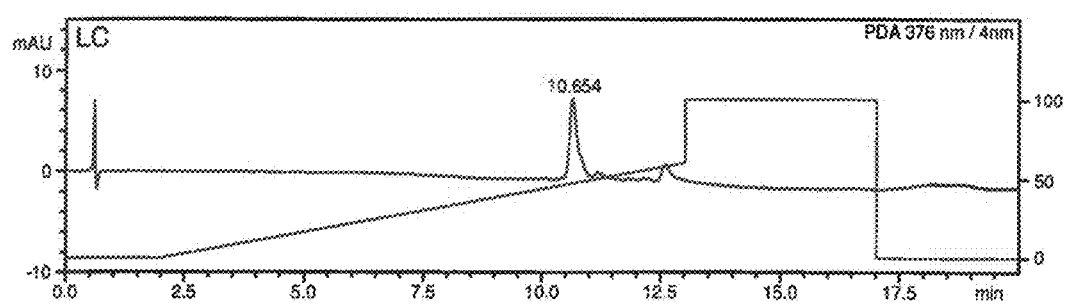
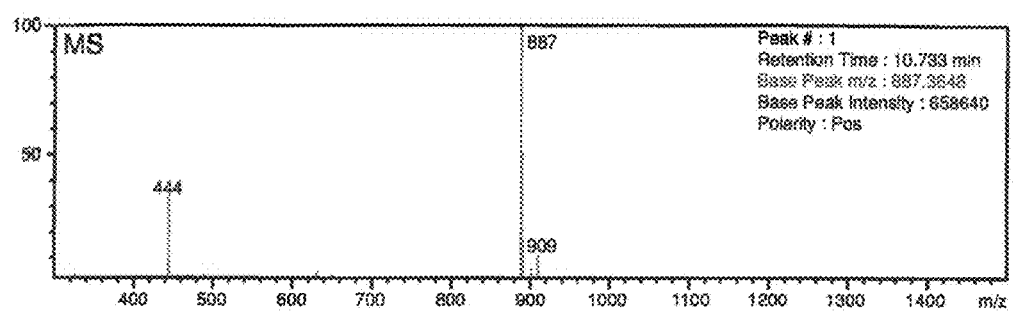

FIG. 5E (Figure S1)
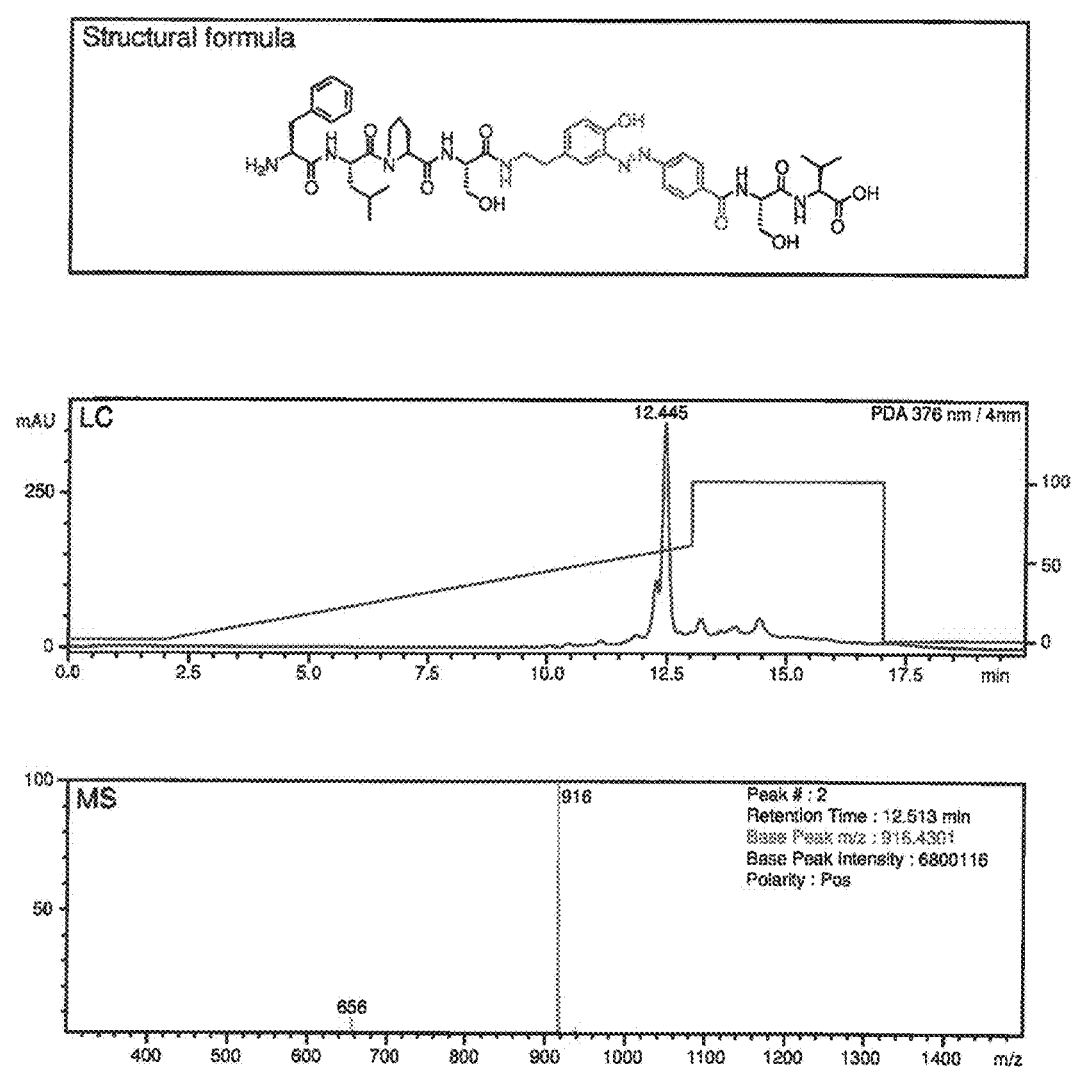

FIG. 5F (Figure S1)
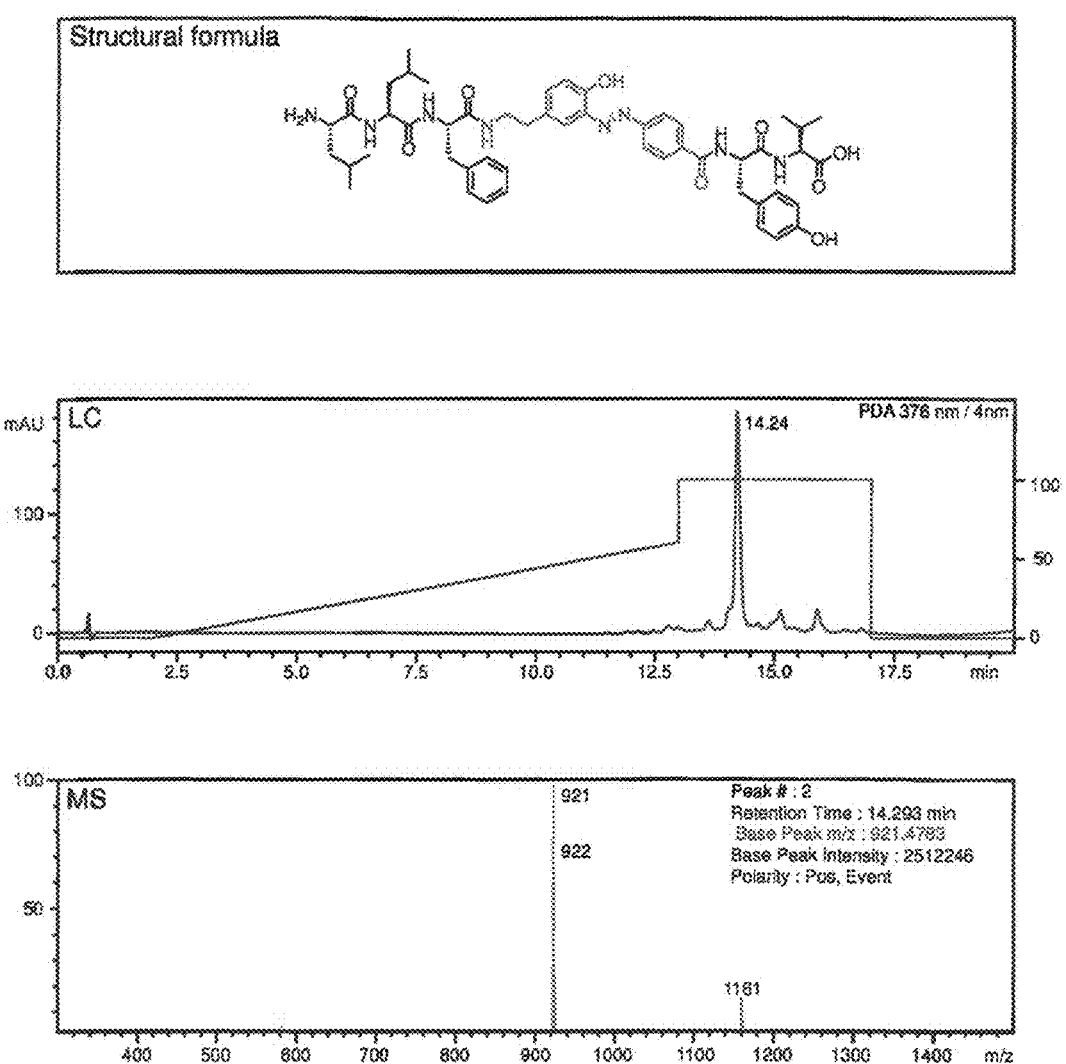

FIG. 5G (Figure S1)
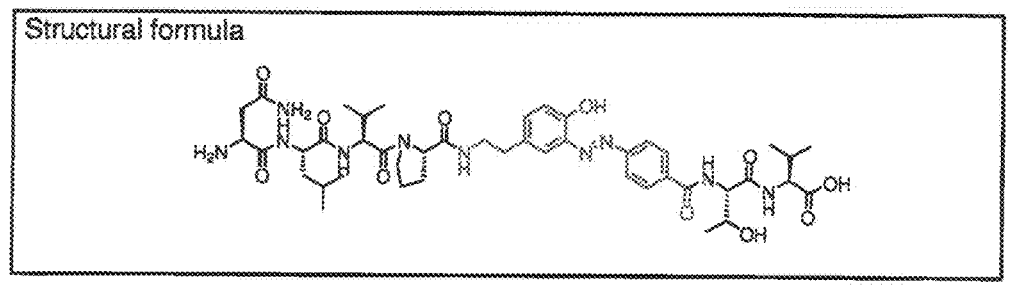
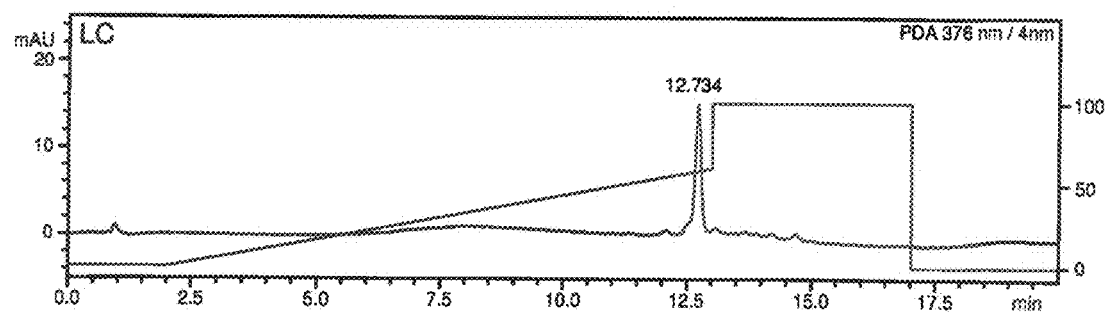
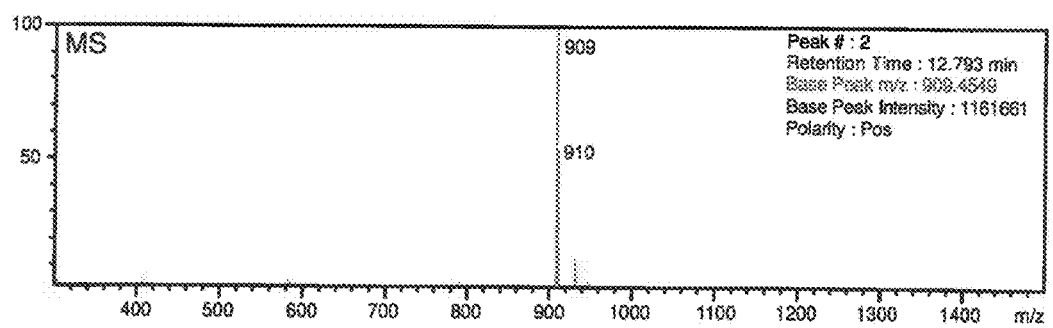

FIG. 5H (Figure S1)
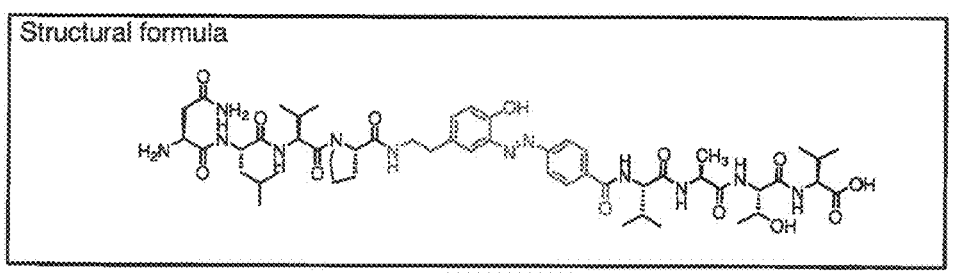
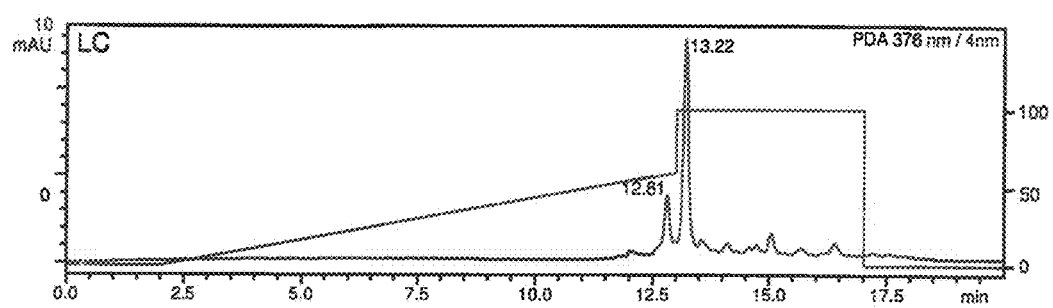
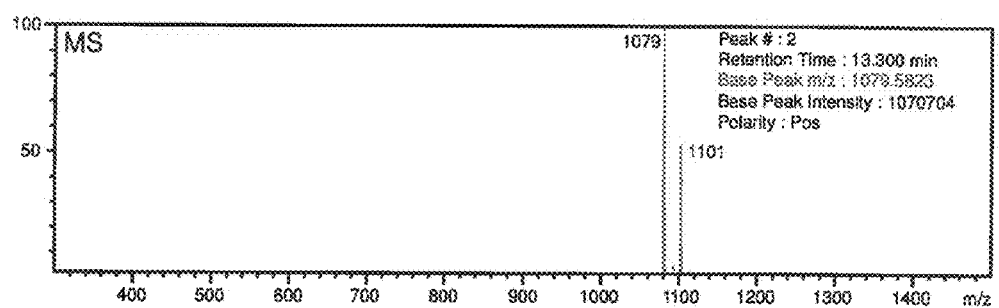

FIG. 5I (Figure S1)
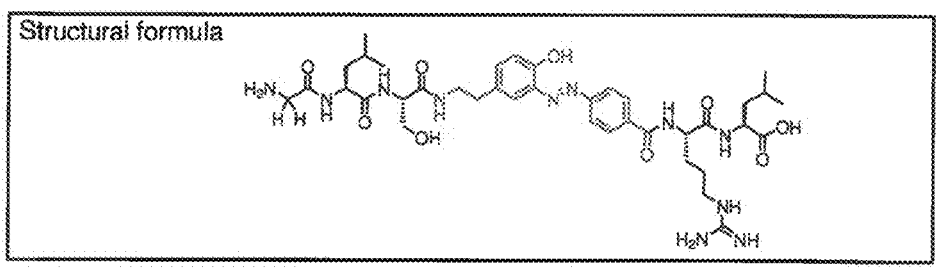
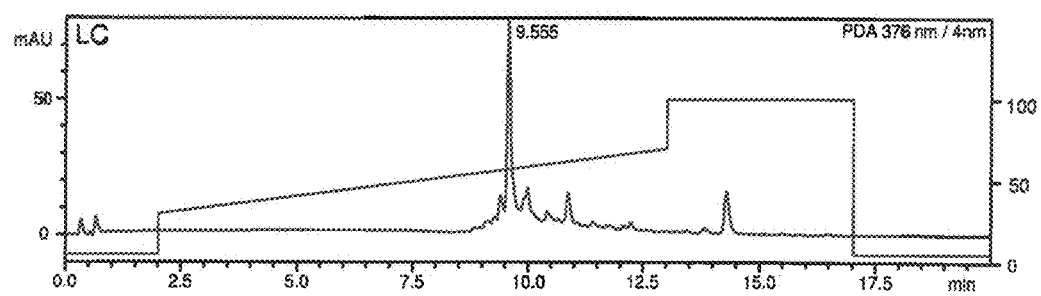
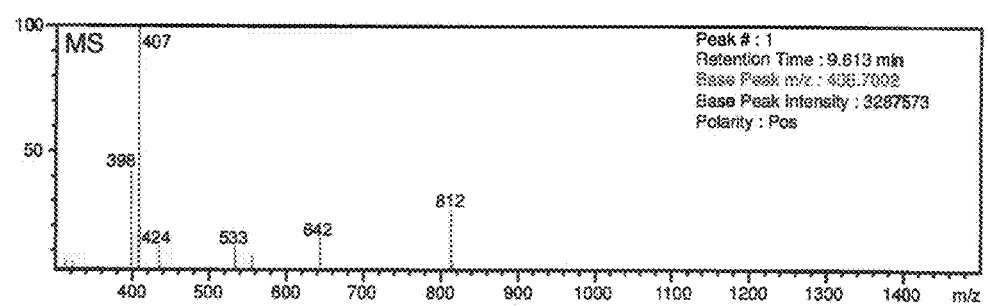

FIG. 5J (Figure S1)
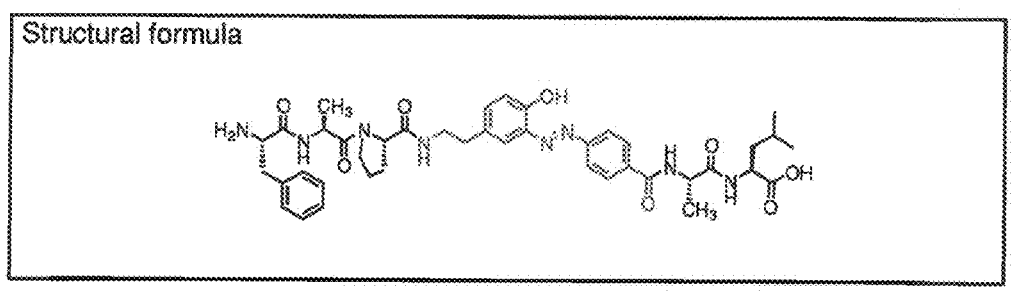
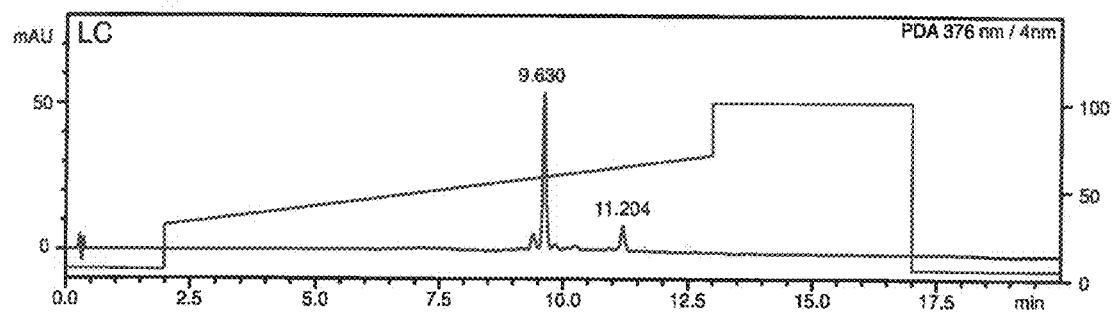
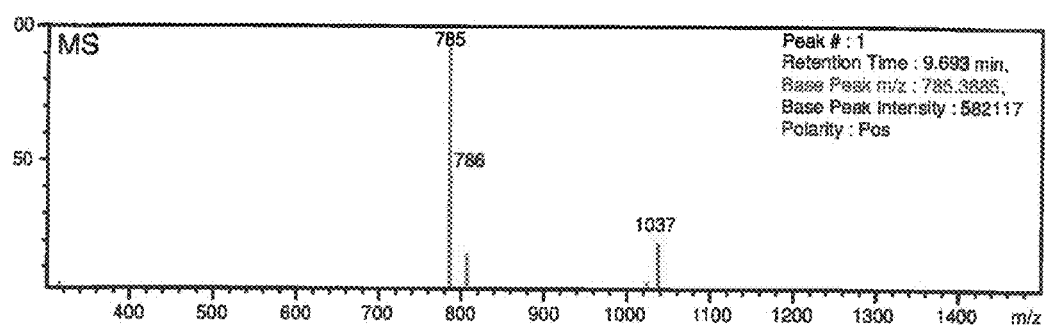

FIG. 5K (Figure S1)
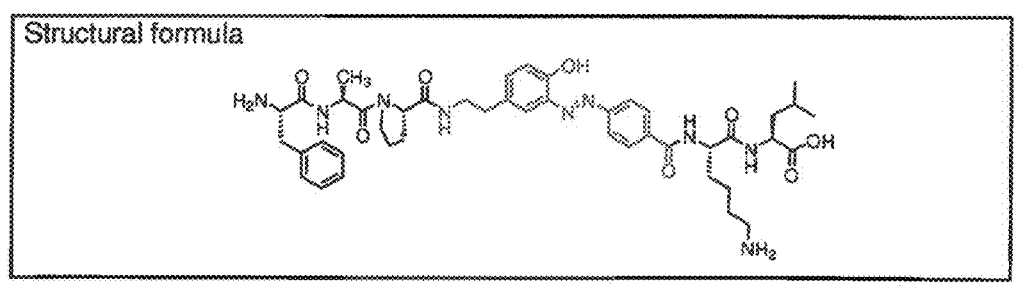
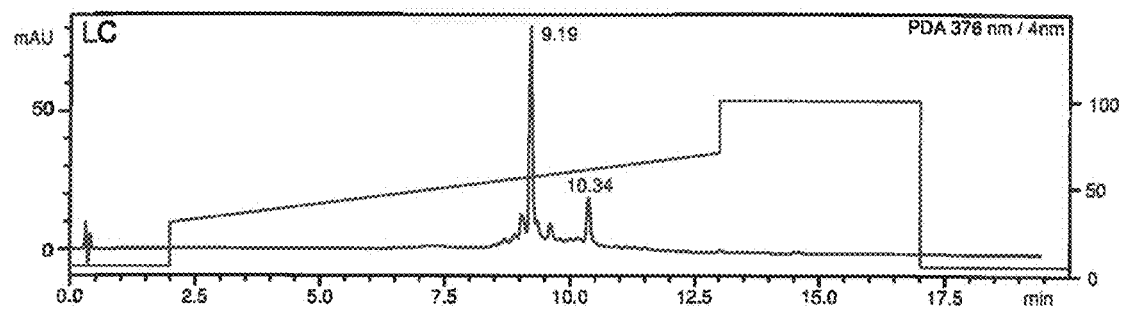
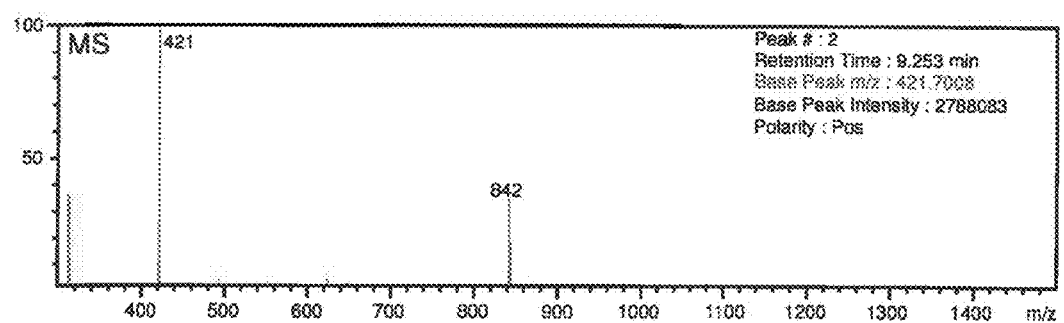

FIG. 6 (Figure S2)
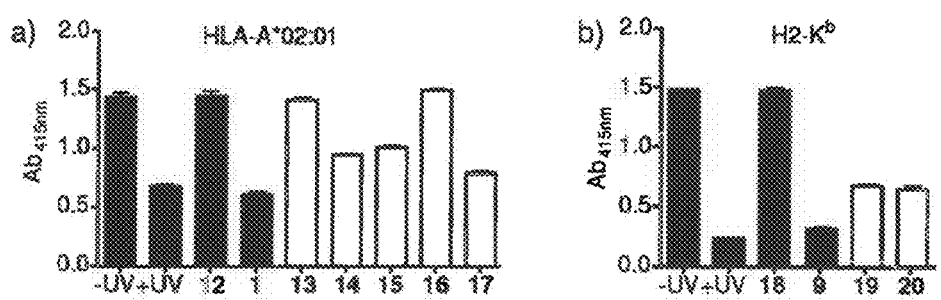
FIG. 7 (Figure S3)
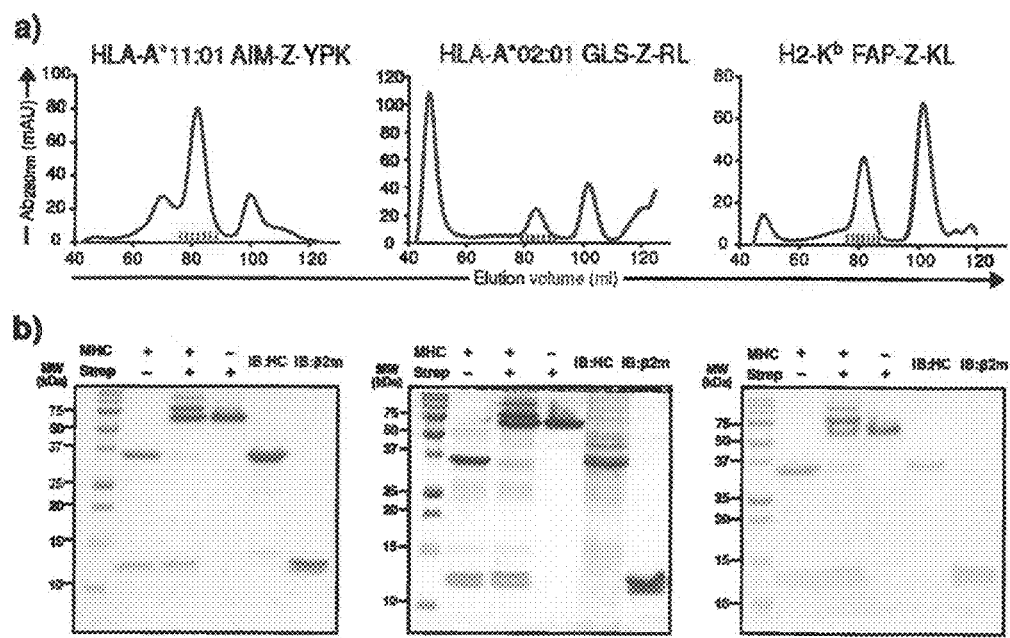

FIG. 8 (Figure S4)
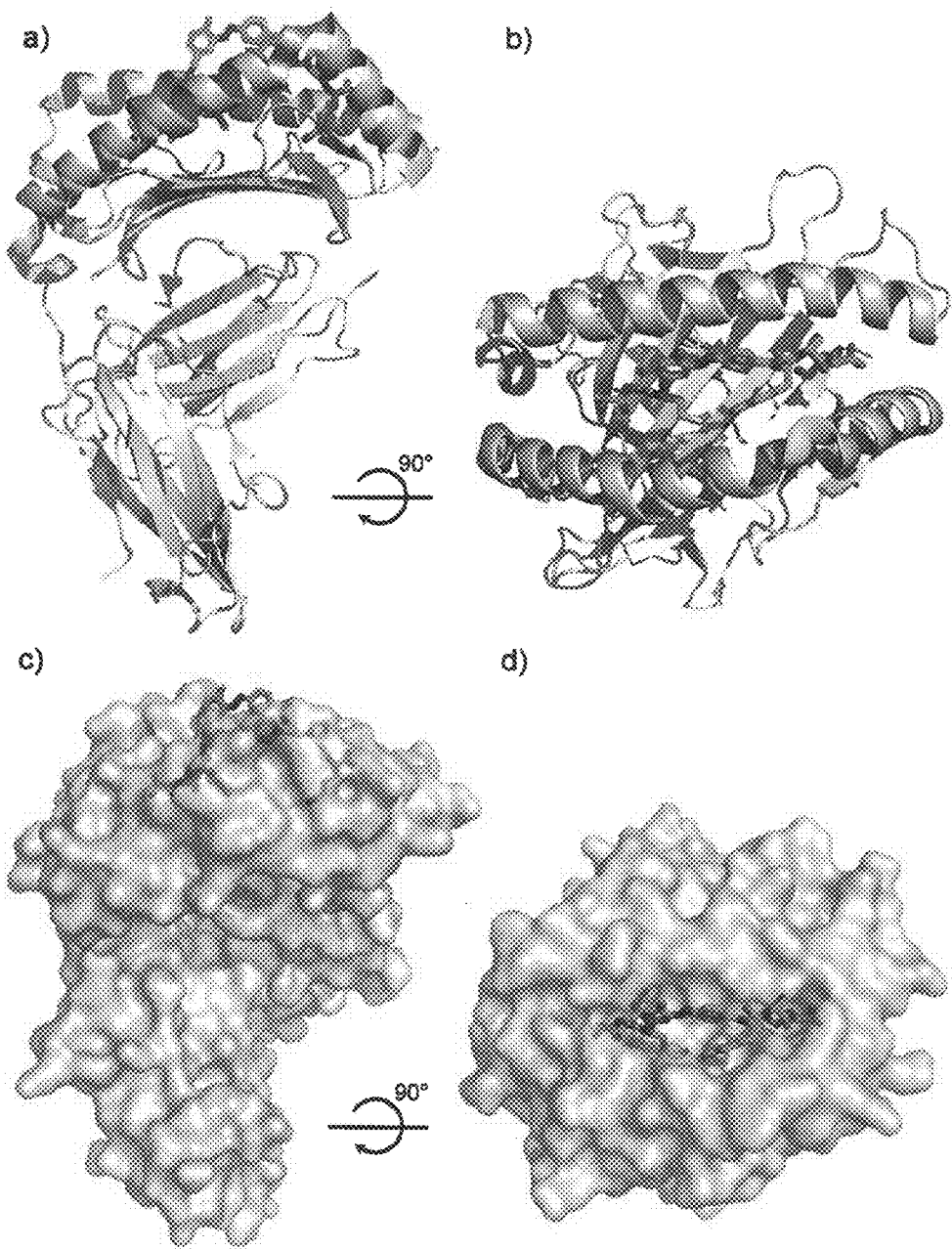

FIG. 9 (Figure S5)
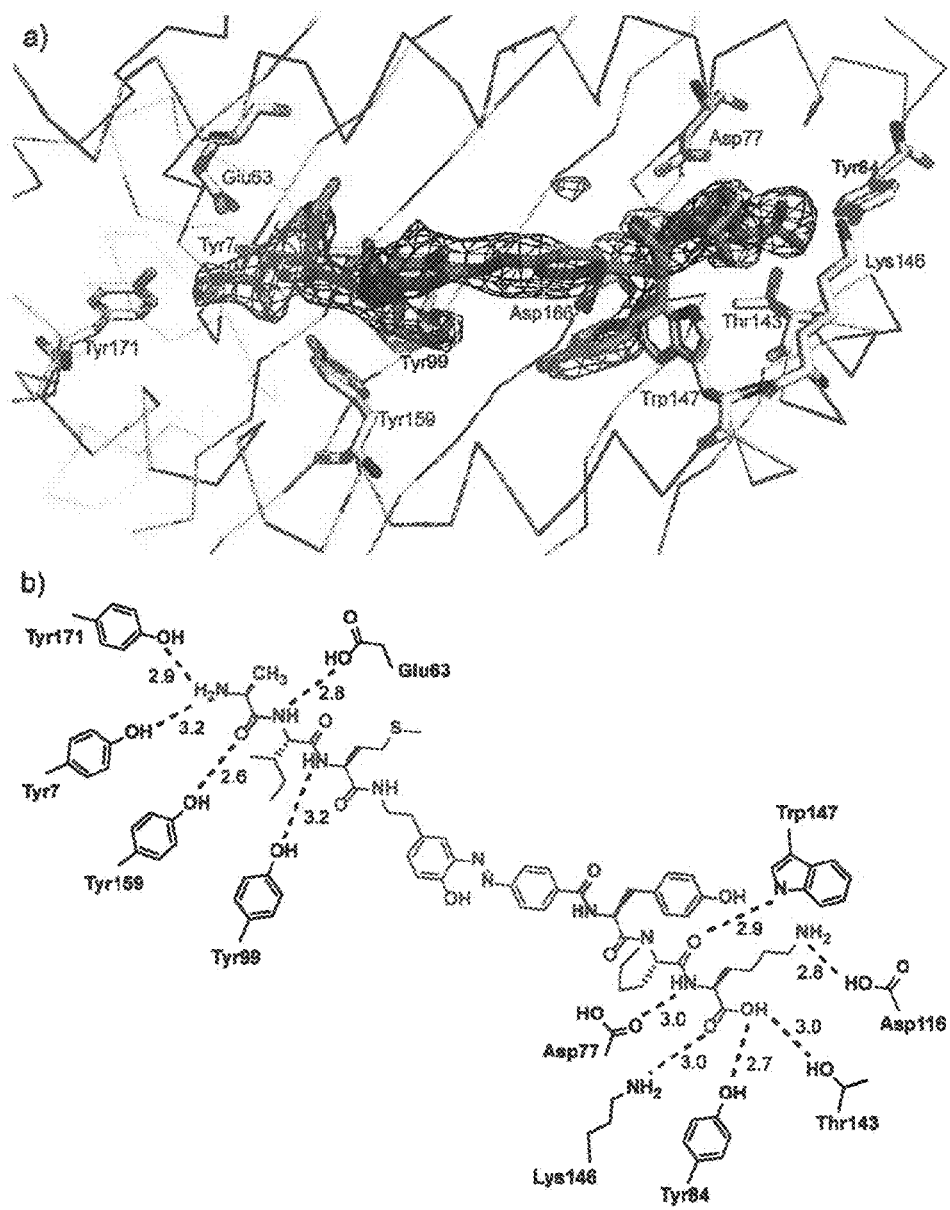

FIG. 10 (Figure S6)
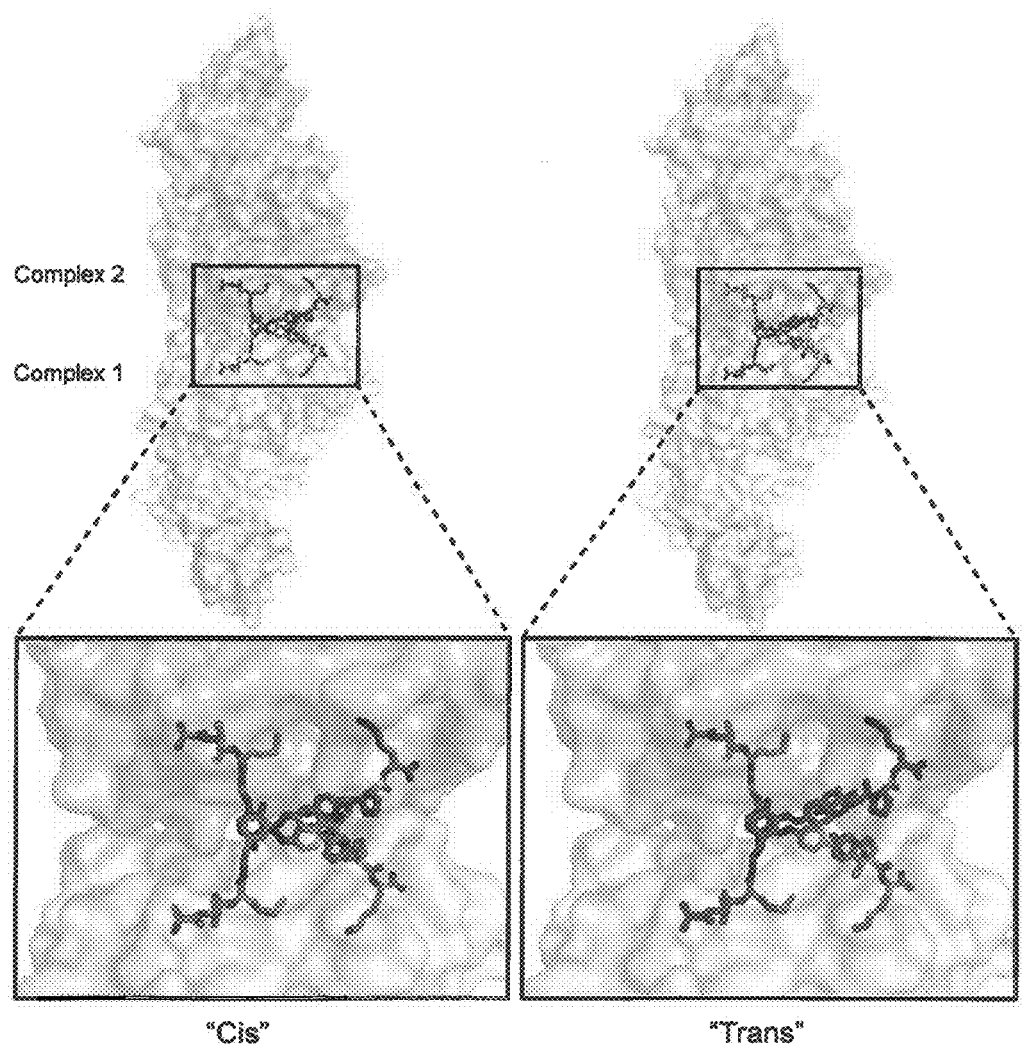

FIG. 11 (Figure S7)
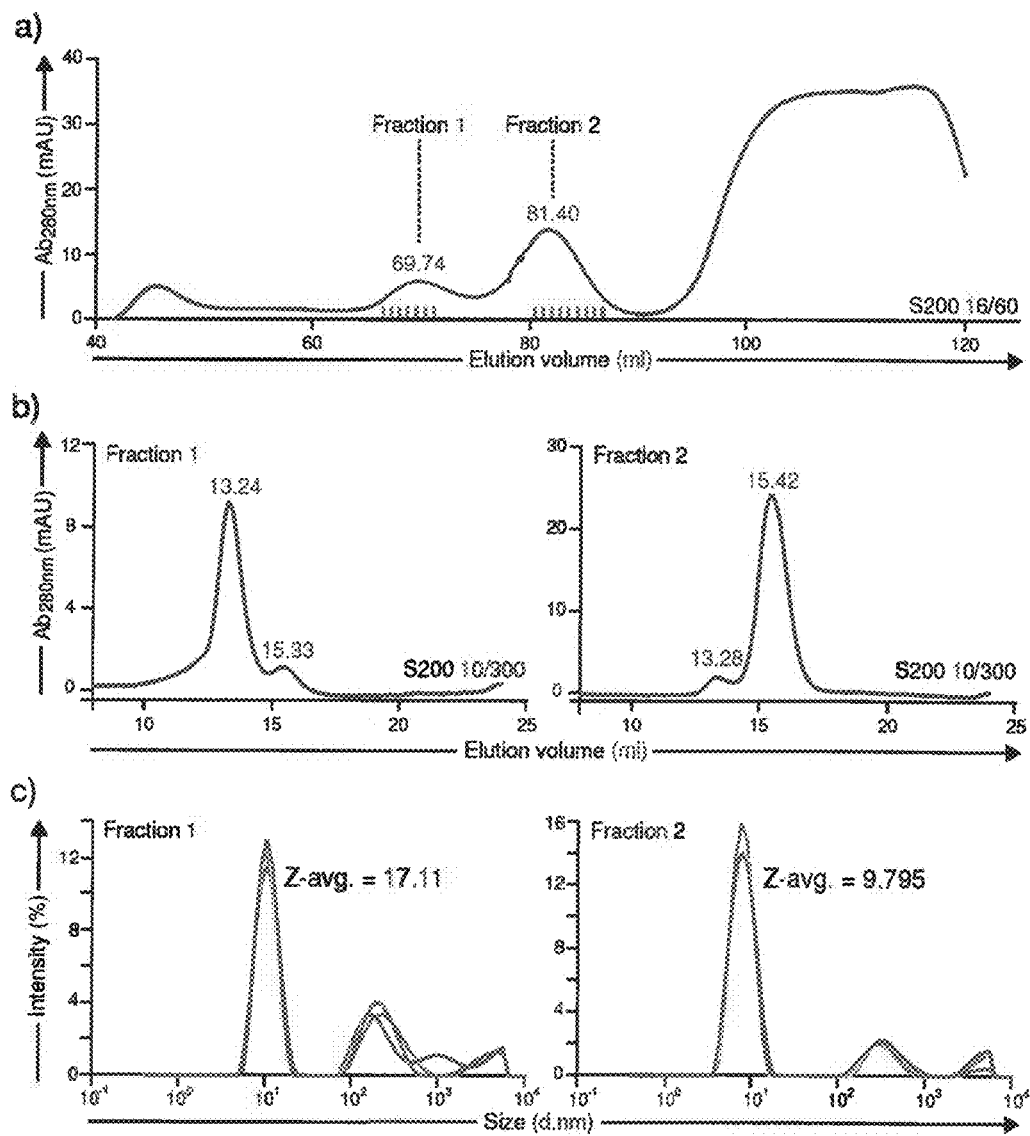

FIG. 12 (Figure S8)
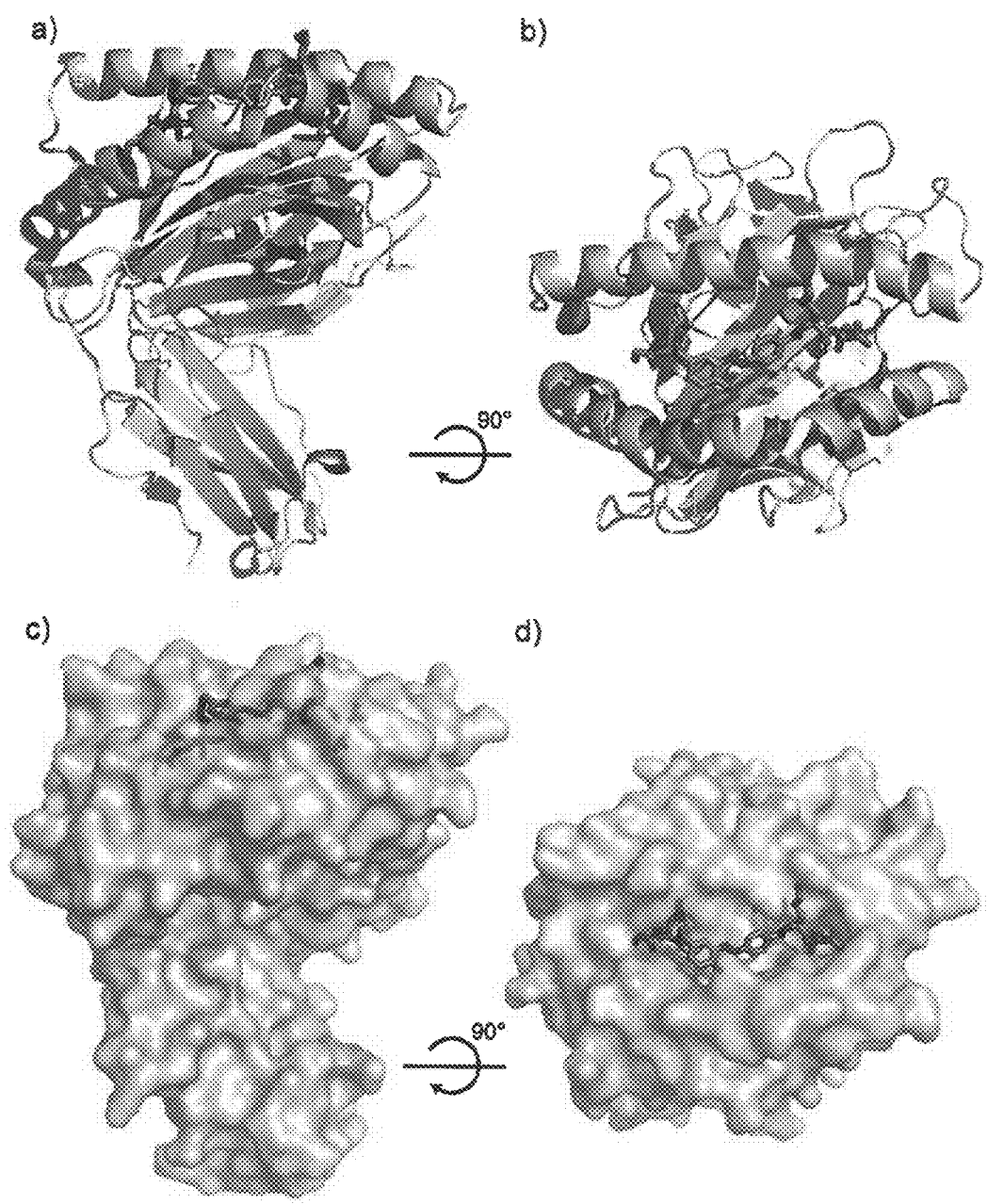

FIG. 13 (Figure S9)
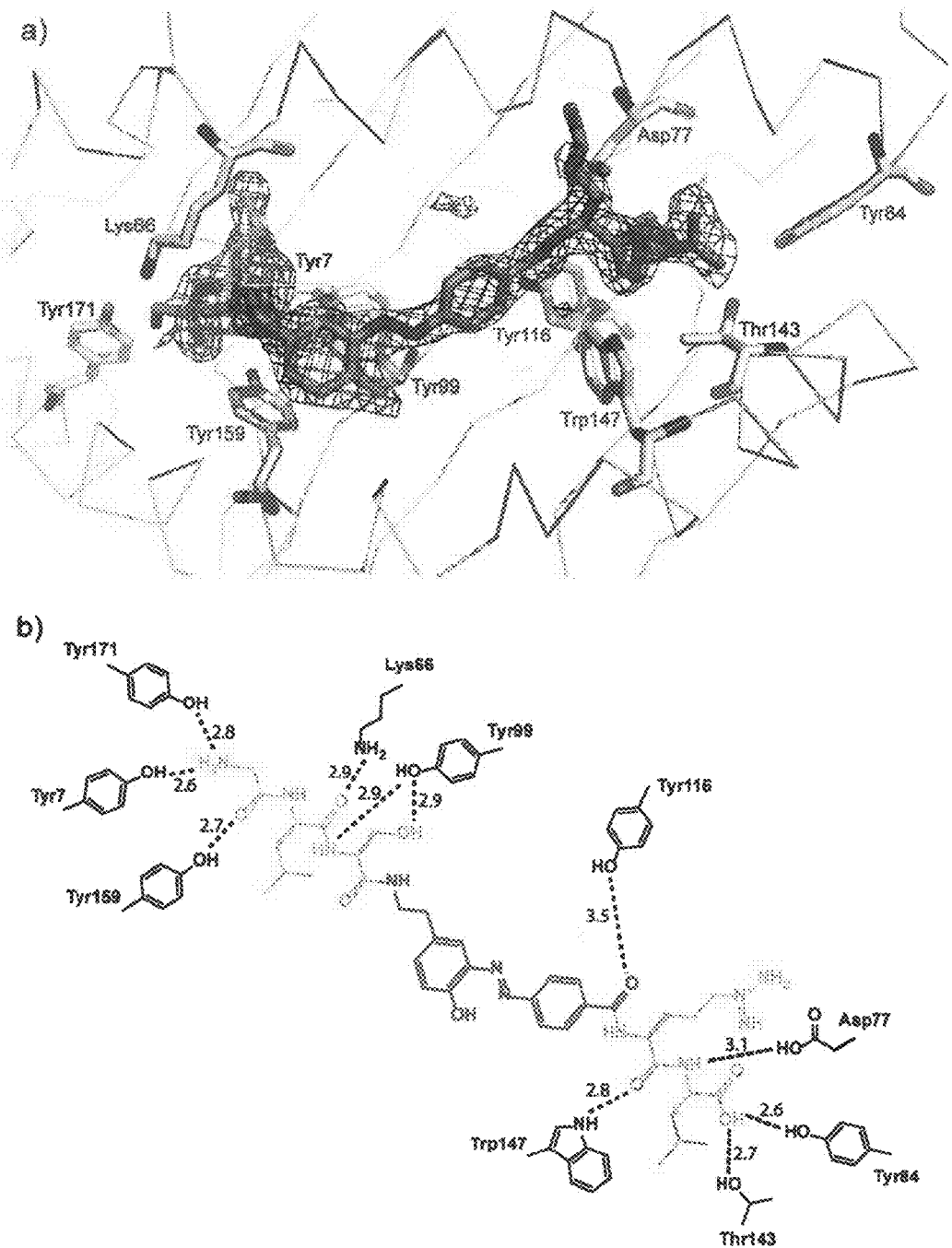

FIG. 14 (Figure S10)
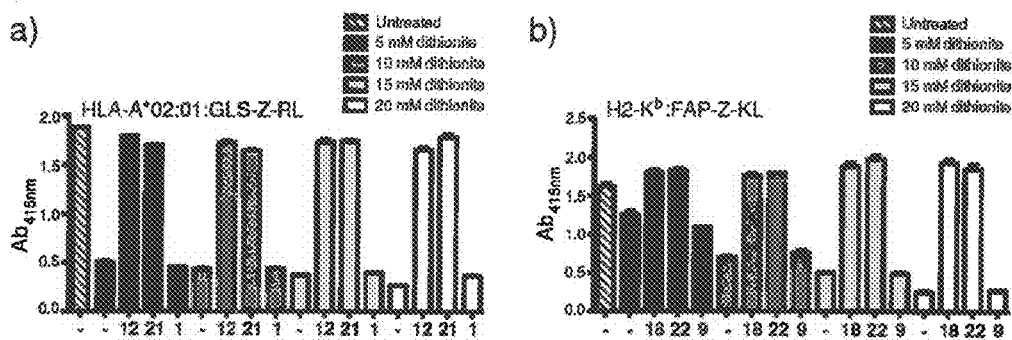
FIG. 15 (Figure S11)
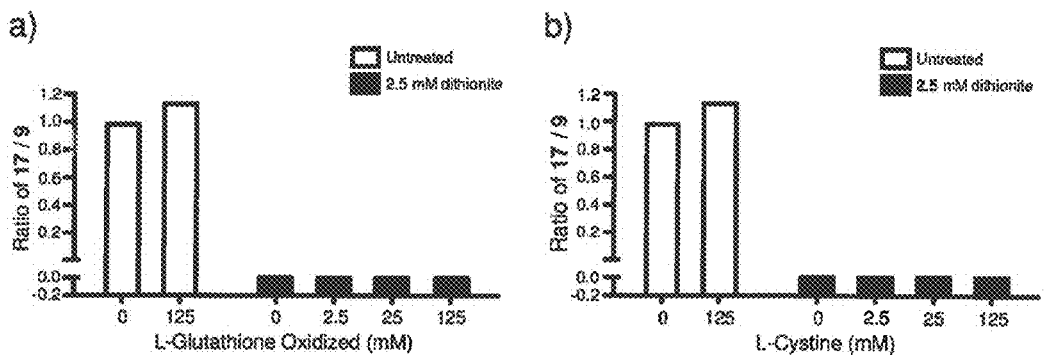
FIG. 16 (Figure S12)
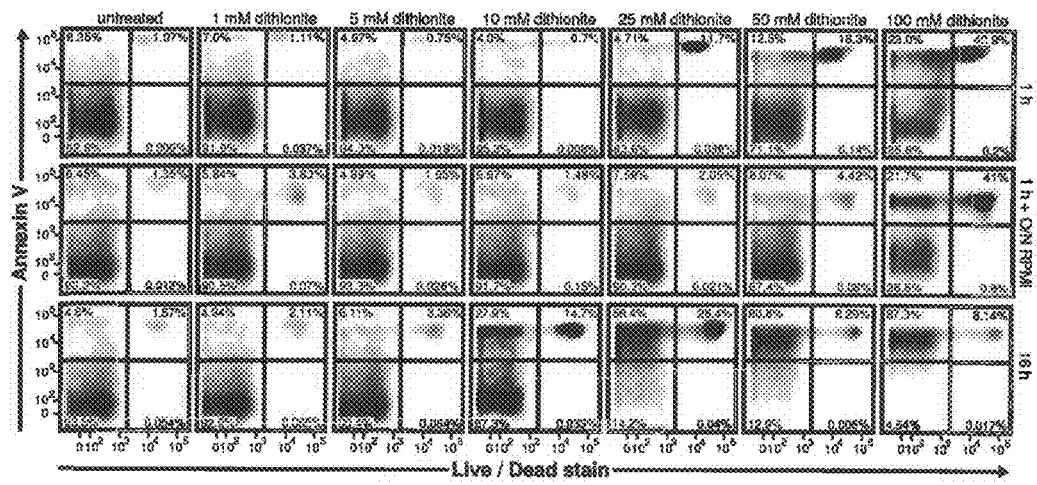

FIG. 17 (Figure S13)
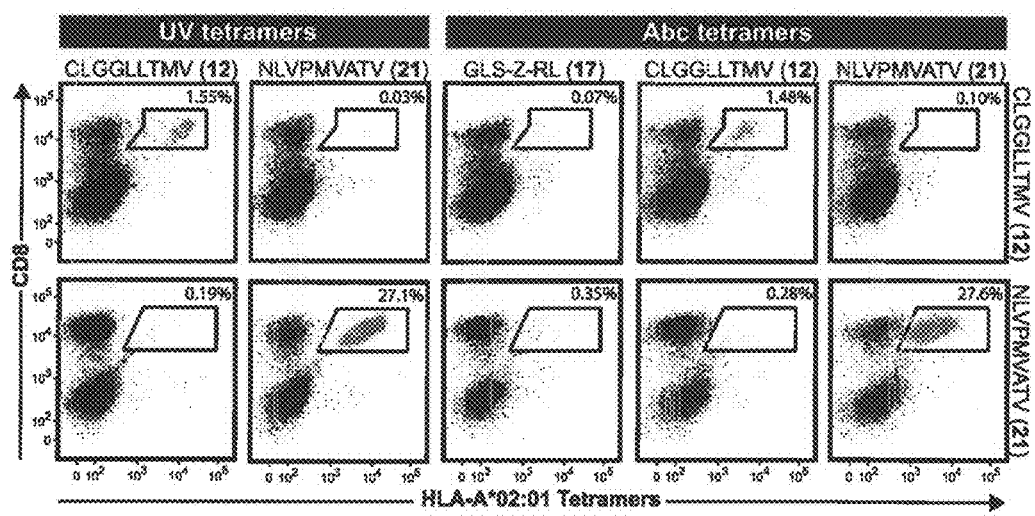
FIG. 18 (Figure S14)
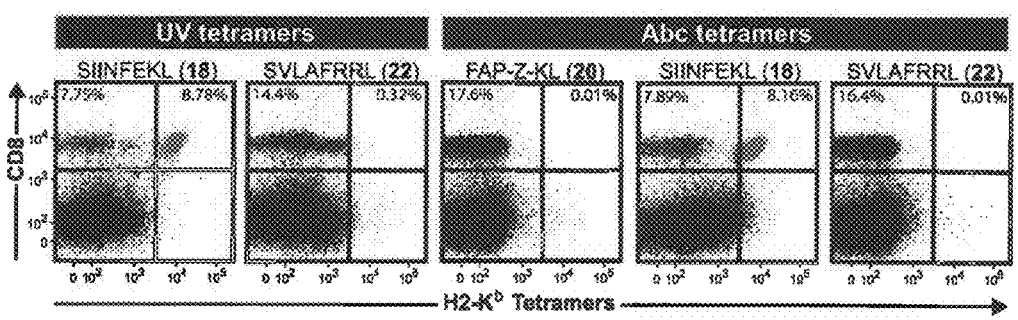

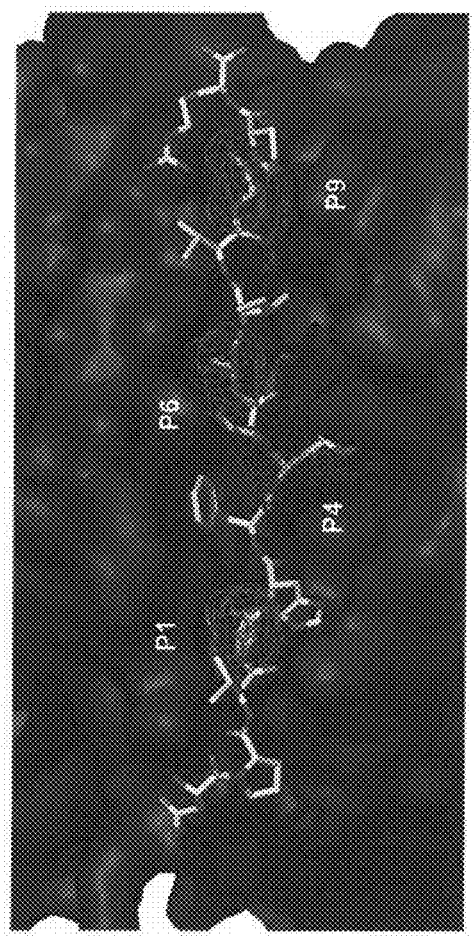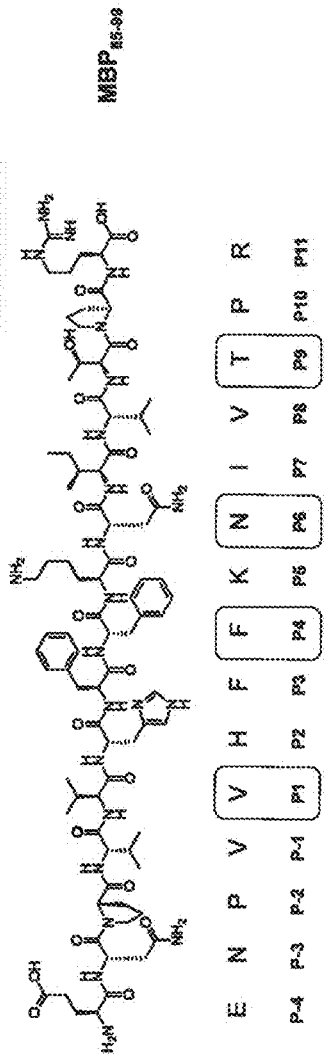
FIG. 19

FIG. 21

Abc-ligands for HLA-A*02:01.

Sequences of the Abc ligands

| Abc ligand | HLA | Parent epitope Sequence | Organism | Protein | Location |
|---|---|---|---|---|---|
| KIL-Z-TV | A*02:01 | GILGFVFTL | Influenza A virus | Matrix 1 | 58-66 |
| KIL-Z-KV | A*02:01 | GILGFVFTL | Influenza A virus | Matrix 1 | 58-66 |
| ILK-Z-GV | A*02:01 | ILKEPVHGV | HIV | Reverse Transcriptase | 468-476 |
| ILK-Z-KV | A*02:01 | ILKEPVHGV | HIV | Reverse Transcriptase | 468-476 |
| ILKE-Z-V | A*02:01 | ILKEPVHGV | HIV | Reverse Transcriptase | 468-476 |

For ILK-Z-GV and ILK-Z-KV exchange data and cell staining data is shown in figure 22 and 23.

FIG. 22
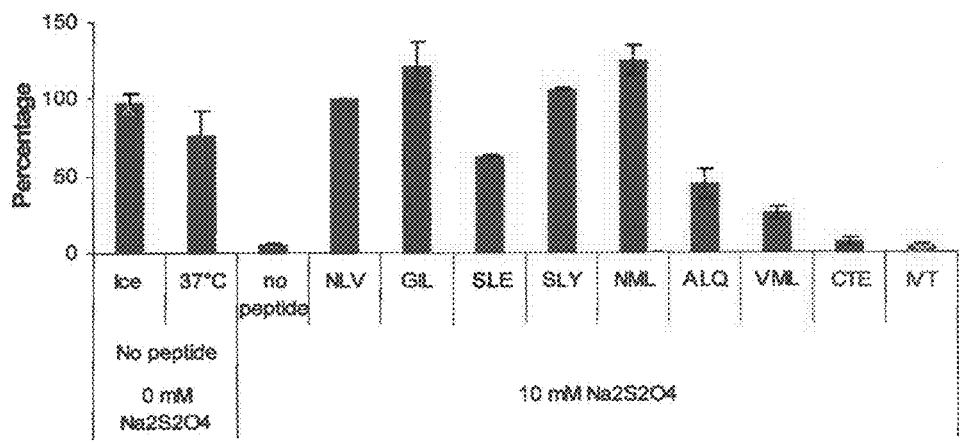
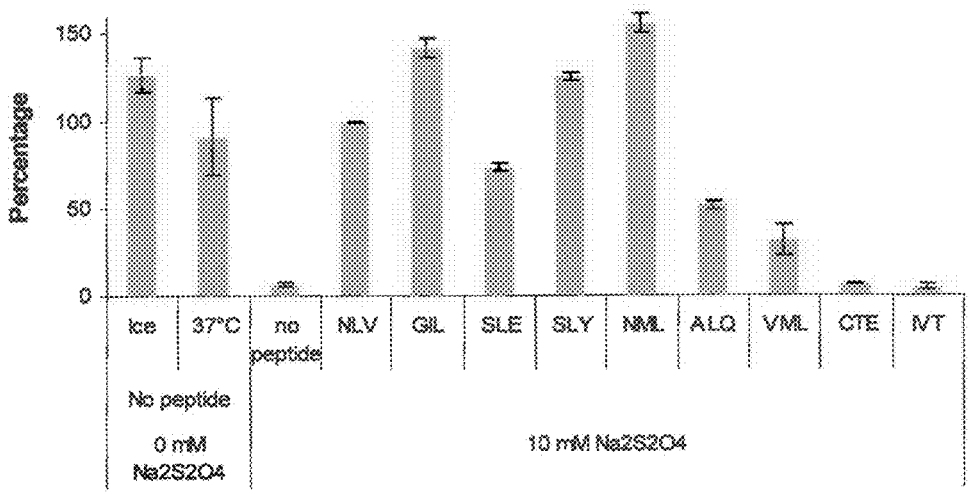
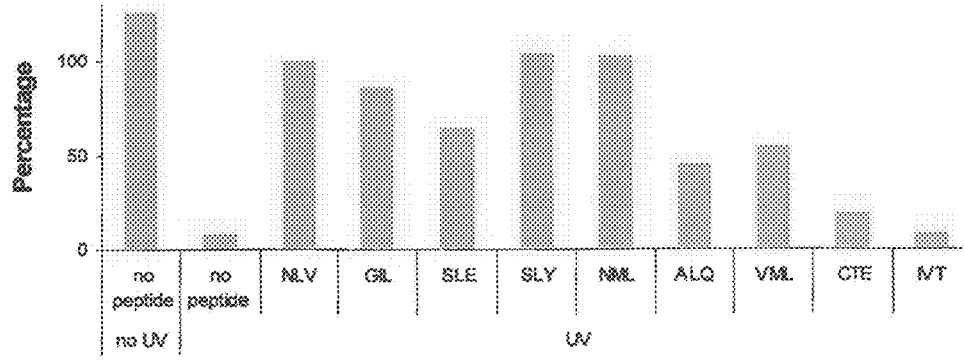

SEQUENCE LISTING

<160> NUMBER OF SEQ ID NOS: 81

<210> SEQ ID NO 1
<211> LENGTH: 9
<212> TYPE: PRT
<213> ORGANISM: Artificial Sequence
<220> FEATURE:
<223> OTHER INFORMATION: epitope

<400> SEQUENCE: 1

Ala Thr Ile Gly Thr Ala Met Tyr Lys
1               5

<210> SEQ ID NO 2
<211> LENGTH: 10
<212> TYPE: PRT
<213> ORGANISM: Artificial Sequence
<220> FEATURE:
<223> OTHER INFORMATION: epitope

<400> SEQUENCE: 2

Phe Leu Pro Ser Asp Phe Phe Pro Ser Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: epitope

<400> SEQUENCE: 3

Ser Ile Ile Pro Ser Gly Pro Leu Lys
1               5

<210> SEQ ID NO 4
<211> LENGTH: 4
<212> TYPE: PRT
<213> ORGANISM: Artificial Sequence
<220> FEATURE:
<223> OTHER INFORMATION: epitope N-terminal part

<400> SEQUENCE: 4

Gln Val Pro Leu
1

<210> SEQ ID NO 5
<211> LENGTH: 15
<212> TYPE: PRT
<213> ORGANISM: Artificial Sequence
<220> FEATURE:
<223> OTHER INFORMATION: MBP epitope

<400> SEQUENCE: 5

Glu Asn Pro Val Val His Phe Phe Lys Asn Ile Val Thr Pro Arg
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: HLA-A*02-02 ligand

<400> SEQUENCE: 6

Gly Ile Leu Gly Phe Val Phe Thr Leu
1               5

<210> SEQ ID NO 7
<211> LENGTH: 9
<212> TYPE: PRT
<213> ORGANISM: Artificial Sequence
<220> FEATURE:
<223> OTHER INFORMATION: HLA-A*02-01 ligand

<400> SEQUENCE: 7

Ile Leu Lys Glu Pro Val His Gly Val
1               5

<210> SEQ ID NO 8
<211> LENGTH: 9
<212> TYPE: PRT
<213> ORGANISM: Artificial Sequence
<220> FEATURE:
<223> OTHER INFORMATION: non-binder to HLA-A*02-01

<400> SEQUENCE: 8

Cys Thr Glu Leu Lys Leu Ser Asp Tyr
1               5

<210> SEQ ID NO 9
<211> LENGTH: 9
<212> TYPE: PRT
<213> ORGANISM: Artificial Sequence
<220> FEATURE:
<223> OTHER INFORMATION: non-binder to HLA-A*02-01

<400> SEQUENCE: 9

Ile Val Thr Asp Phe Ser Val Ile Lys
1               5

<210> SEQ ID NO 10
<211> LENGTH: 9
<212> TYPE: PRT
<213> ORGANISM: Artificial Sequence
<220> FEATURE:
<223> OTHER INFORMATION: intermediate affiniity binding to HLA-A*02-01

<400> SEQUENCE: 10

Ser Leu Glu Asn Phe Arg Ala Tyr Val
1               5

<210> SEQ ID NO 11
<211> LENGTH: 8
<212> TYPE: PRT
<213> ORGANISM: Artificial Sequence
<220> FEATURE:
<223> OTHER INFORMATION: intermediate affiniity binding to HLA-A*02-01

<400> SEQUENCE: 11

Ala Leu Gln Leu Leu Leu Glu Val
1               5

<210> SEQ ID NO 12
<211> LENGTH: 9
<212> TYPE: PRT
<213> ORGANISM: Artificial Sequence
<220> FEATURE:
<223> OTHER INFORMATION: intermediate affiniity binding to HLA-A*02-01

<400> SEQUENCE: 12

Val Met Leu Arg Trp Gly Val Leu Ala
1               5

<210> SEQ ID NO 13
<211> LENGTH: 9
<212> TYPE: PRT
<213> ORGANISM: Artificial Sequence
<220> FEATURE:
<223> OTHER INFORMATION: epitope

<400> SEQUENCE: 13

Asn Leu Val Pro Met Val Ala Thr Val
1               5

<210> SEQ ID NO 14
<211> LENGTH: 9
<212> TYPE: PRT
<213> ORGANISM: Artificial Sequence
<220> FEATURE:
<223> OTHER INFORMATION: epitope

<400> SEQUENCE: 14

Gly Ile Leu Gly Phe Val Phe Thr Leu
1               5

<210> SEQ ID NO 15
<211> LENGTH: 9
<212> TYPE: PRT
<213> ORGANISM: Artificial Sequence
<220> FEATURE:
<223> OTHER INFORMATION: epitope

<400> SEQUENCE: 15

Ser Leu Tyr Asn Thr Val Ala Thr Leu
1               5

<210> SEQ ID NO 16
<211> LENGTH: 9
<212> TYPE: PRT
<213> ORGANISM: Artificial Sequence
<220> FEATURE:
<223> OTHER INFORMATION: high affinity binding to HLA-A*02-01

<400> SEQUENCE: 16

Asn Met Leu Ser Thr Val Leu Gly Val
1               5

<210> SEQ ID NO 17
<211> LENGTH: 9
<212> TYPE: PRT
<213> ORGANISM: Artificial Sequence
<220> FEATURE:
<223> OTHER INFORMATION: HLA restricted epitope
<220> FEATURE:
<221> NAME/KEY: MOD_RES
<222> LOCATION: (8)..(8)
<223> OTHER INFORMATION: 3-Amino-3-(2-nitrophenyl)propionic acid

<400> SEQUENCE: 17

Lys Ile Leu Gly Phe Val Phe Phe Val
1               5

<210> SEQ ID NO 18
<211> LENGTH: 6
<212> TYPE: PRT
<213> ORGANISM: Artificial Sequence
<220> FEATURE:
<223> OTHER INFORMATION: HLA-restricted epitope

<400> SEQUENCE: 18

```
Ile Leu Lys Glx Gly Val
1               5

<210> SEQ ID NO 19
<211> LENGTH: 6
<212> TYPE: PRT
<213> ORGANISM: Artificial Sequence
<220> FEATURE:
<223> OTHER INFORMATION: HLA-restricted epitope

<400> SEQUENCE: 19

Ile Leu Lys Glx Lys Val
1               5

<210> SEQ ID NO 20
<211> LENGTH: 9
<212> TYPE: PRT
<213> ORGANISM: Artificial Sequence
<220> FEATURE:
<223> OTHER INFORMATION: control for competition assay

<400> SEQUENCE: 20

Ile Pro Ala Ala Ala Gly Arg Phe Phe
1               5

<210> SEQ ID NO 21
<211> LENGTH: 9
<212> TYPE: PRT
<213> ORGANISM: Artificial Sequence
<220> FEATURE:
<223> OTHER INFORMATION: epitope

<400> SEQUENCE: 21

Ala Ile Phe Gln Ser Ser Met Thr Lys
1               5

<210> SEQ ID NO 22
<211> LENGTH: 9
<212> TYPE: PRT
<213> ORGANISM: Artificial Sequence
<220> FEATURE:
<223> OTHER INFORMATION: epitope

<400> SEQUENCE: 22

Ile Met Pro Ala Arg Phe Tyr Pro Lys
1               5

<210> SEQ ID NO 23
<211> LENGTH: 10
<212> TYPE: PRT
<213> ORGANISM: Artificial Sequence
<220> FEATURE:
<223> OTHER INFORMATION: epitope

<400> SEQUENCE: 23

Gln Val Pro Leu Arg Pro Met Thr Tyr Lys
1               5                   10

<210> SEQ ID NO 24
<211> LENGTH: 9
<212> TYPE: PRT
<213> ORGANISM: Artificial Sequence
<220> FEATURE:
<223> OTHER INFORMATION: epitope

<400> SEQUENCE: 24

Lys Thr Phe Pro Pro Thr Glu Pro Lys
```

```
1               5
```

<210> SEQ ID NO 25
<211> LENGTH: 10
<212> TYPE: PRT
<213> ORGANISM: Artificial Sequence
<220> FEATURE:
<223> OTHER INFORMATION: epitope

<400> SEQUENCE: 25

```
Phe Leu Pro Ser Asp Phe Phe Pro Ser Val
1               5                   10
```

<210> SEQ ID NO 26
<211> LENGTH: 9
<212> TYPE: PRT
<213> ORGANISM: Artificial Sequence
<220> FEATURE:
<223> OTHER INFORMATION: epitope

<400> SEQUENCE: 26

```
Leu Leu Phe Gly Tyr Pro Val Tyr Val
1               5
```

<210> SEQ ID NO 27
<211> LENGTH: 9
<212> TYPE: PRT
<213> ORGANISM: Artificial Sequence
<220> FEATURE:
<223> OTHER INFORMATION: epitope

<400> SEQUENCE: 27

```
Asn Leu Val Pro Met Val Ala Thr Val
1               5
```

<210> SEQ ID NO 28
<211> LENGTH: 9
<212> TYPE: PRT
<213> ORGANISM: Artificial Sequence
<220> FEATURE:
<223> OTHER INFORMATION: epitope

<400> SEQUENCE: 28

```
Gly Leu Ser Arg Tyr Val Ala Arg Leu
1               5
```

<210> SEQ ID NO 29
<211> LENGTH: 9
<212> TYPE: PRT
<213> ORGANISM: Artificial Sequence
<220> FEATURE:
<223> OTHER INFORMATION: epitope

<400> SEQUENCE: 29

```
Phe Ala Pro Gly Asn Tyr Pro Ala Leu
1               5
```

<210> SEQ ID NO 30
<211> LENGTH: 9
<212> TYPE: PRT
<213> ORGANISM: Artificial Sequence
<220> FEATURE:
<223> OTHER INFORMATION: epitope

<400> SEQUENCE: 30

```
Gly Leu Cys Thr Leu Val Ala Met Leu
1               5
```

<210> SEQ ID NO 31
<211> LENGTH: 9
<212> TYPE: PRT
<213> ORGANISM: Artificial Sequence
<220> FEATURE:
<223> OTHER INFORMATION: epitope

<400> SEQUENCE: 31

Cys Leu Gly Gly Leu Leu Thr Met Val
1               5

<210> SEQ ID NO 32
<211> LENGTH: 9
<212> TYPE: PRT
<213> ORGANISM: Artificial Sequence
<220> FEATURE:
<223> OTHER INFORMATION: epitope

<400> SEQUENCE: 32

Asn Leu Val Pro Met Val Ala Thr Val
1               5

<210> SEQ ID NO 33
<211> LENGTH: 8
<212> TYPE: PRT
<213> ORGANISM: Artificial Sequence
<220> FEATURE:
<223> OTHER INFORMATION: epitope

<400> SEQUENCE: 33

Ser Ile Ile Asn Phe Glu Lys Leu
1               5

<210> SEQ ID NO 34
<211> LENGTH: 8
<212> TYPE: PRT
<213> ORGANISM: Artificial Sequence
<220> FEATURE:
<223> OTHER INFORMATION: epitope

<400> SEQUENCE: 34

Ser Val Leu Ala Phe Arg Arg Leu
1               5

<210> SEQ ID NO 35
<211> LENGTH: 9
<212> TYPE: PRT
<213> ORGANISM: Artificial Sequence
<220> FEATURE:
<223> OTHER INFORMATION: epitope

<400> SEQUENCE: 35

Ile Pro Ala Ala Ala Gly Arg Phe Phe
1               5

<210> SEQ ID NO 36
<211> LENGTH: 15
<212> TYPE: PRT
<213> ORGANISM: Artificial Sequence
<220> FEATURE:
<223> OTHER INFORMATION: parent ligand

<400> SEQUENCE: 36

Gly Glu Leu Ile Gly Ile Leu Asn Ala Ala Lys Val Pro Ala Asp
1               5                   10                  15

```
<210> SEQ ID NO 37
<211> LENGTH: 4
<212> TYPE: PRT
<213> ORGANISM: Artificial Sequence
<220> FEATURE:
<223> OTHER INFORMATION: N-terminal part of Abc ligand

<400> SEQUENCE: 37

Gly Glu Leu Ile
1

<210> SEQ ID NO 38
<211> LENGTH: 6
<212> TYPE: PRT
<213> ORGANISM: Artificial Sequence
<220> FEATURE:
<223> OTHER INFORMATION: N-terminal part of Abc ligand

<400> SEQUENCE: 38

Gly Glu Leu Ile Gly Ile
1               5

<210> SEQ ID NO 39
<211> LENGTH: 7
<212> TYPE: PRT
<213> ORGANISM: Artificial Sequence
<220> FEATURE:
<223> OTHER INFORMATION: N-terminal part of Abc ligand

<400> SEQUENCE: 39

Gly Glu Leu Ile Gly Ile Leu
1               5

<210> SEQ ID NO 40
<211> LENGTH: 7
<212> TYPE: PRT
<213> ORGANISM: Artificial Sequence
<220> FEATURE:
<223> OTHER INFORMATION: N-terminal part of Abc ligand

<400> SEQUENCE: 40

Ala Ala Lys Val Pro Ala Asp
1               5

<210> SEQ ID NO 41
<211> LENGTH: 5
<212> TYPE: PRT
<213> ORGANISM: Artificial Sequence
<220> FEATURE:
<223> OTHER INFORMATION: N-terminal part of Abc ligand

<400> SEQUENCE: 41

Lys Val Pro Ala Asp
1               5

<210> SEQ ID NO 42
<211> LENGTH: 4
<212> TYPE: PRT
<213> ORGANISM: Artificial Sequence
<220> FEATURE:
<223> OTHER INFORMATION: C-terminal part of Abc ligand

<400> SEQUENCE: 42

Val Pro Ala Asp
1
```

```
<210> SEQ ID NO 43
<211> LENGTH: 15
<212> TYPE: PRT
<213> ORGANISM: Artificial Sequence
<220> FEATURE:
<223> OTHER INFORMATION: parent ligand

<400> SEQUENCE: 43

Glu Asn Pro Val Val His Phe Phe Lys Asn Ile Val Thr Pro Arg
1               5                   10                  15

<210> SEQ ID NO 44
<211> LENGTH: 5
<212> TYPE: PRT
<213> ORGANISM: Artificial Sequence
<220> FEATURE:
<223> OTHER INFORMATION: N-terminal part of Abc ligand

<400> SEQUENCE: 44

Glu Asn Pro Val Val
1               5

<210> SEQ ID NO 45
<211> LENGTH: 6
<212> TYPE: PRT
<213> ORGANISM: Artificial Sequence
<220> FEATURE:
<223> OTHER INFORMATION: N-terminal part of Abc ligand

<400> SEQUENCE: 45

Glu Asn Pro Val Val His
1               5

<210> SEQ ID NO 46
<211> LENGTH: 8
<212> TYPE: PRT
<213> ORGANISM: Artificial Sequence
<220> FEATURE:
<223> OTHER INFORMATION: N-terminal part of Abc ligand

<400> SEQUENCE: 46

Glu Asn Pro Val Val His Phe Phe
1               5

<210> SEQ ID NO 47
<211> LENGTH: 6
<212> TYPE: PRT
<213> ORGANISM: Artificial Sequence
<220> FEATURE:
<223> OTHER INFORMATION: C-terminal part of Abc ligand

<400> SEQUENCE: 47

Asn Ile Val Thr Pro Arg
1               5

<210> SEQ ID NO 48
<211> LENGTH: 5
<212> TYPE: PRT
<213> ORGANISM: Artificial Sequence
<220> FEATURE:
<223> OTHER INFORMATION: C-terminal part of Abc ligand

<400> SEQUENCE: 48

Ile Val Thr Pro Arg
1               5

<210> SEQ ID NO 49
```

```
<211> LENGTH: 13
<212> TYPE: PRT
<213> ORGANISM: Artificial Sequence
<220> FEATURE:
<223> OTHER INFORMATION: parent ligand

<400> SEQUENCE: 49

Phe Ser Trp Gly Ala Glu Gly Gln Arg Pro Gly Phe Gly
1               5                   10

<210> SEQ ID NO 50
<211> LENGTH: 4
<212> TYPE: PRT
<213> ORGANISM: Artificial Sequence
<220> FEATURE:
<223> OTHER INFORMATION: N-terminal part of Abc ligand

<400> SEQUENCE: 50

Phe Ser Trp Gly
1

<210> SEQ ID NO 51
<211> LENGTH: 6
<212> TYPE: PRT
<213> ORGANISM: Artificial Sequence
<220> FEATURE:
<223> OTHER INFORMATION: N-terminal part of Abc ligand

<400> SEQUENCE: 51

Phe Ser Trp Gly Ala Glu
1               5

<210> SEQ ID NO 52
<211> LENGTH: 6
<212> TYPE: PRT
<213> ORGANISM: Artificial Sequence
<220> FEATURE:
<223> OTHER INFORMATION: C-terminal part of Abc ligand

<400> SEQUENCE: 52

Gln Arg Pro Gly Phe Gly
1               5

<210> SEQ ID NO 53
<211> LENGTH: 5
<212> TYPE: PRT
<213> ORGANISM: Artificial Sequence
<220> FEATURE:
<223> OTHER INFORMATION: C-terminal part of Abc ligand

<400> SEQUENCE: 53

Arg Pro Gly Phe Gly
1               5

<210> SEQ ID NO 54
<211> LENGTH: 12
<212> TYPE: PRT
<213> ORGANISM: Artificial Sequence
<220> FEATURE:
<223> OTHER INFORMATION: parent ligand

<400> SEQUENCE: 54

Arg Lys Phe His Tyr Leu Pro Phe Leu Pro Ser Thr
1               5                   10

<210> SEQ ID NO 55
<211> LENGTH: 4
```

```
<212> TYPE: PRT
<213> ORGANISM: Artificial Sequence
<220> FEATURE:
<223> OTHER INFORMATION: N-terminal part of Abc ligand

<400> SEQUENCE: 55

Arg Lys Phe His
1

<210> SEQ ID NO 56
<211> LENGTH: 6
<212> TYPE: PRT
<213> ORGANISM: Artificial Sequence
<220> FEATURE:
<223> OTHER INFORMATION: N-terminal part of Abc ligand

<400> SEQUENCE: 56

Arg Lys Phe His Tyr Leu
1               5

<210> SEQ ID NO 57
<211> LENGTH: 5
<212> TYPE: PRT
<213> ORGANISM: Artificial Sequence
<220> FEATURE:
<223> OTHER INFORMATION: C-terminal part of Abc ligand

<400> SEQUENCE: 57

Phe Leu Pro Ser Thr
1               5

<210> SEQ ID NO 58
<211> LENGTH: 4
<212> TYPE: PRT
<213> ORGANISM: Artificial Sequence
<220> FEATURE:
<223> OTHER INFORMATION: C-terminal part of Abc ligand

<400> SEQUENCE: 58

Leu Pro Ser Thr
1

<210> SEQ ID NO 59
<211> LENGTH: 18
<212> TYPE: PRT
<213> ORGANISM: Artificial Sequence
<220> FEATURE:
<223> OTHER INFORMATION: parent ligand

<400> SEQUENCE: 59

Gln Gln Tyr Pro Ser Gly Gln Gly Ser Phe Gln Pro Ser Gln Gln Asn
1               5                   10                  15

Pro Gln

<210> SEQ ID NO 60
<211> LENGTH: 7
<212> TYPE: PRT
<213> ORGANISM: Artificial Sequence
<220> FEATURE:
<223> OTHER INFORMATION: N-terminal part of Abc ligand

<400> SEQUENCE: 60

Gln Gln Tyr Pro Ser Gly Gln
1               5

<210> SEQ ID NO 61
```

<211> LENGTH: 8
<212> TYPE: PRT
<213> ORGANISM: Artificial Sequence
<220> FEATURE:
<223> OTHER INFORMATION: N-terminal part of Abc ligand

<400> SEQUENCE: 61

Gln Gln Tyr Pro Ser Gly Gln Gly
1               5

<210> SEQ ID NO 62
<211> LENGTH: 10
<212> TYPE: PRT
<213> ORGANISM: Artificial Sequence
<220> FEATURE:
<223> OTHER INFORMATION: N-terminal part of Abc ligand

<400> SEQUENCE: 62

Gln Gln Tyr Pro Ser Gly Gln Gly Ser Phe
1               5                   10

<210> SEQ ID NO 63
<211> LENGTH: 7
<212> TYPE: PRT
<213> ORGANISM: Artificial Sequence
<220> FEATURE:
<223> OTHER INFORMATION: C-terminal part of Abc ligand

<400> SEQUENCE: 63

Pro Ser Gln Gln Asn Pro Gln
1               5

<210> SEQ ID NO 64
<211> LENGTH: 6
<212> TYPE: PRT
<213> ORGANISM: Artificial Sequence
<220> FEATURE:
<223> OTHER INFORMATION: C-terminal part of Abc ligand

<400> SEQUENCE: 64

Ser Gln Gln Asn Pro Gln
1               5

<210> SEQ ID NO 65
<211> LENGTH: 4
<212> TYPE: PRT
<213> ORGANISM: Artificial Sequence
<220> FEATURE:
<223> OTHER INFORMATION: C-terminal part of Abc ligand

<400> SEQUENCE: 65

Gln Asn Pro Gln
1

<210> SEQ ID NO 66
<211> LENGTH: 13
<212> TYPE: PRT
<213> ORGANISM: Artificial Sequence
<220> FEATURE:
<223> OTHER INFORMATION: parent ligand

<400> SEQUENCE: 66

Phe Glu Ala Gln Lys Ala Lys Ala Asn Lys Ala Val Asp
1               5                   10

<210> SEQ ID NO 67
<211> LENGTH: 5

```
<212> TYPE: PRT
<213> ORGANISM: Artificial Sequence
<220> FEATURE:
<223> OTHER INFORMATION: N-terminal part of Abc ligand

<400> SEQUENCE: 67

Phe Glu Ala Gln Lys
1               5

<210> SEQ ID NO 68
<211> LENGTH: 6
<212> TYPE: PRT
<213> ORGANISM: Artificial Sequence
<220> FEATURE:
<223> OTHER INFORMATION: N-terminal part of Abc ligand

<400> SEQUENCE: 68

Phe Glu Ala Gln Lys Ala
1               5

<210> SEQ ID NO 69
<211> LENGTH: 6
<212> TYPE: PRT
<213> ORGANISM: Artificial Sequence
<220> FEATURE:
<223> OTHER INFORMATION: C-terminal part of Abc ligand

<400> SEQUENCE: 69

Ala Asn Lys Ala Val Asp
1               5

<210> SEQ ID NO 70
<211> LENGTH: 4
<212> TYPE: PRT
<213> ORGANISM: Artificial Sequence
<220> FEATURE:
<223> OTHER INFORMATION: C-terminal part of Abc ligand

<400> SEQUENCE: 70

Lys Ala Val Asp
1

<210> SEQ ID NO 71
<211> LENGTH: 17
<212> TYPE: PRT
<213> ORGANISM: Artificial Sequence
<220> FEATURE:
<223> OTHER INFORMATION: parent ligand

<400> SEQUENCE: 71

Ile Ser Gln Ala Val His Ala Ala His Ala Glu Ile Asn Glu Ala Gly
1               5                   10                  15

Arg

<210> SEQ ID NO 72
<211> LENGTH: 4
<212> TYPE: PRT
<213> ORGANISM: Artificial Sequence
<220> FEATURE:
<223> OTHER INFORMATION: N-terminal part of Abc mutant

<400> SEQUENCE: 72

Ile Ser Gln Ala
1

<210> SEQ ID NO 73
```

```
<211> LENGTH: 5
<212> TYPE: PRT
<213> ORGANISM: Artificial Sequence
<220> FEATURE:
<223> OTHER INFORMATION: N-terminal part of Abc mutant

<400> SEQUENCE: 73

Ile Ser Gln Ala Val
1               5

<210> SEQ ID NO 74
<211> LENGTH: 11
<212> TYPE: PRT
<213> ORGANISM: Artificial Sequence
<220> FEATURE:
<223> OTHER INFORMATION: C-terminal part of Abc ligand

<400> SEQUENCE: 74

Ala Ala His Ala Glu Ile Asn Glu Ala Gly Arg
1               5                   10

<210> SEQ ID NO 75
<211> LENGTH: 9
<212> TYPE: PRT
<213> ORGANISM: Artificial Sequence
<220> FEATURE:
<223> OTHER INFORMATION: C-terminal part of Abc ligand

<400> SEQUENCE: 75

His Ala Glu Ile Asn Glu Ala Gly Arg
1               5

<210> SEQ ID NO 76
<211> LENGTH: 8
<212> TYPE: PRT
<213> ORGANISM: Artificial Sequence
<220> FEATURE:
<223> OTHER INFORMATION: C-terminal part of Abc ligand

<400> SEQUENCE: 76

Ala Glu Ile Asn Glu Ala Gly Arg
1               5

<210> SEQ ID NO 77
<211> LENGTH: 12
<212> TYPE: PRT
<213> ORGANISM: Artificial Sequence
<220> FEATURE:
<223> OTHER INFORMATION: parent ligand

<400> SEQUENCE: 77

Ala Asp Leu Ile Ala Tyr Leu Lys Gln Ala Thr Lys
1               5                   10

<210> SEQ ID NO 78
<211> LENGTH: 4
<212> TYPE: PRT
<213> ORGANISM: Artificial Sequence
<220> FEATURE:
<223> OTHER INFORMATION: N-terminal part of Abc mutant

<400> SEQUENCE: 78

Ala Asp Leu Ile
1

<210> SEQ ID NO 79
<211> LENGTH: 5
```

```
<212> TYPE: PRT
<213> ORGANISM: Artificial Sequence
<220> FEATURE:
<223> OTHER INFORMATION: N-terminal part of Abc mutant

<400> SEQUENCE: 79

Ala Asp Leu Ile Ala
1               5

<210> SEQ ID NO 80
<211> LENGTH: 7
<212> TYPE: PRT
<213> ORGANISM: Artificial Sequence
<220> FEATURE:
<223> OTHER INFORMATION: N-terminal part of Abc mutant

<400> SEQUENCE: 80

Ala Asp Leu Ile Ala Tyr Leu
1               5

<210> SEQ ID NO 81
<211> LENGTH: 4
<212> TYPE: PRT
<213> ORGANISM: Artificial Sequence
<220> FEATURE:
<223> OTHER INFORMATION: C-terminal part of Abc ligand

<400> SEQUENCE: 81

Gln Ala Thr Lys
1
```

CLEAVAGE AND EXCHANGE OF MAJOR HISTOCOMPATIBILITY COMPLEX LIGANDS EMPLOYING AZOBENZENE-CONTAINING PEPTIDES

CROSS-REFERENCE TO RELATED APPLICATIONS

This application is a national phase entry under 35 U.S.C. § 371 of International Patent Application PCT/NL2015/050407, filed Jun. 5, 2015, designating the United States of America and published in English as International Patent Publication WO 2015/187019 A1 on Dec. 10, 2015, which claims the benefit under Article 8 of the Patent Cooperation Treaty to European Patent Application Serial No. 14171590.4, filed Jun. 6, 2014.

TECHNICAL FIELD

The application relates to the field of major histocompatibility complex molecules (MHC). The disclosure, in particular, relates to an MHC molecule that contains a linker in the peptide binding groove of the MHC molecule, where the linker is cleavable, thereby allowing for easy exchange with peptide antigens of interest. The disclosure further relates to means and methods for producing an MHC molecule having desired a MHC peptide in the peptide binding groove of the MHC and to cleavable ligands.

BACKGROUND

Chemical strategies have been progressively applied to understand and manipulate biological systems. The chemical reactivity of the employed reagents needs to be tuned such that interference with essential biochemical or cellular processes is prevented. Several bioorthogonal reactions have been developed to enable site-selective conjugation of macromolecules with a myriad of probes (e.g., luminescent dyes, photo-responsive moieties etc.),[1] yet the conditional breaking of bonds in the presence of a large heterogeneity of functional groups has received less attention. Cleavable linkers that can be chemoselectively addressed in a biocompatible manner have started to see deployment in disciplines such as biochemistry, proteomics, and cell biology.[2]

One successful application in immunobiology has facilitated the detection of disease-specific T-cell responses within large reservoirs of other cells. T-lymphocytes belong to the cellular arm of the adaptive immune system and are tasked to recognize and eliminate virus-infected or tumor cells. They express a large diversity of clonally distributed surface receptors that govern their specificity toward a cognate antigenic peptide fragment presented by major histocompatibility complexes (MHCs). Recombinantly produced oligomers of the latter heterotrimeric glycoprotein complex can bind to and stain T-cells of corresponding specificity, and the conventional MHC tetramer format has become a cornerstone technology for mapping T-cell responses in basic and clinical research on infectious diseases, autoimmunity, cancer and vaccine development.[3]

Libraries of MHC molecules such as tetramer libraries are among others accessible through synthetic ligands that are released through UV-induced cleavage of the peptide backbone, enabling a novel epitope to refill the evacuated MHC peptide-binding groove.[4] Arrays of the peptide-exchanged MHC tetramers enabled the interrogation of T-cell repertoires, regardless of their functional activity. Technical limitations such as low UV penetration, variability in UV irradiation, and the potential of photo and thermal damage to the protein complexes, highlighted the need for alternative modes of cleavage. Chemoselective peptide exchange, although conceptually feasible, should avoid compromising the replacement epitope with its unprotected functionalities at the amino acid residue side-chains as well as N- and C-termini, or risk the loss of T-cell antigen-recognition.

BRIEF SUMMARY

This disclosure provides the use of azobenzene (Abc, Z) linkers that are sensitive to sodium dithionite ($Na_2S_2O_4$). The term "Abc" is in the description and claims directed toward the azobenzene structure. In the examples of the disclosure, Abc typically relates to the azobenzene-containing linker. The Abc is a stereocenter-free building block that is accessible from readily available starting materials by a straightforward and cost-effective synthesis route. Furthermore, the Abc moiety is unaffected by reducing agents common to biological protocols (e.g., TCEP, DTT) and the fragmentation conditions have been demonstrated to be compatible with biomolecules and living systems.[5]

In one aspect, the disclosure provides a major histocompatibility complex (MHC) molecule comprising a ligand in the peptide binding groove of the MHC molecule, whereby the ligand comprises an azobenzene (Abc) wherein at least one of the aromatic rings comprises an electron-donor group. The electron-donor group is preferably a hydroxyl in the ortho position relative to the azo group. The azobenzene further comprises at least two amino acid residues separated by the azo group of the Abc, and wherein the amino acid residues are positioned to interact with the peptide binding groove of the MHC molecule. It is preferred that the ligand is an MHC peptide antigen of which amino acid residues that are located between the amino acid residues have been replaced by an Abc. The Abc preferably comprises the general formula I

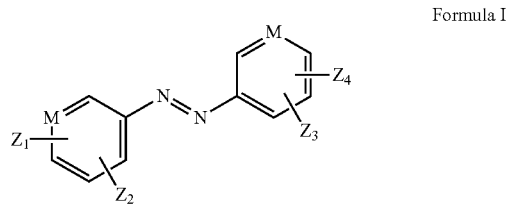

Formula I wherein
at least one of the aromatic rings comprise an electron-donating group;

M is independently C, S, N or O;

$Z_1$ and $Z_4$ each comprise an amino acid residue positioned to interact with the peptide binding groove of the MHC molecule;

$Z_2$ and $Z_3$ are independently H, hydroxyl, carboxy, keto, or a linear or branched $C_1$-$C_{10}$ alkyl, optionally substituted with an oxy, hydroxyl, nitrogen, nitroxy, sulhydryl or sulfide group.

In a preferred embodiment, the Abc comprises the general formula II

Formula II

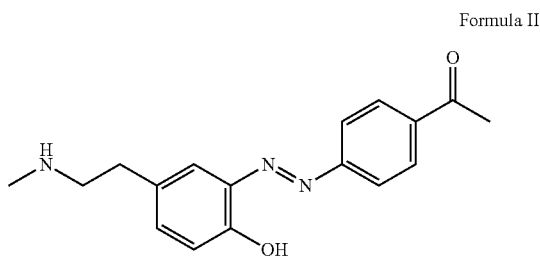 [SMILES: CNCCc1ccc(O)c(/N=N/c2ccc(C(C)=O)cc2)c1]

The ligand preferably comprises the general formula III

Formula III

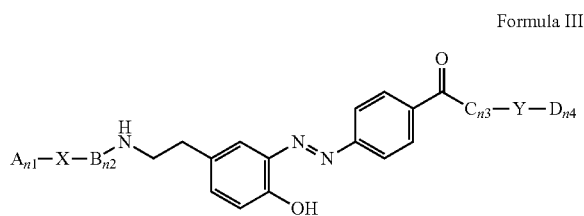

wherein,

A, B, C, D, X and Y are each independently an amino acid residue;

$n_1$, $n_2$, $n_3$ and $n_4$ are each independently 0-11; and $n_1+n_2+n_3+n_4$ equals 2-18.

The disclosure further provides a complex comprising one, two or more MHC molecules of the disclosure.

Further provided is a composition comprising an MHC molecule of the disclosure and/or a complex of the disclosure and an MHC peptide antigen.

The disclosure further provides a method of producing an MHC molecule comprising:
  producing an MHC molecule of the disclosure;
  contacting the produced MHC molecule with a reducing agent; and
  contacting the MHC molecule with an MHC peptide antigen.

The disclosure further provides a method of detecting an MHC molecule comprising producing an MHC molecule by a method of the disclosure, and detecting the MHC molecule. The MHC molecule, the peptide in the peptide binding groove of the MHC molecule, or both, preferably comprise a label.

The disclosure further provides a solid surface comprising an MHC molecule or a complex of the disclosure.

The disclosure further provides an azobenzene of formula I

Formula I

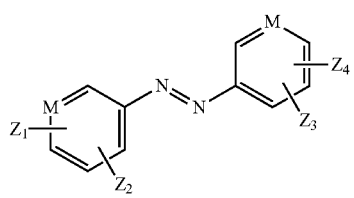

wherein
  at least one of the aromatic rings comprises an electron-donating group;
  M is independently C, S, N or O;
  Z1 and Z4 each comprise an amino acid residue positioned to interact with the peptide binding groove of an MHC molecule;
  Z2 and Z3 are independently H, hydroxyl, carboxy, keto, or a linear or branched $C_1$-$C_{10}$ alkyl, optionally substituted with an oxy, hydroxyl, nitrogen, nitroxy, sulhydryl or sulfide group.

Further provided is an azobenzene of the disclosure for use in the production of an MHC molecule comprising a peptide in the peptide binding groove of the MHC molecule.

As used herein, the term "polypeptide" refers to a molecule comprising at least 50 amino acids or functional equivalents thereof that are linked to each other via peptide bonds. In its unfolded state, the polypeptide is typically a linear molecule but can be (partly) circular. A peptide typically contains between 2 and 49 amino acids that are linked to each other via peptide bonds.

An amino acid can be a natural or synthetic amino acid such as, for instance, an alpha, beta, or gamma or higher (omega) amino acid, i.e., including 1, 2, 3, or more carbon spacings between amino groups and carboxylic acids. An amino acid (chain) can be a natural amino acid (chain) or a synthesized amino acid (chain) or a combination thereof. A peptide is a natural peptide or a synthesized peptide or a combination thereof. In its unfolded state, a peptide is typically linear, but can be (partly) circular. A peptide typically does not have a dominant tertiary structure. It typically accommodates a range of tertiary structures. A "peptide" as used in the disclosure is typically easily dissolvable in diverse solvents. Such solvents are, for instance, physiological solutions, such as a physiological sodium chloride solution. Alternatively, peptides can be dissolved in a solvent as DMSO and subsequently brought into an aqueous environment.

The terms "peptide antigen" and "MHC peptide antigen" are used interchangeably herein and refer to an MHC ligand that can bind in the peptide binding groove of an MHC molecule. The peptide antigen can typically be presented by the MHC molecule. A peptide antigen typically has between 8 and 25 amino acids that are linked via peptide bonds. The peptide can contain modification such as, but not limited to, the side chains of the amino acid residues, the presence of a label or tag, the presence of a synthetic amino acid, a functional equivalent of an amino acid, or the like. Typical modifications include those as produced by the cellular machinery, such as glycan addition and phosphorylation. However, other types of modification are also within the scope of the disclosure.

"A functional equivalent of an amino acid" is a molecule that can replace one or more amino acids in an amino acid chain. The functional equivalent is preferably capable of forming bonds with amino acids in two separate positions such that it can form an internal part of a (poly)peptide or peptidomimetic chain. The functional equivalent does not have to have a natural counterpart. Such a functional equivalent can be incorporated into a peptide or peptide antigen of the disclosure.

The major histocompatibility complex (MHC) is a set of cell surface molecules encoded by a large gene family in all vertebrates. In humans, MHC is also called "human leukocyte antigen" (HLA).

An MHC molecule displays a peptide and presents it to the immune system of the vertebrate. The peptide is also referred to as a ligand, a peptide antigen or an MHC peptide antigen and can be either a self or a non-self peptide. MHC class I molecules typically present the peptide antigen to CD8-positive T-cells, whereas MHC class II molecules present the peptide antigen to CD4-positive T-cells.

MHC molecules are encoded by polygenic and exceptionally polymorphic gene families. It is thought that the diversity provides a survival advantage against pathogens. Allelic polymorphism for each of the genes is particularly prominent in those amino acid residues that line the peptide-binding groove of these molecules. The observed diversity in the amino acid residues of the peptide binding groove of the MHC molecules defines the peptide-binding and the presentation repertoire of the individual MHC molecule (Chang et al. 2011; *Frontiers in Bioscience*, Landmark Edition, Vol. 16:3014-3035). Through the vast repertoire of allelic variants of MHC molecules such as the HLA molecules in the general population, each of them capable of binding a distinct set of peptide antigens, a mechanism is created to deal with the large diversity of antigens of pathogens. At the same time, significant cross-reactivity in peptide antigen binding to different MHC/HLA molecules has been observed. It has been proposed to cluster HLAs that bind overlapping collections of peptides into supertypes. For HLA, the various HLA-A and HLA-B molecules have been grouped into a limited number of supertypes based on their ability to binding similar peptide sequences (Sidney et al. 2008, *BMC Immunology* Vol. 9:1). Crystallography and experimental evidence has revealed that peptide binding specificity is primarily governed by the physiochemical properties of the B and F binding pockets in a coupled fashion (see FIG. 1 of Chang et al. 2011 supra). The B and F binding pockets typically bind to so-called "anchor residues" in the peptide that define the binding of the peptide in the peptide binding groove of the MHC. The specificity of the pockets for anchor residues has been elucidated for a large number MHC molecules. For HLA, the pocket specificity is among others described in Sidney et al. (2008 supra), which is incorporated by reference herein for the binding specificity of the B and F pockets for the respective HLA molecules and HLA supertypes mentioned therein.

The ligand that binds to the peptide binding groove of the MHC molecule can be a naturally occurring peptide but can also be synthetically created using the knowledge of the binding specificity of the B and F pocket of the particular MHC molecule or the supertype family it belongs to.

The ligand of this disclosure utilizes an azobenzene as a cleavable linker. The azobenzene is a chemical compound composed of two phenyl rings linked by an N=N double bond (azo group). It is the simplest example of an azo compound. The term "azobenzene" or simply "azo" is often used to refer to a wide class of molecules that share the core azobenzene structure, with different chemical functional groups extending from the phenyl rings. Azo compounds are sometimes referred to as "diazenes." In this disclosure, the azobenzene is preferably sensitive to sodium dithionite ($Na_2S_2O_4$).

At least one of the aromatic rings of the azobenzene comprises an electron-donating (or electron-donor) group. The electron-donor group is preferably an amine group, an amide group, an aromatic group, an alkene group, an alkoxy group, a hydroxyl group or a ketone or a carboxyl group. The electron-donor group is preferably in the ortho or the para (mesomeric) position relative to the position of the azo-group. In one aspect, the amine is a primary, secondary or tertiary amine. In a preferred embodiment, the amino is a primary amine. In another aspect, the electron-donor group is a hydroxyl, ketone, or carboxy-group. In a preferred embodiment, the electron-donor group is a hydroxyl group. The hydroxyl, ketone or carboxy-group is preferably in the ortho-position relative to position of the azo-group. The alkoxy group, when present, is preferably in the para-position relative to the azo-group. In a preferred embodiment, the azobenzene of the disclosure comprises the general formula IV,

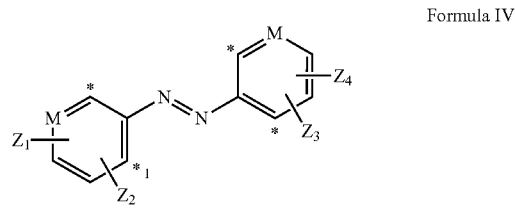

Formula IV wherein
"*" indicates that the azobenzene has at least one hydroxyl in the ortho position relative to the azo group; the hydroxyl is preferably in the position *1 as indicated in the general formula IV;
M is independently C, S, N or O;
Z1 and Z4 each comprise an amino acid residue positioned to interact with the peptide binding groove of an MHC molecule;
Z2 and Z3 are independently H, hydroxyl, carboxy, keto, or a linear or branched $C_1$-$C_{10}$ alkyl, optionally substituted with an oxy, hydroxyl, nitrogen, nitroxy, sulhydryl or sulfide group.

The azobenzene can be obtained with the use of readily available starting materials by a straightforward and cost-effective synthesis route. Furthermore, the Abc moiety is unaffected by reducing agents common to biological protocols (e.g., TCEP, DTT) and the correct fragmentation conditions have been demonstrated to be compatible with biomolecules and living systems.[5]

The ligand further comprises amino acid residues separated by the azo group of the Abc and positioned to interact with a peptide binding groove of the MHC molecule. The separation by the azo group ensures that upon cleavage of the azo group, the ligand is fragmented into fragments that each contain less amino acid residues interacting with the peptide binding groove.

Suitable ligands can be generated using the available 3D structures of MHC complexes and the knowledge on the binding pocket specificity of the respective MHC molecules. Binding characteristics can be evaluated using 3D-crystallography as exemplified in the examples. A suitable starting point for the design of the ligand is a known MHC peptide antigen. One or more of the amino acids can be replaced by the Abc. In a preferred embodiment, one or more of the amino acid residues that are located between anchor amino acid residues are replaced by the Abc. In a preferred embodiment, the ligand is an MHC peptide antigen of which amino acid residues that are located between anchor amino acid residues have been replaced by the Abc.

The Abc preferably comprises the general formula I:

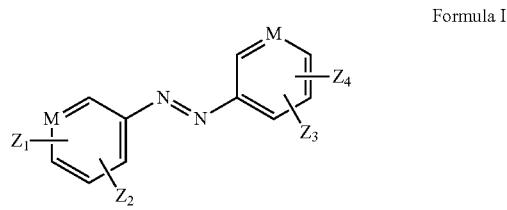

Formula I wherein
at least one of the aromatic rings comprise an electron-donating group;
M is independently C, S, N or O;
Z1 and Z4 each comprise an amino acid residue positioned to interact with the peptide binding groove of the MHC molecule;
Z2 and Z3 are independently H, hydroxyl, carboxy, keto, or a linear or branched $C_1$-$C_{10}$ alkyl, optionally substituted with an oxy, hydroxyl, nitrogen, nitroxy, sulhydryl or sulfide group.

Although phenyl is the preferred aromatic group, i.e., M=C, other heteroaromatic groups may be used, e.g., pyridyl, M=N. X may also be S or O. Z2 and Z3 indicate that the present activity of the cleavable linker is maintained with certain modifications to the aryl diazo structure. Tolerable substitutions include lower alkyl, hydroxyl, carboxy or keto.

Z1 and Z4 each comprise an amino acid residue positioned to interact with the peptide binding groove of the MHC molecule. The amino acid residue is preferably positioned by $C_{1-2}$ alkyl group that is located between the benzene ring and the amino acid residue. Z1 or Z4 preferably further comprises an NH located between the alkyl group and the amino acid residue. The $C_{1-2}$ alkyl group, preferably of Z4, may optionally be substituted by the keto group.

Z1 is preferably linked to the phenyl at the meta position relative to the azo group, preferably at the meta position indicated by M, in general formula I. Z4 is preferably linked to the phenyl at the para position relative to the azo group.

The Abc preferably comprises the general formula II

Formula II

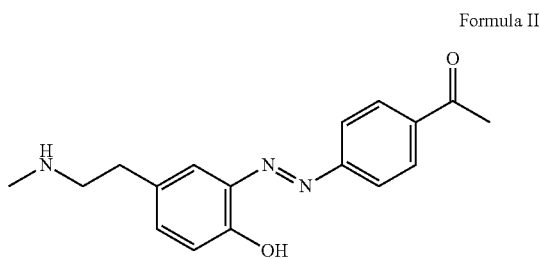 [SMILES: CNCCc1ccc(O)c(/N=N/c2ccc(C(C)=O)cc2)c1]

The left and right "-" line indicates that the Abc is linked to an amino acid residue at that position. It does not indicate the presence of a "—CH3" group at that position.

The ligand preferably comprises the general formula III

Formula III

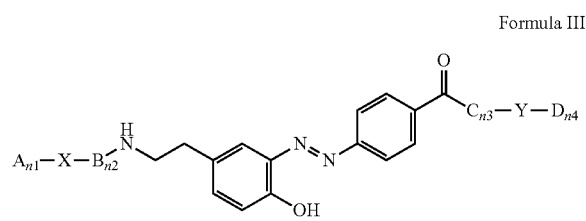

wherein,
A, B, C, D, X and Y are each independently an amino acid residue;
$n_1$, $n_2$, $n_3$ and $n_4$ are each independently 0-11; and
$n_1+n_2+n_3+n_4$ equals 2-18.
The Abc is preferably a trans-Abc.

The integers $n_2$ and $n_3$ are preferably chosen such that the amino acid residues X and Y are positioned to interact with the peptide binding groove of the MHC molecule.

MHC class I molecules typically bind peptides that are 8-10 amino acid residues in length. For MHC class I molecules, $n_1+n_2+n_3+n_4$ equals 2, 3, 4, 5, 6, 7 or 8. $n_1+n_2+n_3+n_4$ preferably equals 2, 3, 4, 5, or 6; preferably 2, 3, 4 or 5; more preferably 2, 3 or 4. In a preferred embodiment, $n_1+n_2+n_3+n_4$ equals 2 or 3 for an MHC class I ligand. The structure between B and C extends in essence the same distance as four amino residues. As MHC class I peptides are typically 8-10 amino acids; the ligand of formula III typically comprise 4-6 amino acids.

Because the antigen-binding groove of MHC class II molecules is open at both ends while the corresponding groove on class I molecules is closed at each end, the antigens presented by MHC class II molecules can generally be longer. MHC class II binding peptides are typically 15-24 amino acid residues long. Artificial class II binding peptides can be smaller than 15 amino acid residues. Accommodating the size of the Abc, the sum of $n_1+n_2+n_3+n_4$ for typical MHC II ligands is 2-18. The lower end of the sum range is preferably 3. In a preferred embodiment, the sum is 6-14; more preferably 7-13.

The MHC class II binding groove typically has four major pockets. These pockets accommodate the side chains of residues 1, 4, 6 and 9 of the 9-mer core region of the binding peptide. This core region largely determines binding affinity and specificity (Wang et al. 2008; PLoS Comput. Biol. 4(4):e1000048, Doi:10.1371/journal.pcbi.100048). Structural features of binding of peptides to the respective grooves can be found among other in H.-G. Rammensee (1995, Chemistry of peptides associated with MHC class I and class II molecules, Curr. Opin. Immunol. 7:85). Amino acid residues that bind to the specific pockets of the peptide binding groove of MHC molecules are also referred to as anchor residues. Amino acid residues that are positioned to interact with the peptide binding groove in a ligand of the disclosure are preferably anchor amino acid residues.

For MHC class I, the amino acid residues are preferably positioned to interact with the peptide binding groove of the MHC molecule at the B and F pockets of the binding groove of an MHC I molecule. The ligand is preferably a ligand as depicted in Table S1, where Z is preferably the Abc of formula II. In another preferred embodiment, the ligand is a ligand as depicted in FIG. 1. For MHC I ligands, $n_2$ or $n_3$, or both, are preferably independently 0 or 1. In a preferred embodiment, $n_2$ or $n_3$, or both are preferably 1.

For MHC class II, the amino acid residues are preferably positioned to interact with at least two of the major pockets of the MHC class II peptide binding groove. The ligand preferably contains the amino acid residues of the core region at positions 1 and 9. The ligand is preferably a ligand as depicted in Table S7 where Abc is preferably the Abc of formula II. For MHC II ligands $n_2$ or $n_3$, or both, are preferably independently 0, 1, 2 or 3. In a preferred embodiment, $n_2+n_3$ is preferably 3 or 4. Preferably, $n_2+n_3$ is 3.

The MHC molecule can be an MHC class I, MHC class II, a non-classical MHC molecule or a functional part, derivative and/or analogue thereof. MHC II peptides with light sensitive conjugates have been produced among others in Grotenberg et al. (2007: The J. of Biol. Chem. Vol. 282:21425-21436). In a preferred embodiment the MHC molecule is an MHC I molecule. Preferably the MHC molecule is an HLA molecule. Preferably the MHC molecule is a soluble MHC molecule, preferably as described in D. N. Garboczi, D. T. Hung, D. C. Wiley (HLA-A2-peptide complexes: refolding and crystallization of molecules expressed in *Escherichia coli* and complexed with single antigenic peptides, *Proc. Natl. Acad Sci. U.S.A.* 1992 Apr. 15; 89(8):3429-33). The MHC molecule is preferably a human MHC molecule.

A functional derivative of an MHC molecule is a molecule that is not derived from nature, but that shares at least a peptide binding property with an MHC molecule in kind, not necessarily in amount. For instance, modified MHC molecules comprising one or more amino acid differences with natural MHC molecules, but that retain a peptide binding function, are functional derivatives in the context of this disclosure. Similarly, molecules comprising (part of) peptide binding domains from two or more MHC molecules and that are capable of binding a peptide are also considered functional derivatives. Modifications that are typically tolerated are those that are not in the peptide binding domains. Other mutations or modifications that are tolerated are in the variable domains of the peptide binding domains of MHC molecules. Such modifications typically alter the binding specificity of the MHC molecule (i.e., which peptide is bound). Such modifications are, therefore, also considered functional derivatives of MHC molecules of the disclosure.

Several molecules share the peptide binding properties of MHC molecules but have evolved to serve a different purpose in the cell. Such molecules are considered functional analogues of an MHC molecule of this disclosure. Domains that are involved in (poly)peptide binding can be combined with such domains from MHC molecules. MHC molecules or functional parts, derivatives and/or analogues thereof may further contain other parts that are not normally associated with MHC molecules. Such other parts may, for instance, comprise labels, tags, association and/or multimerization domains and other elements.

The technology of this disclosure can be used to specifically destabilize ligands bound to MHC molecules, or to functional parts, derivatives and/or analogues thereof. Destabilization of the MHC bound ligands then results in the generation of ligand-free MHC molecules without exposure to harsh conditions. The resulting ligand-free MHC molecules may then be used, either in the ligand-free form, or may be loaded with one or multiple ligands, peptide antigens of choice.

Thus, in a preferred aspect of this disclosure, an MHC molecule or a functional part, derivative and/or analogue thereof, comprises a peptide antigen (also referred to as ligand) in the peptide-binding groove of the MHC molecule or a functional part, derivative and/or analogue thereof. The Abc is preferably present in the peptide antigen as this warrants release of the peptide antigen from the otherwise unmodified MHC molecule or a functional part, derivative and/or analogue thereof. The resultant ligand-free MHC molecules may be used directly or be loaded with one or more other ligands, peptide antigens. To this end, the disclosure further provides a composition comprising an MHC molecule of the disclosure. Such a composition can be provided with a peptide antigen to be loaded onto the MHC molecule. Thus, further provided is a major histocompatibility complex (MHC) molecule or a functional part, derivative and/or analogue thereof, comprising a peptide antigen in the peptide-binding groove of the molecule and wherein the peptide antigen comprises the Abc. The composition can also comprise a further peptide. In a preferred embodiment, the further peptide is a peptide antigen capable of binding in the peptide-binding groove of the MHC molecule, i.e., a ligand for the MHC molecule. The further peptide may be added after the exposure to the reducing agent. It is preferred that the further peptide is present when the reducing agent is added to the composition. The peptide can take the place of the leaving fragments. The resultant MHC molecule or functional part, derivative and/or analogue thereof is thereby loaded with the further peptide. Thus, the composition contains the newly loaded MHC molecule (or functional part, derivative and/or analogue thereof) and fragments of the leaving peptide.

In another aspect, the disclosure provides a method for producing an MHC molecule or a functional part, derivative and/or analogue thereof, or an MHC molecule complex comprising a further peptide, comprising producing an MHC molecule of the disclosure, contacting the produced MHC molecule with a reducing agent and contacting the MHC molecule with an MHC peptide antigen. The MHC molecule of the disclosure is preferably an MHC molecule comprising a ligand in the peptide binding groove of the MHC molecule, whereby the ligand comprises an azobenzene (Abc) wherein at least one of the aromatic rings comprises an electron-donor group. The electron-donor group is preferably a hydroxyl in the ortho position relative to the azo-group. The azobenzene further comprises at least two amino acid residues separated by the azo-group of the Abc, and wherein the amino acid residues are positioned to interact with the peptide binding groove of the MHC molecule.

The reducing agent cleaves the Abc into smaller fragments. This allows the easy removal of the leaving peptide (or fragments thereof) from the MHC molecule or functional part, derivative and/or analogue thereof. Removal does not require harsh conditions and, thus, does not, or only minimally, interfere with the activity of the molecule. The free MHC molecule can be provided with a desired peptide. Using a method of the disclosure, it is possible to produce large amounts of MHC molecule having the leaving peptide. This preparation can subsequently be used to generate MHC molecules comprising a variety of different ligands (antigenic peptides) with a method of the disclosure. The contacting with the reducing agent and the contacting with the desired peptide can be performed in one step.

The disclosure further provides a method of detecting an MHC molecule comprising producing an MHC molecule according to a method of the disclosure and detecting the MHC molecule or the peptide in the peptide binding groove of the MHC molecule. This aspect is, for example, useful for diagnostic purposes. Binding can be detected in various ways, for instance, via T-cell receptor or antibody specific for the peptide presented in the context of the MHC molecule. Binding is preferably detected by detecting a label that is associated with the peptide or the MHC molecule. Labelling of the peptide can be done by tagging the peptide with a specific binding molecule such as biotin that can be subsequently visualized via, for instance, labelled streptavidin or analogues thereof. In a preferred embodiment, the peptide comprises the label. In this way, any peptide bound to the MHC molecule can be detected directly. Detection of binding is preferably done for screening purposes, preferably in a high throughput setting. Preferred screening purposes are screening for compounds that affect the binding of the peptide to the MHC molecule. For instance, test peptides or small molecules can compete with binding of the peptide to the MHC molecule. Competition can be detected by detecting decreased binding of the peptide. A preferred method for detecting binding of the peptide to the MHC molecule is measured by means of fluorescence anisotropy. In this way, manipulations of the sample wherein the binding is performed can be reduced. Reduction of sample manipulations is a desired property for high throughput settings. Other preferred means for detecting binding of the peptide are monitoring radioactivity or by monitoring binding of an MHC conformation-dependent binding body, preferably an antibody or a functional part, derivative and/or analogue thereof. Other preferred means include the use of a T-cell receptor specific for the combination of the peptide, MHC molecule. In a preferred embodiment, inhibition or enhancement of binding of the peptide to the MHC molecule is measured. In a preferred embodiment, the method is used for determining binding of the desired peptide in the presence of a test or reference compound.

The disclosure further provides an MHC molecule obtainable by a method of the disclosure. Further, the disclosure provides a composition comprising an MHC molecule according to the disclosure, wherein the composition comprises an MHC molecule comprising a peptide comprising an Abc and an MHC molecule comprising a further peptide.

The disclosure further provides a complex comprising at least two MHC molecules of the disclosure. A complex comprising at least two MHC molecules of the disclosure is preferably a dimer, a trimer, a tetramer, a pentamer or a dextramer of MHC molecules. In a preferred embodiment, the complex is a tetramer. The term "complex" as used herein refers to a protein complex wherein two or more MHC molecules are physically linked to each other and are functional. The term does not refer to structures as inclusion bodies or precipitates consisting essentially of denatured or otherwise non-functional MHC molecules. The term "complex" typically refers to a multimer of two or more MHC molecules that are in solution. Association of two or more MHC molecules via a solid surface is typically not referred to as a complex but as a solid surface. MHC molecules can also be associated to each other by coupling them to, for instance, a polymer. Such associations are also captured under the term complex, unless the polymer is in the form of a gel or other solid surface. In the latter case, the association is referred to as a solid surface comprising two or more MHC molecules. A solid surface can comprise a complex of the disclosure as also indicated hereinbelow. A preferred complex is an MHC tetramer. Complexes such as dimers, trimers, tetramers and the like have a higher affinity for the particles and cells carrying T-cell receptors than the single MHC molecule. Such complexes are, therefore, important tools in the analysis of T-cell populations. The disclosure, thus, further provides a complex comprising at least two MHC molecules of the disclosure. Means and methods for producing complexes containing two, three, four and five MHC molecules or functional parts, derivatives and/or analogues thereof are available in the art. Thus, this disclosure further provides a complex comprising two, three, four or five MHC molecules of the disclosure or functional parts, derivatives and/or analogues thereof. In a preferred embodiment, the complexes comprise MHC molecules having the same T-cell receptor specificity. However, this need not always be the case. Considering the relative ease with which MHC molecules can be provided with different peptides using a method of the disclosure, complexes comprising two or more T-cell receptor specificities are within the scope of this disclosure. The disclosure further provides a solid surface comprising at least two MHC molecules or complexes of the disclosure. In a preferred embodiment, the solid surface is provided with a complex of the disclosure, preferably a complex comprising a single peptide, or multiple peptides associated with the same disease or pathogen. The solid surface can be a bead or a microchip. The solid surface can be any solid material. The solid surface is preferably a biochemically inert surface such as a glass, plastic or metallic surface. The surface can also be a polymer surface, such as a gel. The solid surface is typically essentially two-dimensional. However, three-dimensional surfaces such as gels are within the scope of the disclosure. The surface may have undergone pre-treatment prior to coating of the MHC molecule, composition or complex of the disclosure. Such pre-treatment may include, but is not limited to, polyacrylamide film-coating as described by Soen et al. (*PLoS Biology* 2003, Vol. 1:429-438). The disclosure further provides a microarray comprising an MHC molecule, composition or complex of the disclosure. Means and methods for producing a (micro)array comprising an MHC molecule complex coupled to antigenic peptide is described by Soen et al. mentioned above. The artisan is referred to the reference for guidance as to the generation of a (micro)array of the disclosure.

The disclosure further provides a composition comprising an MHC molecule of the disclosure and/or a complex of the disclosure and an MHC peptide antigen.

The disclosure further provides a method of producing an MHC molecule comprising:

producing an MHC molecule of the disclosure;
contacting the produced MHC molecule with a reducing agent; and
contacting the MHC molecule with an MHC peptide antigen.

The two contacting steps are preferably performed by providing a sample comprising the MHC molecule with the MHC peptide antigen and the reducing agent. It is preferred that the MHC peptide antigen is present when the reducing agent is added. An MHC molecule that does not contain a peptide in the peptide binding groove can be unstable under certain conditions. To avoid such, it is preferred that the MHC peptide antigen is added prior to addition of the reducing agent. Preferably, one MHC peptide antigen is added per reaction, but this is not essential. It is within the scope of the disclosure to add more than one different MHC peptide antigen per reaction.

The reducing agent can be any agent capable of reducing the azo group in an Abc of the disclosure. A preferred reducing agent is dithionite, preferably sodium dithionite. Other reducing agents can also be used. It is preferred that the reducing agent is biocompatible. A non-limiting example is $SnCl_2$ using 0.1 M HCl. Dithionite is preferred as it is milder than the indicated $SnCl_2$ treatment. The artisan appreciates that the reducing agent can be varied depending on the electron-donor group and/or the position of the electron-donor group relative to the azo-group.

The disclosure further provides a method of detecting an MHC molecule comprising producing an MHC molecule of the disclosure and detecting the MHC molecule. In a preferred embodiment, the MHC molecule, a peptide in the peptide binding groove of the MHC molecule, or both, comprise a label.

The disclosure further provides a solid surface comprising an MHC molecule or complex of the disclosure.

The disclosure further provides an azobenzene of formula I

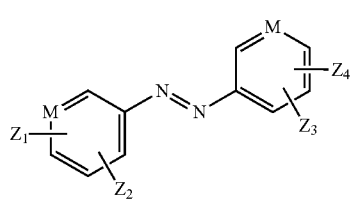

Formula I wherein
- at least one of the aromatic rings comprise an electron-donating group;
- M is independently C, S, N or O;
- Z1 and Z4 each comprise an amino acid residue positioned to interact with the peptide binding groove of an MHC molecule;
- Z2 and Z3 are independently H, hydroxyl, carboxy, keto, or a linear or branched $C_1$-$C_{10}$ alkyl, optionally substituted with an oxy, hydroxyl, nitrogen, nitroxy, sulhydryl or sulfide group.

An azobenzene of the disclosure preferably comprises a structure of formula IV

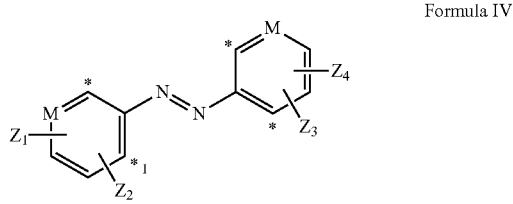

Formula IV wherein
- "*" indicates that the azobenzene has at least one hydroxyl in the ortho position relative to the azo group; the hydroxyl is preferably in the position *1 as indicated in the general formula IV;
- M is independently C, S, N or O;
- Z1 and Z4 each comprise an amino acid residue positioned to interact with the peptide binding groove of an MHC molecule;
- Z2 and Z3 are independently H, hydroxyl, carboxy, keto, or a linear or branched $C_1$-$C_{10}$ alkyl, optionally substituted with an oxy, hydroxyl, nitrogen, nitroxy, sulhydryl or sulfide group.

The "*" indicates the four ortho positions for the at least one hydroxyl. Not all four positions indicated by the "*" have to contain a hydroxyl. Only one of the four positions needs to contain a hydroxyl. In a preferred embodiment, the Abc contains one hydroxyl in the ortho position relative to the azo group. In a preferred embodiment, the hydroxyl group is in the position *1 as indicated in the general formula IV. The preferred position of the hydroxyl indicated by "*1" is also the preferred position for the hydroxyl group in the azobenzene of the disclosure, such as but not limited to, the azobenzene of formulas I, II and III.

In the structural formulas, the indicators "*," "M," "Z1-Z4," "A-D," "X," "Y," "n1-n4" and other indicators have the same meaning. So, in the description where an indicator is defined, such definition applies the same for the indicator in any of the respective formulas. The same holds for the $C_{1-2}$ alkyl group between a benzene ring and an amino acid residue.

The disclosure further provides an azobenzene of the disclosure for use in the production of an MHC molecule comprising a peptide in the peptide binding groove of the MHC molecule.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A-5K (Figure S1) Mass spectrometry (MS) analysis of the synthesized Abc ligands by LC-MS IT-TOF. The peptides were first separated by liquid chromatography (LC) on a C18 column prior to the measurement of its mass to charge ratios (m/z). Details of the Abc ligands are shown in Table S1. The reference to —Z— indicates Z in the presence of an Abc of formula II.

FIG. 5A: Conditional ligand: AIF-Z-TK; Empirical formula: C43H59N9O9;
  Exact Mass: 845.44; Molecular Weight: 845.98
  Peak #1; Retention Time: 11.520 minutes; Base Peak m/z: 846.3542;
  Base Peak Intensity: 937599; Polarity: Pos FIG. 5B: Conditional ligand: AIM-Z-YPK; Empirical formula: C49H68N10O10S;
  Exact Mass: 988.48; Molecular Weight: 989.19
  Peak #2; Retention Time: 9.033 minutes; Base Peak m/z: 495.2475;
  Base Peak Intensity: 1413471; Polarity: Pos FIG. 5C: Conditional ligand: QVPL-Z-YK; Empirical formula: C51H71N11O11;
  Exact Mass: 1013.53; Molecular Weight: 1014.19
  +ESI Scan; 15 scans: 6.088-6323 minutes Frag=180.0V; Polarity: Pos FIG. 5D: Conditional ligand: KTF-Z-PK; Empirical formula: C45H62N10O9;
  Exact Mass: 886.47; Mol. Wt.: 887.04
  Peak #: 1; Retention Time: 10.733 minutes; Base Peak m/z: 887.3648;
  Base Peak Intensity: 658640; Polarity: Pos FIG. 5E: Conditional ligand: FLPS-Z-SV; Empirical formula: C46H61N9O11;
  Exact Mass: 915.45; Molecular Weight: 916.05
  Peak #: 2; Retention Time: 12.513 minutes; Base Peak m/z: 916.4301;
  Base Peak Intensity: 6800116; Polarity: Pos FIG. 5F: Conditional ligand: LLF-Z-YV; Empirical formula: C50H64N8O9;
  Exact Mass: 920.48; Molecular Weight: 921.11
  Peak #: 2; Retention Time: 14.293 minutes; Base Peak m/z: 921.4783;
  Base Peak Intensity: 2512246; Polarity: Pos, Event FIG. 5G: Conditional ligand: NLVP-Z-TV; Empirical formula: C44H64N10O11;
  Exact Mass: 908.48; Molecular Weight: 909.05
  Peak #: 2; Retention Time: 12.793 minutes; Base Peak m/z: 909.4549;
  Base Peak Intensity: 1161661; Polarity: Pos FIG. 5H: Conditional ligand: NLVP-Z-VATV; Empirical formula: C52H78N12O13;
  Exact Mass: 1078.58; Molecular Weight: 1079.27
  Peak #: 2; Retention Time: 13.300 minutes; Base Peak m/z: 1079.5823;
  Base Peak Intensity: 1070704; Polarity: Pos FIG. 5I: Conditional ligand: GLS-Z-RL; Empirical formula: C38H57N11O9;
  Exact Mass: 811.4341; Molecular Weight: 811.9275
  Peak #: 1; Retention Time: 9.613 minutes; Base Peak m/z: 406.7002;
  Base Peak Intensity: 3287573; Polarity: Pos FIG. 5J: Conditional ligand: FAP-Z-AL; Empirical formula: C41H52N8O8;
  Exact Mass: 784.39; Molecular Weight: 784.91
  Peak #: 1; Retention Time: 9.693 minutes; Base Peak m/z: 785.3885;
  Base Peak Intensity: 582117; Polarity: Pos FIG. 5K: Conditional ligand: FAP-Z-KL; Empirical formula: C44H59N9O8;
  Exact Mass: 841.45; Molecular Weight: 842.01
  Peak #: 2; Retention Time: 9.253 minutes; Base Peak m/z: 421.7008;
  Base Peak Intensity: 2788083; Polarity: Pos FIG. 6 (Figure S2): Binding of Abc ligands to HLA-A*02:01 and H2-K$^b$. Photocleavable ligands on Panel a) A*02:01 and Panel b) K$^b$ molecules were peptide-exchanged with either previously identified peptide antigens (1, 9, 12 and 18) or Abc ligands (13 to 17, 19 and 20) following UV irradiation. Peptide ligands that can bind to the MHC will stabilize the MHC complex. ELISA was used to detect intact MHC molecules before UV irradiation (—UV), after UV irradiation in the absence (+UV) or in presence of binding peptides.

FIG. 7 (Figure S3): In vitro refolding and biotinylation of HLA-A*11:01, A*02:01 and H2-K$^b$ containing Abc ligands (4, 17 and 20 respectively). Panel a) The refolded MHC complexes were purified using S200 size exclusion chromatography. Fractions corresponding to approximately 45 kDa were collected as indicated in red. Panel b) Gel shift SDS-PAGE was performed to assess the proportion of biotinylated MHC molecules. Purified MHC molecules yielded two distinct bands corresponding to the heavy chain (~33 kDa) and beta 2m (~12 kDa). In the presence of soluble streptavidin, the biotinylated heavy chains bind to streptavidin forming complexes of high molecular size. IB:HC and IB: beta 2m refers to the heavy chain and beta 2m extracted from E. coli inclusion bodies, respectively.

FIG. 8 (Figure S4): Crystal structure of HLA-A*11:01 (grey) in complex with the Abc ligand, AIM-Z-YPK (cyan). Panel a) Side view of the complex in cartoon format showing that the azobenzene moiety protrudes from the peptide binding cleft of the MHC. Panel b) Top-down view in cartoon format showing the orientation that the Abc peptide resides in the binding cleft. Panel c) Representation of the complex in its side surface view to show the depth of the ligand binding in the cleft. Panel d) Top-down surface view shows that the ligand fits into the pockets of the MHC binding cleft. Z is the Abc of formula II.

FIG. 9 (Figure S5): Interactions between AIM-Z-YPK and residues in the binding groove of HLA-A*11:01. Panel a) Top-down zoomed-in view of the HLA-A*11:01 peptide binding cleft. HLA-A*11:01 residues that contact the Abc ligand are highlighted as grey sticks. Electron density omit map (dark grey mesh) of the AIM-Z-YPK ligand (cyan). Panel b) Interaction map depicting the contacts (represented by black dotted lines) made between the Abc ligand (amino acid in blue azobenzene moiety in red) and HLA-A*11:01 residues (black). Numbers representing bond distances are in A. Z is the Abc of formula II.

FIG. 10 (Figure S6): Alternate conformations of the AIM-Z-YPK ligand. The normal "cis" binding confirmation of the Abc ligand (left) and the "trans" cross-linking conformation (right), of the two complexes in the asymmetric unit are shown. Z is the Abc of formula II.

FIG. 11 (Figure S7): HLA-A*11:01 molecules with AIM-Z-YPK ligand bound in alternate conformations give rise to two different molecular species. The canonical "cis" binding conformation of the ligand results in HLA-A*11:01 monomeric complexes and the noncanonical "trans" binding conformation results in HLA-A*11:01 dimeric complexes. Panel a) The two species yielded two fractions in size exclusion chromatography. Panel b) Repeated size exclusion chromatography with the separated fractions (fractions 1, left and 2, right) shows that the species did not interconvert in solution. Panel c) Particle size of the HLA-A*11:01:AIM-Z-YPK species were determined using dynamic light scattering to be 171 Å and 98 Å in diameter for fraction 1 (left) and 2 (right), respectively. Z is the Abc of formula II.

FIG. 12 (Figure S8): Crystal structure of HLA-A*02:01 (grey) in complex with the Abc peptide, GLS-Z-RL (orange). Panel a) The side view of the structure reveals that the Abc moiety of GLS-Z-RL ligand sits lower in the MHC peptide-binding cleft and is not as exposed as in the HLA-A*11:01 complex. Panel b) 90 degree flip around the x-axis to show the top-down view in cartoon format of the peptide binding in the cleft. Panel c) View of Panel a) in surface format. Panel d) View of Panel b) in surface format. Z is the Abc of formula II.

FIG. 13 (Figure S9): Interactions between GLS-Z-RL and residues in the binding groove of HLA-A*02:01. Panel a) Top-down zoomed-in view of the HLA-A*02:01 peptide binding cleft. Abc ligand-interacting residues of HLA-A*02:01 are highlighted as grey sticks. Electron density omit map (dark grey mesh) of the AIM-Z-YPK ligand (orange). The aromatic rings of the azobenzene moiety are not in the same plane due to a slight twist around the N=N bond. Panel b) Interactions (represented by black dotted lines) made between the Abc ligand (amino acid in orange, azobenzene moiety in red) and HLA-A*02:01 residues (black) are shown in an interaction map. Z is the Abc of formula II.

FIG. 14 (Figure S10): MHC stability ELISA of sodium dithionite-mediated peptide-exchanged HLA-A*02:01 and H2-$K^b$ molecules. Panel a) A*02:01 refolded in vitro with 17 were peptide-exchanged with two A*02:01-restricted epitopes (12 and 21) and an A*11:01-restricted epitope (1) in the presence of 5 to 20 mM sodium dithionite. Panel b) Similar to Panel a), refolded $K^b$ molecules bearing 20 were peptide-exchanged with two $K^b$-restricted epitopes (18 and 22) and an $L^d$-restricted epitope (9). Negative controls with no peptides added (−) to the MHC molecules were included.

FIG. 15 (Figure S11): Preferential cleavage of Abc ligands by sodium dithionite. Panel a) A mixture containing 9 and 17 at 1:1 molar ratio (0.123 mM each) and varying concentrations of L-Glutathione oxidized (0 to 125 mM) were incubated in the absence (empty bars) or presence of 2.5 mM sodium dithionite (filled bars) for 5 minutes. Panel b) Similar to Panel a), peptide mixture of 9 and 17 (0.123 mM each) were added to varying concentrations of L-Cystine (0 to 125 mM) prior to treatment with 2.5 mM sodium dithionite. Data are represented as the ratio of the intact Abc ligand 17 to dithionite-resistant 9 detected in LC-MS after sodium dithionite treatment.

FIG. 16 (Figure S12): Flow cytometric analysis on the viability of sodium dithionite-treated $CD8^+$ T-cells. Freshly isolated human PBMCs were incubated with sodium dithionite ranging from 1 mM to 100 mM to assess cellular toxicity of sodium dithionite. Cells were treated for 1 hour (top row), 1 hour followed by rested overnight in fresh culture media (middle row) or 16 hours (bottom row) prior to staining with anti-CD8 antibodies, Annexin V and LIVE/DEAD® viability dye. Data represented above are based on $CD8^+$ cells. Numbers in each plot are expressed as a percentage of total $CD8^+$ population.

FIG. 17 (Figure S13): Detection of antigen-specific $CD8^+$ T-cells using A*02:01 tetramers generated from UV-mediated peptide exchange or sodium dithionite-mediated peptide exchange. Freshly isolated peripheral blood mononuclear cells from an A*02:01-positive volunteer were stimulated with A*02:01 epitopes EBV LMP2426-434 (upper row) and CMV pp65495-503 (lower row). A*02:01-EBV LMP2426-434 (columns 1 and 4), A*02:01-CMV pp65495-503 (columns 2 and 5) and A*02:01-Abc (column 3) tetramers were used to perform tetramer staining 14 days post in vitro stimulation. Number in each plot represents tetramer-positive cells expressed as a percentage of total $CD8^+$ T-cells. Plots in columns 1 to 2 and columns 3 to 5 are tetramer staining performed using UV-derived tetramers and Abc-derived tetramers, respectively.

FIG. 18 (Figure S14): Detection of antigen-specific $CD8^+$ T-cells using H2-$K^b$ MHC tetramers generated from UV-mediated peptide exchange or sodium dithionite-mediated peptide exchange. Freshly isolated splenocytes from naïve and OTI-TCR transgenic C57/BL6 mice were mixed in 1:1 ratio. $K^b$—$OVA_{257-264}$ (columns 1 and 4), $K^b$-$Tgd057_{57-64}$ (columns 2 and 5) and $K^b$-Abc (column 3) tetramers were used to detect OT1 cells from the splenocyte mixtures. Numbers in each plot represent tetramer-negative (left) and tetramer-positive (right) $CD8^+$ splenocytes expressed as a percentage of total splenocyte mix. Plots in columns 1 to 2 and columns 3 to 5 are tetramer staining performed using UV-derived tetramers and Abc-derived tetramers, respectively.

FIG. 19: Peptide binding of $MBP_{85-99}$ (yellow) to HLA-DR2 (blue) molecule. 15 residues (P-4 Glu to P11 Arg) of the MBP peptide were shown with peptide side chains of the P1 Val, P4 Phe, P6 Asn and P9 Thr occupying pockets within the peptide binding groove of the MHC molecule. (Smith et al., *J. Exp. Med.* 1998, 188:1511-1520.) This figure is not part of the manuscript.

FIG. 21: Abc-ligands for HLA-A*02:01.

FIG. 22: Peptide exchange of known non-(CTELKLSDY and IVTDFSVIK); intermediate-(SLENFRAYV; ALQLLLEV and VMLRWGVLA) and high-affinity binders (NLVPMVATV; GILGFVFTL, SLYNTVATL and NMLSTVLGV) to HLA-A*02:01 using HLA-A*02:01-ILKZGV (Panel A) or HLA-A*02:01-ILKZKV (Panel B) and Na2S2O4-induced peptide exchange (values are the mean±SD of two independent experiments) or HLA-A*02:01-KILGFVFJV and UV-induced peptide exchange (Panel C). The presence of intact HLA complex was determined by MHC stability ELISA. The measured absorbances at 414 nm were evaluated relative to that of the high affinity binder NLV which was put to 100%.

DETAILED DESCRIPTION

Examples

Materials and Methods

Abc Ligand and Antigenic Peptide Synthesis

Figure 1:
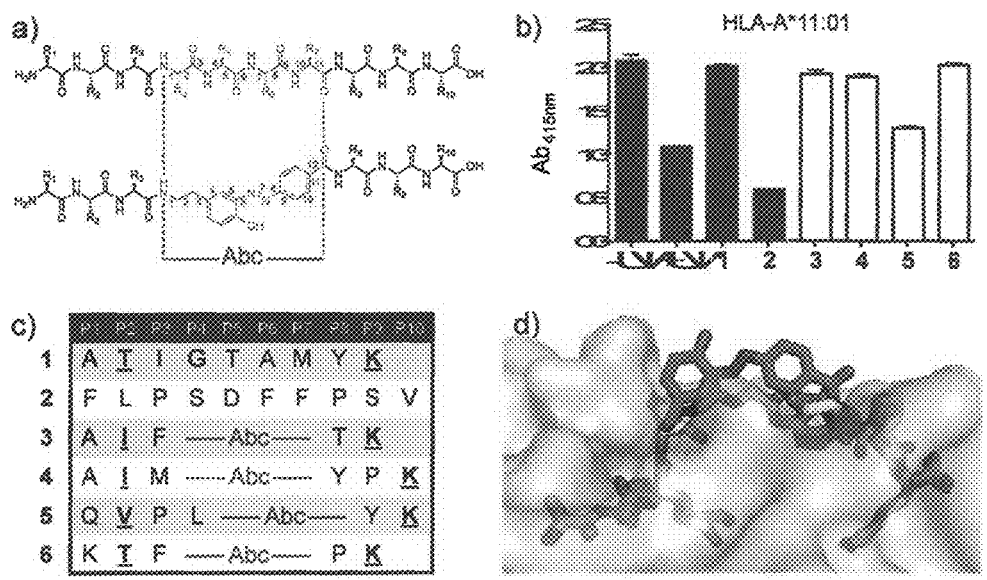
FIG. 1: Design of HLA-A*11:01-restricted Abc ligands. Panel a) Replacement of four amino acids residues (11 bond lengths) with an azobenzene-containing (Abc) tetrapeptide isostere (12 bond lengths). Panel b) MHC stability ELISA of UV-sensitive A*11:01 molecules peptide-exchanged with A*11:01-restricted epitope (1), A*02:01-restricted epitope (2) and A*11:01-restricted Abc ligands (3 to 6) upon UV irradiation. MHC molecules before (−UV) and after (+UV) UV irradiation in the absence of rescue peptides were included as controls. Panel c) Sequences of the epitopes (1 and 2) and newly synthesized Abc ligands (3 to 6) that were used in Panel b). The position of the Abc moiety in the parent peptides is indicated in red. Anchor residues of the peptides are underlined. Panel d) Overlay of crystal structures of 4 (cyan) (PDB reference ID: 4BEO, this work) and its parent peptide (yellow) (PDB reference ID: 2HN7) in an A*11:01 molecule (grey).

The azobenzene-containing (Abc) MHC ligands were manually constructed by standard Fmoc-based solid-phase peptide synthesis. Fmoc-protected amino acids and Wang-based resins were purchased from Advanced ChemTech.

The azobenzene linker was constructed as described (Verhelst et al., 2007). All other chemicals were purchased from Sigma-Aldrich. Deprotection and coupling of amino acids was carried out manually in a rotating glass reactor vessel at 0.2 mmol scale. For each peptide, the MBHA Resin HS, 100-200 mesh, 1% DVB (105 mg, 0.2 mmol, 1 equiv) was allowed to swell for 12 minutes in N-methyl-2-pyrolidinone (NMP). Installation of HMPB linker (120 mg, 0.5 mmol, 2.5 equiv) was accomplished using hydroxybenzotriazole (HOBT) (68 mg, 0.5 mmol, 2.5 equiv), benzotriazol-1-yl-oxytripyrrolidinophosphonium hexafluorophosphate (PyBOP) (260 mg, 0.5 mmol, 2.5 equiv) and N,N-diisopropylethylamine (DIPEA) (246 µL, 1.5 mmol, 7.5 equiv) in 4 ml NMP. The HMPB-linked resin was washed for 12 minutes in NMP, followed by 12 minutes in dichloromethane (DCM). The first amino acid (0.8 mmol, 4 equiv) was coupled using N,N-diisopropylcarbodiimide (DIC) (124 µl, 0.8 mmol, 4 equiv), 4-dimethylaminopyridine (DMAP) (4 mg, 0.033 mmol, 0.165 equiv) in 4 ml DCM. The resin was then washed in DCM for 12 minutes, followed by 12 minutes in NMP. The amino acid/azobenzene linker was Fmoc-deprotected for 15 minutes using a solution of 20% piperidine in NMP. Following amino acid couplings were carried out using HOBT (108 mg, 0.8 mmol, 4 equiv), PyBOP (416 mg, 0.8 mmol, 4 equiv) and DIPEA (392 µl, 2.4 mmol, 12 equiv) in 4 ml NMP. Azobenzene linker (204 mg, 0.4 mmol, 2 equiv) coupling was carried out twice using PyBOP (208 mg, 0.4 mmol, 2 equiv) and DIPEA (196 µl, 1.2 mmol, 6 equiv) in 2 ml NMP. A Kaiser test (Kaiser et al., 1970) was used to monitor reaction completeness. Stepwise deprotection and coupling of the appropriate amino acids or azobenzene linker furnished the desired peptide on-resin. The peptides were cleaved, and simultaneously deprotected from dried resin using 5 ml trifluororoacetic acid (TFA) solution containing 2.5% distilled water and 2.5% triisopropyl silane (TIS) over 24 hours. The peptide solution was precipitated in cold diethyl ether, and dried under vacuum. The peptide identities were confirmed by IT-TOF LC/MS analysis (Shimadzu).

Cleavage of Abc Ligands with Sodium Dithionite

Abc ligand and IPAAAGRFF were mixed at 1:1 molar ratio (0.123 mM each) and incubated in the presence of 1 mM, 2.5 mM or 5 mM freshly prepared sodium dithionite (in 200 mM phosphate buffer, pH 7.4). The reactions were allowed to proceed for 1 to 5 minutes until quenched using ZipTipC18 (Milipore) to extract the peptides from the sodium dithionite solution. The peptides were then eluted in 0.1% trifluoroacetic acid containing 5% acetonitrile and analyzed on IT-TOF LC/MS (Shimadzu).

In Vitro Folding and Purification of MHC Complexes

MHC molecules were generated as described previously (Garboczi et al., 1992). Genes encoding human β2-microglobulin and luminal portion of HLA-A*11:01, A*02:01 and H2-K$^b$ engineered with a C-terminal BirA recognition sequence were cloned into pET-28a (+) vector (GenScript). The plasmids were transformed and overexpressed in E. coli BL21-induced by 1 mM isopropyl β-D-thiogalactopyranoside. The expressed proteins were extracted and purified from the inclusion bodies under reducing conditions and solubilized in 8 M urea. In vitro refolding of the MHC molecules was carried out with at least ten-fold molar excess of either UV-cleavable or Abc ligands for 24 to 36 hours. The proteins were dialyzed into 20 mM Tris (pH8.0), biotinylated in vitro by recombinant BirA and purified using S200 size exclusion chromatography. Biotinylated MHC molecules were conjugated with Streptavidin-PE (Invitrogen) at 4:1 molar ratio to form MHC tetramers. For MHC molecules used in crystallography, refolding and purification were carried out in a similar fashion with the exception that unbiotinylated constructs were used. Also, the proteins purified from size exclusion chromatography were further subjected to ion exchange chromatography on a Mono Q column in 20 mM Tris (pH 8.0) and eluted over a gradient of increasing salt concentration with 20 mM Tris (pH 8.0), 1 M NaCl. For both HLA-A*11:01 and HLA-A*02:01, the proteins eluted at approximately 100-150 mM NaCl.

Peptide Exchange Conditions on MHC Monomers and Tetramers

MHC monomers used for MHC stability ELISA were peptide-exchanged in the presence of 100-fold molar excess of peptide ligands. For photocleavable MHC monomers, preparations of 500 nM MHC monomers in PBS were subjected to 365 nm longwave UV irradiation on ice for 15 minutes using UVP CL-1000L Ultraviolet cross-linker (UVP), followed by the addition of 50 µM peptide ligands and 1-hour incubation on ice. For Abc MHC monomers, preparations containing 500 nM MHC monomers, 50 µM peptide ligands and 5 to 20 mM sodium dithionite in 50 mM HEPES (pH 7.4) were incubated for 30 minutes on ice. To stain antigen-specific CD8$^+$ T-cells, photocleavable MHC tetramers were diluted to 40 µg/ml with cold PBS containing 200 µM peptides, subjected to 365 nm longwave UV irradiation on ice for 15 minutes and followed by 1-hour incubation on ice. 40 µg/ml Abc MHC tetramers were incubated with 10 mM sodium dithionite in 50 mM HEPES (pH 7.4) containing 200 µM peptides and followed by 30-minute incubation on ice. After incubation, all MHC monomers and tetramers were further incubated for 1 hour at 37° C. with shaking at 850 rpm and were centrifuged at 16,000×g, 4° C. for 10 minutes prior to use.

MHC Stability ELISA

Assessment of ABC ligand binding to MHC molecules and optimization of ABC peptide exchange conditions were performed using an established protocol (Rodenko et al., 2006). Briefly, wells of a 384-well microplate (Corning) coated overnight at room temperature (RT) with 50 µl of 2 µg/ml streptavidin in PBS were washed and treated with 100 µl of 2% BSA in PBS for 30 minutes at RT. The 2% BSA was discarded and 25 µl of 20 nM peptide-exchanged MHC was added to each well and incubated on ice for 1 hour. Wells were then washed and incubated with 25 µl 1 µg/ml HRP-conjugated anti-jβ2m antibodies (Clone D2E9, Abcam) on ice for 1 hour. Subsequently, wells were washed and developed with 25 µl of ABTS solution (Invitrogen) for 10 to 15 minutes at RT. The development is quenched by the addition of 12.5 µl of 0.01% sodium azide in 0.1 M citric acid. Absorbance was measured at 415 nm using Spectramax M2 microplate reader (Molecular Devices). Each washing procedure involves rinsing the wells four times with 100 µl of 0.05% TWEEN® 20 in PBS. Samples were measured in quadruplicates.

Cells and MHC Tetramer Staining

Fresh whole blood was obtained from A*11:01 and A*02:01-positive volunteers. Isolation of PBMCs from these samples was performed via Ficoll-Paque density-gradient centrifugation. The isolated PBMCs were frozen for later staining without stimulation or were cultured in RPMI 1640 containing 2.05 mM L-glutamine (Invitrogen) supplemented with 40 µM 2-mercaptoethanol (Gibco), 100 IU/ml penicillin/streptomycin (Invitrogen) and 5% pooled human AB serum (Invitrogen) at 37° C., 5% $CO_2$. Briefly, PBMCs were stimulated with peptides at 10 µg/ml. 25 U/ml interleukin-2 (IL-2) (R&D systems) was added to the culture 2 days post-peptide stimulation. Half medium change was carried out and 25 U/ml IL-2 was supplemented every 2 to 3 days from 5 to 14 days post-stimulation.

Mouse splenocytes were extracted from spleens of naïve and OTI-TCR transgenic C57/BL6 mice using conventional splenocyte extraction protocol. Briefly, spleen meshed and homogenized in cold PBS was passed through a cell strainer. The resultant cells were washed with cold PBS and treated with 3 ml of RBC lysis buffer (pH 7.4) containing 155 mM $NH_4Cl$, 10 mM $KHCO_3$ and 0.1 mM EDTA for 2 minutes. Finally, the cells were washed twice with 10 ml of cold PBS and resuspended in 5 ml of cold PBS.

Cells were first stained with cell viability LIVE/DEAD® fixable near-IR stain (Molecular Probes®) prior to tetramer staining. Subsequently, cells were washed with PBS and incubated with 80 nM peptide exchanged PE-conjugated MHC tetramers on ice for 20 minutes. Cells from A*11:01-positive donor were stained with 200 nM MHC tetramers instead. All PBMCs and murine splenocytes were stained with anti-human CD8 (Clone RPA-T8, BD biosciences) or anti-murine CD8 (Clone 53-6.7, BD biosciences) Pacific Blue™ antibodies for 15 minutes, respectively. Cells were then washed again with PBS and fixed with 1% paraformaldehyde in PBS. Flow cytometry data were acquired on BD LSRII flow cytometer and analyzed using FlowJo (Tree Star).

Cell Viability Assay $10^6$ freshly isolated PBMCs from healthy volunteers were incubated in 1 ml RPMI 1640 culture media containing HEPES-buffered 1 mM to 100 mM sodium dithionite (pH 7.4) at 37° C., 5% $CO_2$. After 1-hour or 16-hour incubation, the cells were immediately assessed for cell viability or rested overnight in fresh media (for 1-hour treatment only). The cells were harvested, washed with PBS twice and stained with cell viability LIVE/DEAD® fixable near-IR stain (Molecular Probes®). The cells were then washed again with PBS and stained with anti-human CD8 (Clone RPA-T8; BioLegend) Brilliant Violet 421™ antibodies for 15 minutes. Thereafter, the cells were washed once with PBS and once with 1× Annexin V binding buffer (10 mM HEPES, pH 7.4; 140 mM NaCl; 2.5 mM $CaCl_2$) prior to incubation with Annexin V FITC (eBioscience) for 10 minutes. The stained cells were immediately analyzed on BD LSRII flow cytometer and data were processed using FlowJo (Tree Star).

Mass Spectrometry Analysis of Epitope Modification

50 μM of Influenza A $MP_{13-21}$ and EBV $BMLF-1_{259-267}$ peptides were incubated with 10 mM $Na_2S_2O_4$ in 50 mM HEPES (pH 7.4) or 0.3 mM $NaIO_4$ in PBS at RT for 2 hours. After which, the peptides were extracted from the buffer using ZipTipC18 (Milipore) and loaded on LC/MS IT-TOF (Shimadzu) for analysis. 50 μM peptides in PBS were used as a control.

Competition Assay for Cleavage of Abc Ligands and Disulfide Bonds

GLS-Z-RL and IPAAAGRFF (0.123 mM each) were mixed with 2.5 mM, 25 mM or 125 mM L-Glutathione oxidized (Sigma-Aldrich) or L-Cystine (Sigma-Aldrich) and incubated with 2.5 mM freshly prepared sodium dithionite (in 200 mM phosphate buffer, pH 7.4). After 5 minutes, the peptides were extracted from the L-Glutathione oxidized or L-Cystine, and sodium dithionite mixture using ZipTipC18 (Milipore). Elution of the peptides was carried out in 0.1% trifluoroacetic acid containing 5% acetonitrile prior to analysis on IT-TOF LC/MS (Shimadzu).

X-Ray Structures of HLA-A*11:01:AIM-Z-YPK and HLA-A*02:01:GLS-Z-RL Complexes

X-ray crystallographic studies were performed to determine the molecular details in which class I MHC molecules bind to the azobenzene-containing peptide.

Crystallization Conditions for HLA-A*11:01:AIM-Z-YPK and HLA-A*02:01:GLS-Z-RL Complexes Crystals for HLA-A*11:01:AIM-Z-YPK were grown at room temperature using the sitting drop, vapor-diffusion method with a well solution of 15% (w/v) PEG4000, 0.2 M ammonium sulfate, 0.1 M tri-sodium citrate (pH 5.6). Crystals for HLA-A*02:01:GLS-Z-RL were grown at room temperature using the sitting drop method with a well solution of 20% (w/v) PEG4000, 10% (w/v) isopropanol, 0.1 M HEPES pH 7.5. Crystals were harvested and frozen rapidly in liquid nitrogen for data collection.

X-Ray Data Collection and Structure Refinement of HLA-A*11:01:AIM-Z-YPK and HLA-A*02:01:GLS-Z-RL Complexes X-ray diffracted intensities for HLA-A*11:01:AIM-Z-YPK were collected at 100 K using a FRE generator at the Biopolis Shared Facilities, Singapore, with a R-AXIS IV++ imaging plate detector from Rigaku. The data was collected at X-ray wavelength of 1.54 Å. X-ray data for HLA-A*02:01:GLS-Z-RL were collected at 100 K using the X06DA beamline (X-ray wavelength of 1.0 Å) at the Swiss Light Source with a Pilatus detector. Diffraction data (Table S3 for A*11:01 and Table S5 for A*02:01) for both HLA complexes were integrated with Mosflm and intensities were scaled with SCALA (Evans, 2006; Leslie, 1992). The structures were solved by molecular replacement in the program MOLREP (Vagin and Teplyakov, 2000), using the HLA-A*11:01 structure with PDB code 2HN7 (Blicher et al., 2006) or the HLA-A*02:01 structure with PDB code 3V5H, as search probe for HLA-A*11:01 and HLA-A*02:01, respectively. For HLA-A*11:01, refinement was carried out with REFMAC and BUSTER (Murshudov et al., 1997; Smart et al., 2012), with a final refinement being carried out on REFMAC. For HLA-A*02:01, the structure was refined initially with REFMAC, followed by final refinement rounds with Buster. Validation of the models and the x-ray data were checked with MOLPROBITY (Davis et al., 2007), and figures were generated using PyMOL (Delano, 2002). The coordinates and structure factors (code 4BEO for the HLA*A11:01 complex and 4BLH for the HLA*A02:01 complex) have been deposited in the Protein Data Bank.

The Crystal Structure of HLA-A*11:01:AIM-Z-YPK and HLA-A*02:01:GLS-Z-RL Complexes X-ray crystallographic studies were performed to determine the molecular details of the interaction between class I MHC molecules and the azobenzene-containing peptide.

Overall Description.

The X-ray structure of the HLA-A*11:01 molecule in complex with the azobenzene-containing peptide was determined to 2.43 Å resolution (Table S3 and Figure S4). The model contains residues 1-274 of the heavy chain of HLA-A*11:01, residues 1-99 of β2-microglobulin and the azobenzene-containing peptide, AIM-Z-YPK. There are two molecules in the asymmetric unit. The overall structure of the HLA-A*11:01/β2m/peptide complex is similar to the native peptide complex [PDB code 2HN7], and the RMSD for all Cα atoms of the alpha chain of the MHC molecules is 0.607 Å. The structure of the HLA-A*02:01 complex, which consists of residues 1-275 of the heavy chain, residues 1-100 of β2-microglobulin, and the azobenzene-containing peptide, GLS-Z-RL, was determined to 2.1 Å resolution (Table S5 and Figure S7). There are two molecules in the asymmetric unit. Superimposition of the HLA-A*11:01/β2m/peptide complex with the previously solved structure of HLA-A*02:01 structure [PDB code 3V5H] is similar overall, and the RMSD for all Cα atoms of the alpha chain of the MHC molecules is 1.11 Å.

REFERENCES CITED IN THE MATERIALS AND METHODS SECTION

Blicher, T., J. S. Kastrup, L. O. Pedersen, S. Buus, and M. Gajhede (2006). Structure of HLA-A*1101 in complex with a hepatitis B peptide homologue. *Acta Crystallogr. Sect. F. Struct. Biol. Cryst. Commun.* 62:1179-1184.

Davis, I. W., A. Leaver-Fay, V. B. Chen, J. N. Block, G. J. Kapral, X. Wang, L. W. Murray, W. B. Arendall, J. Snoeyink, J. S. Richardson, et al. (2007). MolProbity: all-atom contacts and structure validation for proteins and nucleic acids. *Nucleic Acids Res.* 35:W375-W383.

Delano, W. L. (2002). The PyMOL Molecular Graphics System, DeLano Scientific LLC. Palo Alto, Calif., USA.

Evans, P. (2006). Scaling and assessment of data quality. *Acta. Crystallogr. D. Biol. Crystallogr.* 62:72-82.

Garboczi, D. N., D. T. Hung, and D. C. Wiley (1992). HLA-A2-peptide complexes: refolding and crystallization of molecules expressed in *Escherichia coli* and complexed with single antigenic peptides. *Proc. Natl. Acad. Sci. U.S.A.* 89:3429-3433.

Kaiser, E., R. L. Colescott, C. D. Bossinger, and P. I. Cook (1970). Color test for detection of free terminal amino groups in the solid-phase synthesis of peptides. *Anal. Biochem.* 34:595-598.

Leslie, W. A. G. (1992). Recent changes to the MOSFLM package for processing film and image plate data. Joint CCP4+ESF-EAMCB News-Letter on Protein Crystallography.

Murshudov, G. N., A. A. Vagin, and E. J. Dodson (1997). Refinement of macromolecular structures by the maximum-likelihood method. *Acta Crystallogr. D. Biol. Crystallogr.* 53:240-255.

Rodenko, B., M. Toebes, S. R. Hadrup, W. J. E. van Esch, A. M. Molenaar, T. N. M. Schumacher, and H. Ovaa (2006). Generation of peptide-MHC class I complexes through UV-mediated ligand exchange. *Nat. Protoc.* 1:1120-1132.

Smart, O. S., T. O. Womack, C. Flensburg, P. Keller, W. Paciorek, A. Sharff, C. Vonrhein, and G. Bricogne (2012). Exploiting structure similarity in refinement: automated NCS and target-structure restraints in BUSTER. *Acta Crystallogr. D. Biol. Crystallogr.* 68:368-380.

Vagin, A., and A. Teplyakov (2000). An approach to multi-copy search in molecular replacement. *Acta Crystallogr. D. Biol. Crystallogr.* 56:1622-1624.

Verhelst, S. H. L., M. Fonović, and M. Bogyo (2007). A mild chemically cleavable linker system for functional proteomic applications. *Angew. Chem. Int. Ed. Engl.* 46:1284-1286.

Results

The application of azobenzene-containing (Abc, Z) linkers that are sensitive to sodium dithionite ($Na_2S_2O_4$) were explored. The recently developed stereocenter-free building block is accessible from readily available starting materials by a straightforward and cost-effective synthesis route. Furthermore, the Abc moiety is unaffected by reducing agents common to biological protocols (e.g., TCEP, DTT) and the correct fragmentation conditions have been demonstrated to be compatible with biomolecules and living systems.[5]

The Abc-linker, with its 12 bond lengths separating the amino- and carboxylic acid functionalities, cannot formally be regarded as tetrapeptide isostere (11 bond lengths, FIG. 1, Panel a), but was envisaged to act as a surrogate for four amino acid residues, making allowances for the double bond and aromatic systems counting toward the peptidomimetic backbone. Conditional ligands were designed such that the Abc building block strategically replaced non-essential residues within a parent epitope of high affinity (Tables S1 and S2), which improves the likelihood of the resulting Abc ligand to bind to and stabilize the recombinant MHC sufficiently during in vitro refolding and purification. For example, in the HLA-A*11:01-restricted epitope from hepatitis B virus DNA polymerase 110-118 (Table S1), the residues at positions P4-P7 are solvent-exposed, identifying them as candidates for Abc replacement.[6] Moreover, the key N- and C-terminal anchor residues Ile (P2) and Lys (P10) were conserved to ultimately furnish the Abc-homologue AIM-Z-YPK (4), which was obtained through standard Fmoc-based solid-phase peptide synthesis (SPPS) (Figure S1). Applying the same strategy, a panel of Abc ligands for HLA-A*11:01, HLA-A*02:01 and H2-Kb were obtained (Table S1, Figure S1); covering allelic variants of MHC predominantly found in Asian and Caucasian populations, as well as in common murine disease models.

To determine whether the Abc-ligands' binding to the MHC product they were designed for was unperturbed by the tetrapeptide isostere, a UV-sensitive complex was used to begin, discharged its peptide cargo by traditional irradiation, and subsequently measured the capability of the Abc-ligand (which is inert to photocleavage) to prevent disintegration of the emptied complex by MHC stability ELISA (FIG. 1, Panel b for HLA-A*11:01, Figure S2 for HLA-A*02:01 and H2-Kb). As the protein requires all subunits to maintain a stable conformation, peptides that rescued the complex were deemed appropriate to produce purified Abc-ligand:MHC molecules (Figure S3). Definitive proof of peptide association, and the molecular details in which the Abc ligand binds the MHC, was furnished by X-ray crystallographic studies. The structure of HLA-A*11:01 in complex with AIM-Z-YPK (4) was determined to 2.43 Å resolution (Table S3, Figure S4). The conditional ligand (FIG. 1, Panel d, cyan) engages the HLA in a way very similar to the parent peptide (FIG. 1, Panel d, yellow) and occupies the peptide-binding groove by preserving crucial hydrogen bonds and salt bridges formed by the parent peptide via its N- and C-terminal anchor residues (Table S4, Figure S5). The central azobenzene moiety protrudes straight from the groove, is solvent exposed, and sufficiently straddles the four amino acids it was designed to replace. Furthermore, it was observed 4 to occupy two alternative confirmations in the crystal (Figure S6). Optimization of the size exclusion protocol demonstrated that the two refolded A*11:01 complexes could be separately obtained (Figures S7a and S7b). These molecular species did not interconvert when left in solution, and had hydrodynamic volumes of 98 Å and 171 Å as judged by dynamic light scattering, that likely correspond to the monomeric and dimeric MHCs, respectively (Figure S7c). A second crystal structure of HLA-A*02:01 binding to GLS-Z-RL (17) at 2.1 Å resolution essentially displays the same features (but in this case, no alternative conformation for the ligand is observed, Tables S5 and S6, Figures S8 and S9).

Figure 2:
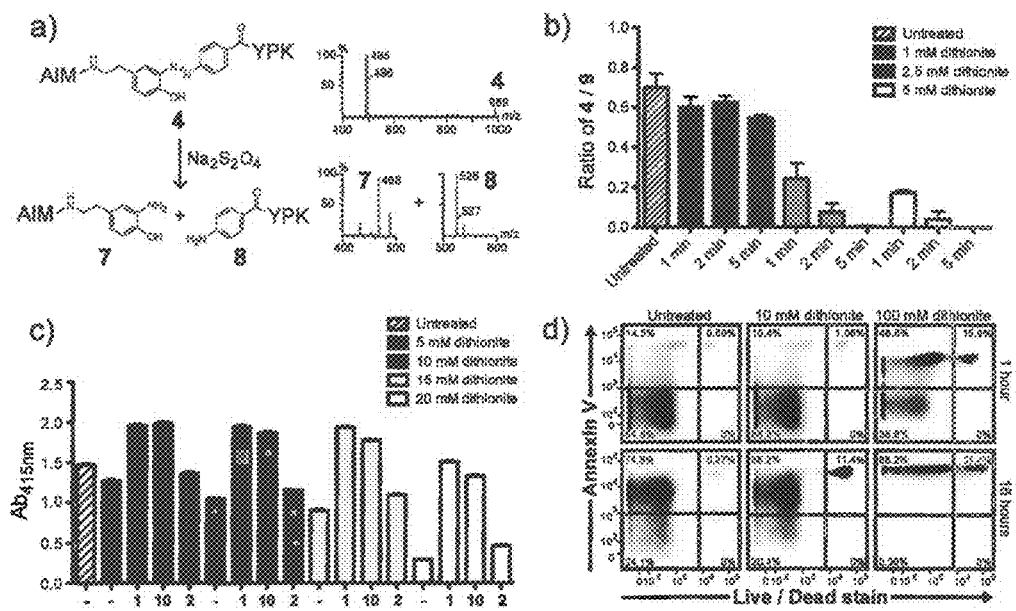
FIG. 2: Cleavage kinetics and conditions of HLA-A*11:01-restricted Abc ligand. Panel a) Cleavage of 4 resulted in two aniline products (7 and 8) upon addition of sodium dithionite. Reaction was confirmed using LC-MS. Panel b) 4 is incubated in the presence of 9 at 1:1 ratio with 1, 2.5 or 5 mM of sodium dithionite and the reactions were quenched after 1, 2 or 5 minutes. The reaction mixtures were analyzed for the presence of intact ABC ligands using LC/MS. Panel c) Refolded A*11:01 molecules bearing 4 were peptide-exchanged were with A*11:01-restricted peptides (1 and 10) and A*02:01-restricted peptide (2) in the presence of 5 to 20 mM sodium dithionite. Controls with no peptides added (−) to the MHC molecules were included. Stable MHC molecules were quantified using MHC stability ELISA. Panel d) Freshly isolated PBMCs were incubated with 10 mM (middle column) and 100 mM (right column) sodium dithionite for 1 hour (top row) or 16 hours (bottom row) to assess cellular toxicity of sodium dithionite. Cells were stained with anti-CD8 antibodies, Annexin V and LIVE/DEAD® viability dye, and analyzed on flow cytometry. Plots shown were gated on $CD8^+$ cells. Numbers in each plot are cells expressed as a percentage of total $CD8^+$ population.

Next, it was examined how to facilitate rapid and complete Abc-peptide exchange. Exposure of 4 to dithionite indeed resulted in fragmentation toward the expected two aniline products 7 and 8 as confirmed by LC/MS (FIG. 2, Panel a). By mixing in a stable internal standard 9 at 1:1 ratio, and interrupting the reaction (ranging from of 1 to 5 mM of sodium dithionite) by solid phase extraction, the kinetics could be tracked by LC/MS analysis (FIG. 2, Panel b). An incubation period of 5 minutes with 2.5 mM Na2S2O4 (aq) was sufficient for the original Abc ligand to fall below the limit of detection, indicative of (near) quantitative peptide cleavage in solution.

The peptide exchange efficiency (spanning 5 to 20 mM dithionite) was analyzed by ELISA on purified Abc-ligand: MHC complexes with established T-cell epitopes (Table S2). Reduction-promoted peptide exchange could be observed at all tested dithionite concentrations (FIG. 2, Panel c, for A*11:01, Figure S10 for A*02:01, and Kb). Disulfide bonds remain intact under these conditions (Figure S11) and the method, therefore, appears to have limited effect on the overall stability of the protein complexes. For HLA-A*11:01, the highest signal-to-background ratio was obtained at 20 mM Na2S2O4, yet this trend was the reverse for HLA-A*02:01, highlighting that every allelic variant carrying a tailored Abc ligand will have unique stability characteristics.

A further impetus for moderating the amount of employed reducing agent is to prevent toxicity toward cells. It would be preferable that the MHC tetramers of novel specificity can be directly deployed, which involves them being shortly (<1 hour) incubated with CD8+ T-cells, without requiring the removal of any component (i.e., employed reagents or side-product) that could unnecessarily lengthen or complicate the peptide exchange and/or staining protocol. Both primary and cultured cells of various origins, fortunately, were very tolerant to buffered dithionite, showing little sign of apoptosis or cell death at high (10 mM) concentration and prolonged (16 hours) exposure (FIG. 2, Panel d, Figure S12). Balancing the above constraints, 10 mM Na2S2O4 (aq) were employed in the ensuing experiments.

Figure 3:
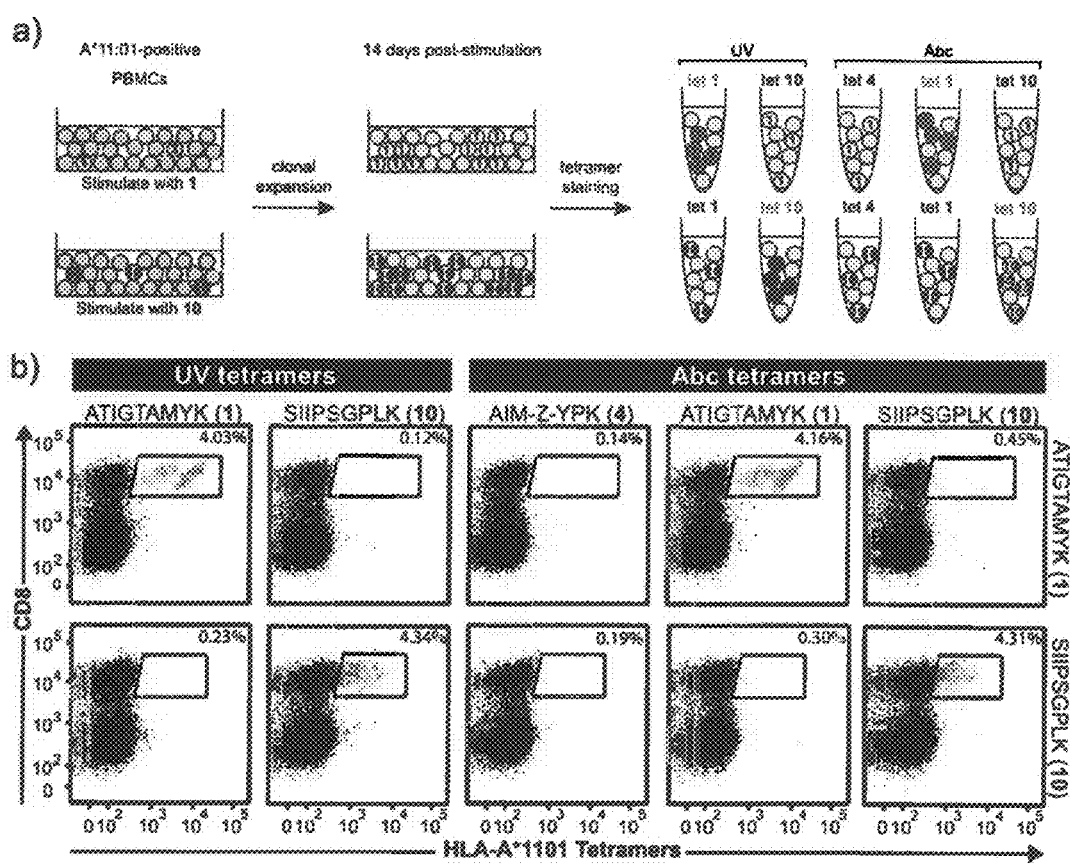
FIG. 3: Detection of antigen-specific $CD8^+$ T-cells using A*11:01 MHC tetramers generated from UV-mediated peptide exchange or sodium dithionite-mediated peptide exchange. Panel a) Schematic diagram of experimental workflow. Freshly isolated PBMCs from an A*11:01-positive volunteer were stimulated with A*11:01-restricted epitopes EBV $BRLF1_{134-142}$ (1, upper row) and Influenza A $MP_{13-21}$ (10, lower row) and clonally expanded for 14 days. Antigen-specific $CD8^+$ T-cells were then labeled with cognate peptide-bound A*11:01 MHC tetramers (red) and detected via flow cytometry. Panel b) A*11:01-EBV $BRLF1_{134-142}$ (columns 1 and 4), A*11:01-Influenza A $MP_{13-21}$ (columns 2 and 5) and A*11:01-Abc (column 3) tetramers were incubated with the PBMCs to detect EBV $BRLF1_{134-142}$ (1, upper row) and Influenza A $MP_{13-21}$ (10, lower row)-specific $CD8^+$ T-cells 14 days post-stimulation. Number in each plot represents tetramer-positive cells as a percentage of total $CD8^+$ cell population. Plots in columns 1 to 2 and columns 3 to 5 are tetramer staining performed using UV-derived and Abc-derived tetramers, respectively.

To confirm that this strategy enables detection of antigen-specific cells from peripheral blood, a short-term expanded T-cell line from an A*11:01-carrying donor responsive to Epstein Barr Virus (EBV) antigen (BRLF1134-142, 1, FIG. 3 top row) was labeled with MHC tetramers before and after replacement with the canonical epitope (1), and an irrelevant peptide (10). This established that MHC tetramers generated through chemical- or UV-mediated exchange were equally capable in detecting frequencies of CD8+ T-cells (i.e., 4.16% and 4.03%, respectively) only of the correct specificity and with minimal background. This could be replicated in an alternative CD8+ T-cell line reactive toward Influenza A M113-21 peptide (10) when presented by A*11:01 (FIG. 3, bottom row), and reductive exchange of Abc ligands was comparably successful for human HLA-A*02:01 and murine H2-Kb tetramers (Figures S13 and S14, respectively).

Figure 4:
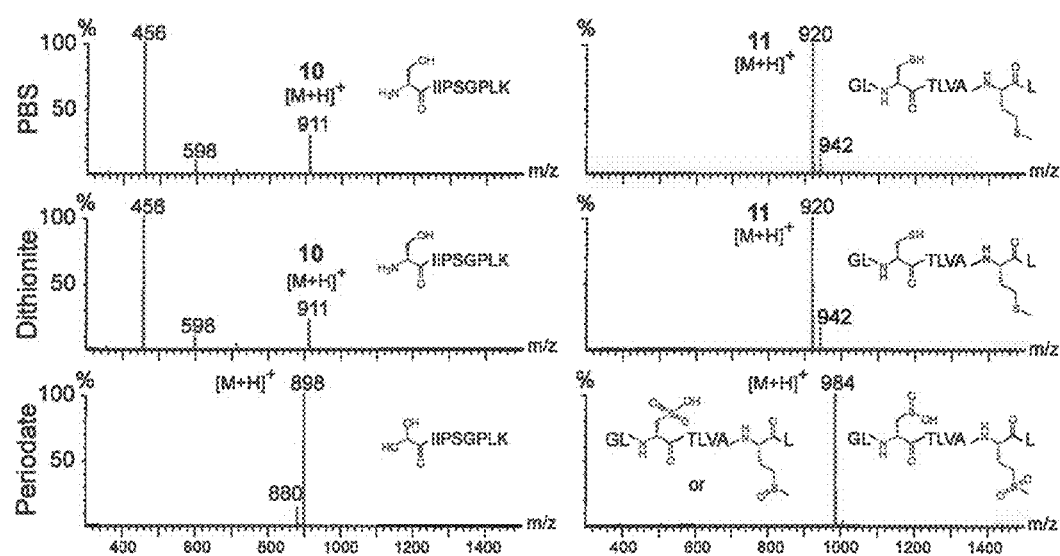
FIG. 4: Effects of reductive and oxidative cleavage conditions on epitopes of interest. Mass spectrometry analysis of peptides Influenza A $MP_{13-21}$ (10, left column) and EBV $BMLF-1_{259-267}$ (11, right column) after incubation with PBS, 10 mM sodium dithionite or 0.3 mM sodium periodate. 10 and 11 remained unmodified when incubated in PBS or 10 mM sodium dithionite. The N-terminal serine of 10 was cleaved when incubated in 0.3 mM sodium periodate. Incubation with 0.3 mM sodium periodate resulted in oxidation of cysteine and methionine residues of 11. Unmodified and modified residues are shown in blue and red, respectively.
Figure 20:
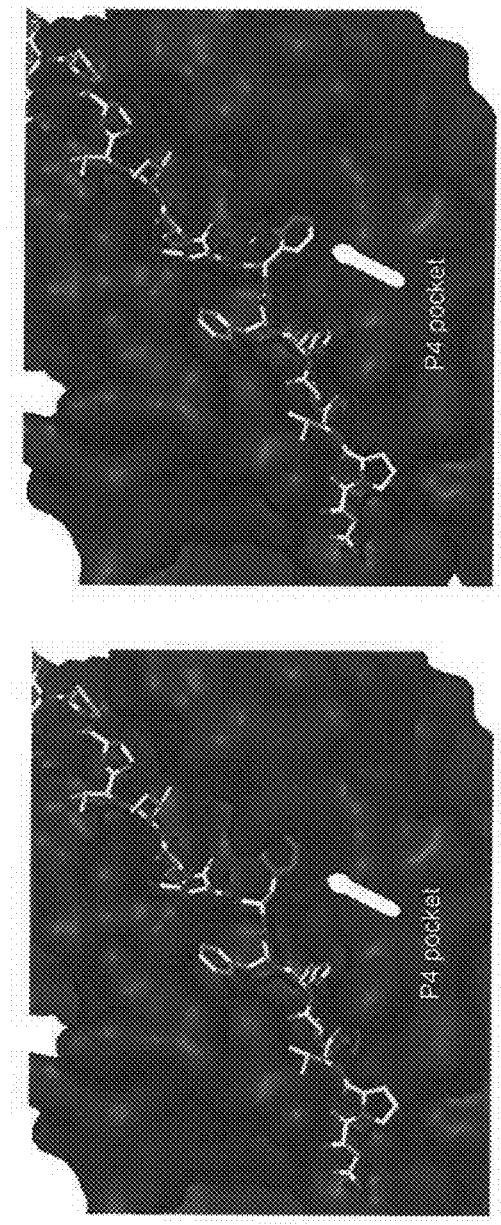
FIG. 20: Crystal structure (left) versus model (right) of the HLA-DR2-$MBP_{85-99}$ complex. $MBP_{85-99}$ (yellow) binds to HLA-DR2 (blue) with the Anp residue at P4 position occupying the large hydrophobic P4 pocket of the MHC molecule. (Grotenbreg et al., *J. Biol. Chem.* 2007, 282: 21425-21436.) This figure is not part of the manuscript.
Figure 23:
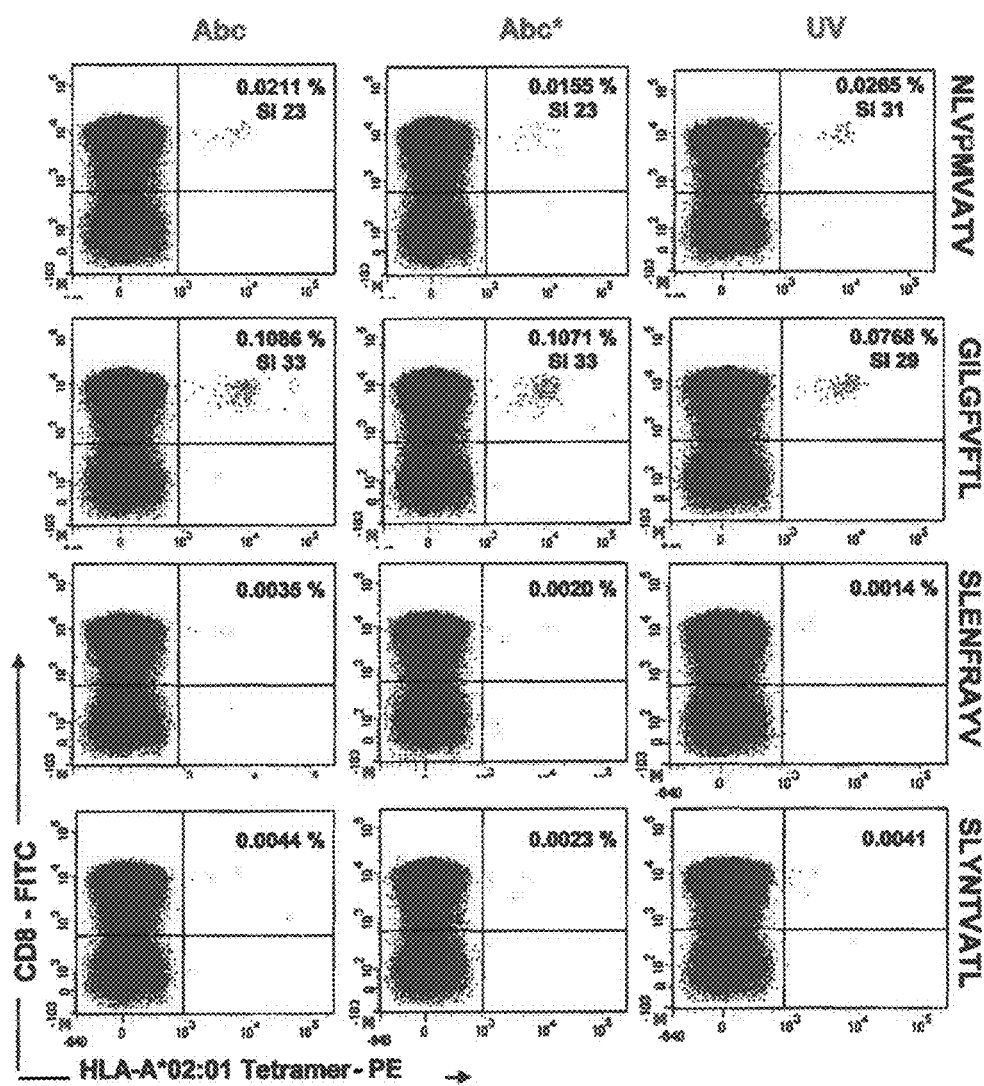
FIG. 23: Human peripheral blood cells (PBMC) were stained for the presence of antigen-specific T-cell responses using PE-labeled tetramers. The flow cytometric results are depicted in the figure. The Abc and UV tetramers render similar results. Staining of antigen-specific T-cell responses against four different CD8 epitopes restricted to HLA-A*02:01 in a PBMC sample. Abc: PE-labeled tetramers generated using Abc ligand peptide exchange technology; HLA-A*02:01-ILKZGV. Abc*: PE-labeled tetramers generated using Abc ligand peptide exchange technology; HLA-A*02:01-ILKZKV. UV: PE-labeled tetramers generated using UV-induced peptide exchange technology; HLA-A*02:01-KILGFVFJV. SI: Stain Index.

Next to preserving protein integrity, it is vital that cleavage conditions do not alter any functionality on the replacement epitope either. Such modifications could pose problems when they occur on critical residues that anchor the peptide to the MHC or are important for T-cell receptor engagement, possibly resulting in failure to identify a given T-cell population. A major limitation, for example, of vicinal diol- or alkanolamine-containing amino acids that can be cleaved by periodate, is that e concomitant oxidation of the Cys-, Met-, N-terminal Ser- or Thr-residues can be oxidized.[7] Therefore, reductive (i.e., 10 mM dithionite) was compared with oxidative (i.e., 0.3 mM periodate) cleavage conditions on well-established T-cell epitopes containing the residues. Incubation with periodate predictably cleaved the N-terminal Ser of A*11:01-restricted Influenza A MP13-21 epitope (10), and (partially) oxidized the Cys and Met of EBV BMLF1-259-267 epitope (11), whereas dithionite treatment left the epitopes unaffected (FIG. 4).

Collectively, a truly bio-orthogonal and robust strategy was established for conditional peptide exchange based on a unique panel of chemolabile Abc ligands that can provide functional libraries of T-cell labeling reagents, both for human MHC molecules frequently found in both Asian and Caucasian populations, as well as for murine MHC. The true value of the method lies in the facile epitope replacement without the need for dedicated UV-irradiation equipment under conditions that are neither detrimental to the protein, the epitope, nor to the cells. Broad population coverage, through the inclusion of diverse MHC allelic variants, is currently under development, as it is believed this will allow widespread application of this high-throughput method with which the sprawling diversity of biologically relevant T-cell populations in both basic research and clinical settings can be tackled.

Alternate Conformations of the Abc Ligand in the HLA-A*11:01 Complex

Electron density was also observed, suggesting that the Abc ligand has an alternate conformation that is non-canonical to peptide-HLA binding; the C-terminal portion of the Abc ligand proceeding from the azobenzene group "flips out" and binds the adjacent molecule in the asymmetric unit, forming what appears to be a "cross-link" that would allow the two MHC molecules to dimerize (Figure S6). The occupancies of the canonical and non-canonical conformation were estimated to be 36% and 64%, respectively. This was calculated based on their expected average B-factor values.

TABLE S1

Sequences of synthesized Abc ligands

| Peptide no. | Abc ligand | Restriction | Sequence | Parent epitope Organism | Protein | Location | IEDB ID |
|---|---|---|---|---|---|---|---|
| 3 | AIF-Z-TK | A*11:01 | AIFQSSMTK | Human immunodeficiency virus 1 | Reverse transcriptase | 158 to 166 | 1913 |
| 4 | AIM-Z-YPK | A*11:01 | IMPARFYPK | Hepatitis B virus | DNA polymerase (peptide homologue) | 110 to 118 | 27530 (2024) |
| 5 | QVPL-Z-YK | A*11:01 | QVPLRPMTYK | Human immunodeficiency virus 1 | Nef protein | 73 to 82 | 52760 |

TABLE S1-continued

Sequences of synthesized Abc ligands

| Peptide no. | Abc ligand | Restriction | Sequence | Parent epitope | | | |
|---|---|---|---|---|---|---|---|
| | | | | Organism | Protein | Location | IEDB ID |
| 6 | KTF-Z-PK | A*11:01 | KTFPPTEPK | SARS coronavirus | Nucleoprotein | 362 to 370 | 33667 |
| 13 | FLPS-Z-SV | A*02:01 | FLPSDFFPSV | Hepatitis B virus | Core protein | 18 to 27 | 16833 |
| 14 | LLF-Z-YV | A*02:01 | LLFGYPVYV | Human T-lymphotropic virus 1 | Transcriptional activator Tax | 11 to 19 | 37257 |
| 15 | NLVP-Z-TV | A*02:01 | NLVPMVATV | Human herpesvirus 5 | 65 kDa lower matrix phosphoprotein | 485 to 493 | 44920 |
| 16 | NLVP-Z-VATV | A*02:01 | NLVPMVATV | Human herpesvirus 5 | 65 kDa lower matrix phosphoprotein | 485 to 493 | 44920 |
| 17 | GLS-Z-RL | A*02:01 | GLSRYVARL | Hepatitis B virus | Polymerase | 412 to 420 | 21145 |
| 19 | FAP-Z-AL | $K^b$ and $D^b$ | FAPGNYPAL | Sendai virus | Nucleoprotein | 324 to 332 | 15248 |
| 20 | FAP-Z-KL | $K^b$ and $D^b$ | FAPGNYPAL | Sendai virus | Nucleoprotein | 324 to 332 | 15248 |

Table S1: Alternate conformations of the Abc (Z) in the HLA-A*11:01 complex. Electron density was also observed, suggesting that the Abc ligand has an alternate conformation that is non-canonical to peptide-HLA binding; the C-terminal portion of the Abc ligand proceeding from the azobenzene group "flips out" and binds the adjacent molecule in the asymmetric unit, forming what appears to be a "cross-link" that would allow the two MHC molecules to dimerize (Figure S6). The occupancies of the canonical and non-canonical conformation were estimated to be 36% and 64%, respectively. This was calculated based on their expected average B-factor values. The design of Abc ligands is based on the following parent epitopes. The restriction element, sequence, organism and protein source of the parent epitopes are listed. Residues in these epitopes that are replaced by the Abc moiety are underlined. IEDB ID refers to the epitope identification number in the immune epitope database and analysis resource (URL: http://www.immuneepitope.org/).

TABLE S2

Sequences of antigenic peptides

| Peptide no. | Sequence | Restriction | Organism | Protein | Location | IEDB ID |
|---|---|---|---|---|---|---|
| 1 | ATIGTAMYK | A*11:01 | Human herpesvirus 4 | Transcription activator BRLF1 | 134 to 142 | 5002 |
| 2 | FLPSDFFPSV | A*02:01 | Hepatitis B virus | Core protein | 18 to 27 | 16833 |
| 10 | SIIPSGPLK | A*11:01 | Influenza A virus | Matrix protein 1 | 13 to 21 | 58567 |
| 11 | GLCTLVAML | A*02:01 | Human herpesvirus 4 | BMLF1 protein | 259 to 267 | 20788 |
| 12 | CLGGLLTMV | A*02:01 | Human herpesvirus 4 | Latent membrane protein 2 | 426 to 434 | 6568 |
| 21 | NLVPMVATV | A*02:01 | Human herpesvirus 5 | 65 kDa lower matrix phosphoprotein | 485 to 493 | 44920 |
| 18 | SIINFEKL | $K^b$ | Gallus gallus | Ovalbumin | 258 to 265 | 58560 |
| 22 | SVLAFRRL | $K^b$ | Toxoplasma gondii | Tgd057 | 57 to 64 | 146017 |
| 9 | IPAAAGRFF | $L^d$ | Toxoplasma gondii | Rhoptry protein ROP7 | 435 to 443 | 103992 |

Table S2: Previously identified antigenic peptides that were used in this study for MHC stability ELISA and generation of peptide-specific MHC tetramers are listed. IEDB ID refers to the epitope identification number in the immune epitope database and analysis resource (URL: http://www.immuneepitope.org/).

TABLE S3

Data collection and refinement statistics of HLA-A*11:01:AIM-Z-YPK

Data collection

| | |
|---|---|
| Name | HLA-A*11:01:AIM-Z-YPK |
| Beamline | Rigaku |
| Detector | R-AXIS IV++ |
| Space group | P1 |
| Cell dimensions | |
| a, b, c (Å) | 52.14, 71.46, 75.43 |
| α, β, γ (°) | 106.74, 96.74, 105.28 |
| Resolution (Å) | 29.93-2.43 (2.494-2.431)* |
| $R_{merge}$ (%) | 5.2 (17) |
| I/σ (I) | 17.4 (6.8) |
| Completeness (%) | 94.7 (90.7) |
| Redundancy | 4 (4) |

Refinement

| | |
|---|---|
| Resolution (Å) | 29.93-2.43 (2.49-2.43)* |
| Number of reflections | 33278 (2260) |
| $R_{work}/R_{free}$ | 0.18/0.25 |
| Number of atoms | |
| Protein | 6252 |
| Ligand | 79 |
| Water | 249 |
| B-factors (Å$^2$) | |
| Protein | 30.30 |
| Ligand | 23.73 |
| Water | 27.67 |
| RMSD values | |
| Bond lengths (Å) | 0.014 |
| Bond angles (°) | 1.693 |
| Ramachandran values | |
| Most favoured (%) | 96.3 |
| Additional allowed (%) | 3.7 |
| Disallowed (%) | 0.0 |

*Values for the highest resolution shell are shown

TABLE S4

Interactions between AIM-Z-YPK and HLA-A*11:01

| Abc-Peptide | | HLA | | Distance | Van der Waals |
|---|---|---|---|---|---|
| Residue | Atom | Residue | Atom | (Å) | interactions |
| Ala1 | N | Tyr7 | OH | 3.2 | Met5, Tyr7, Glu63, |
| | N | Tyr171 | OH | 2.9 | Tyr195, Arg163, Trp167, |
| | O | Tyr159 | OH | 2.6 | Tyr171 |
| Ile2 | N | Glu63 | Oε1 | 2.8 | Tyr7, Tyr9, Met45, Glu63, Asn66, Val67, Tyr99, Tyr159, Arg163 |
| Met3 | N | Tyr99 | OH | 3.2 | Asn66, Tyr99, Arg114, Tyr159 |
| Tyr8 | O | Trp147 | Nε1 | 2.9 | Ala152 |
| Pro9 | | | | | Asp77 |
| Lys10 | N | Asp77 | Oδ1 | 3.0 | Asp77, Thr80, Tyr84, Asp116, Thr143, Lys146 |
| | OXT | Tyr84 | OH | 2.7 | |
| | OXT | Thr143 | Oγ1 | 3.0 | |
| | O | Lys146 | Nζ | 3.0 | |
| | Nζ | Asp116 | Oδ2 | 2.8 | |

H-bond cut off < 3.5 Å, Van der Waals: 3.6-4.0

TABLE S5

Data collection and refinement statistics of HLA-A*02:01:GLS-Z-RL

Data collection

| | |
|---|---|
| Name | HLA-A*02:01:GLS-Z-RL |
| Beamline | Swiss Light Source X06DA |
| Detector | Pilatus |
| Space group | $P2_1$ |
| Cell dimensions | |
| a, b, c (Å) | 57.79, 79.58, 83.97 |
| α, β, γ (°) | 90, 89.96, 90 |
| Resolution (Å) | 28.89-2.10 (2.21-2.10)* |
| $R_{merge}$ (%) | 4.6 (9.4) |
| I/σ (I) | 14.0 (7.9) |
| Completeness (%) | 92.3 (81.3) |
| Redundancy | 2 (1.7) |

Refinement

| | |
|---|---|
| Resolution (Å) | 28.89-2.10 (2.21-2.10) |
| Number of reflections | 43603 (2861) |
| $R_{work}/R_{free}$ | 0.18/0.22 |
| Number of atoms | |
| Protein | 6217 |
| Ligand | 681 |
| Water | 537 |
| B-factors (Å$^2$) | |
| Protein | 16.73 |
| Ligand | 16.59 |
| Water | 23.58 |
| RMSD values | |
| Bond lengths (Å) | 0.010 |
| Bond angles (°) | 1.04 |
| Ramachandran values | |
| Most favoured (%) | 98.4 |
| Additional allowed (%) | 1.6 |
| Disallowed (%) | 0.00 |

*Values for the highest resolution shell are shown

TABLE S6

Interactions between GLS-Z-RL and HLA-A*02:01

| Abc-Peptide | | HLA | | Distance | Van der Waals |
|---|---|---|---|---|---|
| Residue | Atom | Residue | Atom | (Å) | interactions |
| Gly1 | N | Tyr7 | OH | 2.6 | Met5, Tyr7, Glu63, |
| | N | Tyr171 | OH | 2.8 | Tyr159, Trp167, |
| | O | Tyr159 | OH | 2.7 | |
| Leu2 | O | Lys66 | Nζ | 2.9 | Tyr7, Glu63, Lys66, Val67, Tyr99, His70, Tyr159 |
| Ser3 | Oγ | Tyr99 | OH | 2.9 | Lys66, His70, Tyr99, Tyr159 |
| | N | Tyr99 | OH | 2.9 | |
| Abc | O1 | Tyr116 | OH | 3.5 | |
| Arg8 | O | Trp147 | Nε1 | 2.8 | Asp77, Leu81, Tyr116, Tyr123, Thr143, Trp147 |
| Leu9 | N | Asp77 | Oδ1 | 3.1 | |
| | OXT | Tyr84 | OH | 2.8 | |
| | OXT | Thr143 | Oγ1 | 2.7 | |

H-bond cut off < 3.5 Å, Van der Waals: 3.6-4.0

TABLE S7

| Common human MHC Class II molecules | Frequency of allele[a] | Crystal structure (PDB ID#)[b] | Parent ligand[c] | Design of three Abc ligands[e] | Reference (PubMed ID)[e] |
|---|---|---|---|---|---|
| HLA-DR1 (DRA, DRB1*01:01) | 5% | 2IAM | GELIGILNAAKVPAD | GELI-Abc-AAKVPAD<br>GELIGI-Abc-KVPAD<br>GELIGIL-Abc-VPAD | 17334368 |
| HLA-DR2 (DRA, DRB1*1501) | 13% | 1YMM | ENPVVHFFKNIVTPR | ENPVV-Abc-NIVTPR<br>ENPVVH-Abc-IVTPR<br>ENPVVHFF-Abc-TPR | 15821740 |
| HLA-DR4 (DRA, DRB1*04:01) | 17% | 3O6F | FSWGAEGQRPGFG | FSW-Abc-QRPGFG<br>FSWG-Abc-RPGFG<br>FSWGAE-Abc-GFG | 21297580 |
| HLA-DP2 (DPA1*01:03, DPB1*02:01) | 4%, 6% | 3LQZ | RKFHYLPFLST | RKF-Abc-FLPST<br>RKFH-Abc-LPST<br>RKFHYL-Abc-ST | 20356827 |
| HLA-DQ8 (DQA1*03:01, DQB1*03:02) | 23%, 43% | 4GG6 | QQYPSGQGSFQPSQQNPQ | QQYPSGQ-Abc-PSQQNPQ<br>QQYPSGQG-Abc-SQQNPQ<br>QQYPSGQGSF-Abc-QNPQ | 23063329 |

| Common mouse MHC Class II molecule | | Crystal structure (PDB ID#)[b] | Parent ligand | Design of three Abc ligands[c] | Reference (PubMed ID)[d] |
|---|---|---|---|---|---|
| H-2-IAb | N/A | 3C5Z | FEAQKAKANKAVD | FEA-Abc-ANKAVD<br>FEAQK-Abc-KAVD<br>FEAQKA-Abc-AVD | 18308592 |
| H-2-IAd | — | 1IAO | ISQAVHAAHAEINEAGR | IS-Abc-AAHAEINEAGR<br>ISQA-Abc-HAEINEAGR<br>ISQAV-Abc-AEINEAGR | 9529149 |
| H-2-IEk | — | 1KT2 | ADLIAYLKQATK | ADLI-Abc-QATK<br>ADLIA-Abc-ATK<br>ADLIAYL-Abc-K | 11956295 |

[a] On the World Wide Web at ncbi.nlm.nih.gov/projects/gv/mhc/ihwg.cgi?cmd=PRJOV&ID=9
[b] On the World Wide Web at rcsb.org./pdb/home/home.do
[c] P1, P4, P6 and P9 anchor residues are indicated by bold and underlined format.
[d] Structural design of Abc conditional ligands, MHC binding and fragmentation is achieved if the Abc moiety is incorporated between the critical P1 and P9 anchors, and replaces 4 amino acid residues.
[e] On the World Wide Web at ncbi.nlm.nih.gov/pubmed.

CITED ART

[1] a) E. M. Sletten, C. R. Bertozzi, *Angew. Chem. Int. Ed. Engl.* 2009, 48:6974-6998; b) M. Grammel, H. C. Hang, *Nat. Chem. Biol.* 2013, 9:475-484.

[2] a) G. Leriche, L. Chisholm, A. Wagner, *Bioorg. Med. Chem.* 2012, 20:571-582; b) G. C. Rudolf, W. Heydenreuter, S. A. Sieber, *Curr. Opin. Chem. Biol.* 2013, 17:110-117.

[3] a) J. D. Altman, P. A. H. Moss, P. J. R. Goulder, D. H. Barouch, M. G. McHeyzer-Williams, J. I. Bell, A. J. McMichael, M. M. Davis, *Science* 1996, 274:94-96; b) M. M. Davis, J. D. Altman, E. W. Newell, *Nat. Rev. Immunol.* 2011, 11:551-558.

[4] a) M. Toebes, M. Coccoris, A. Bins, B. Rodenko, R. Gomez, N. J. Nieuwkoop, W. van de Kasteele, G. F. Rimmelzwaan, J. B. A. G. Haanen, H. Ovaa, et al., *Nat. Med.* 2006, 12:246-251; b) G. M. Grotenbreg, M. J. Nicholson, K. D. Fowler, K. Wilbuer, L. Octavio, M. Yang, A. K. Chakraborty, H. L. Ploegh, K. W. Wucherpfennig, *J. Biol. Chem.* 2007, 282:21425-21436; c) A. H. Bakker, R. Hoppes, C. Linnemann, M. Toebes, B. Rodenko, C. R. Berkers, S. R. Hadrup, W. J. E. van Esch, M. H. M. Heemskerk, H. Ovaa, et al., *Proc. Natl. Acad. Sci. U.S.A.* 2008, 105:3825-3830; d) G. M. Grotenbreg, N. R. Roan, E. Guillen, R. Meijers, J.-H. Wang, G. W. Bell, M. N. Starnbach, H. L. Ploegh, *Proc. Natl. Acad. Sci. U.S.A.* 2008, 105:3831-3836; e) E.-M. Frickel, N. Sahoo, J. Hopp, M.-J. Gubbels, M. P. J. Craver, L. J. Knoll, H. L. Ploegh, G. M. Grotenbreg, *J Infect. Dis.* 2008, 198:1625-1633; f) S. Gredmark-Russ, E. J. Cheung, M. K. Isaacson, H. L. Ploegh, G. M. Grotenbreg, *Journal of Virology* 2008, 82:12205-12212; g) C. X. L. Chang, A. T. Tan, M. Y. Or, K. Y. Toh, P. Y. Lim, A. S. E. Chia, T. M. Froesig, K. D. Nadua, H.-L. J. Oh, H. N. Leong, et al., *Eur. J. Immunol.* 2013, 43:1109-1120.

[5] a) S. H. L. Verhelst, M. Fonović, M. Bogyo, *Angew. Chem. Int. Ed. Engl.* 2007, 46:1284-1286; b) Y.-Y. Yang, M. Grammel, A. S. Raghavan, G. Charron, H. C. Hang, *Chemistry & Biology* 2010, 17:1212-1222; c) F. Landi, C. M. Johansson, D. J. Campopiano, A. N. Hulme, *Org. Biolmol. Chem.* 2010, 8:56-59; d) G. Budin, M. Moune-Dimala, G. Leriche, J.-M. Saliou, J. Papillon, S. Sanglier-Cianférani, A. Van Dorsselaer, V. Lamour, L. Brino, A. Wagner, *Chembiochem.* 2010, 11:2359-2361; e) G. Leriche, G. Budin, L. Brino, A. Wagner, *Eur. J. Org. Chem.* 2010, 4360-4364.

[6] a) J. Sidney, H. M. Grey, S. Southwood, E. Celis, P. A. Wentworth, M. F. del Guercio, R. T. Kubo, R. W. Chesnut, A. Sette, *Hum. Immunol.* 1996, 45:79-93; b) T. Blicher, J. S. Kastrup, L. Ø. Pedersen, S. Buus, M. Gajhede, *Acta Crystallogr. Sect. F Struct. Biol. Cryst. Commun.* 2006, 62:1179-1184.

[7] a) B. Rodenko, M. Toebes, P. H. N. Celie, A. Perrakis, T. N. M. Schumacher, H. Ovaa, *J. Am. Chem. Soc.* 2009, 131:12305-12313; b) A. Amore, K. Wals, E. Koekoek, R. Hoppes, M. Toebes, T. N. M. Schumacher, B. Rodenko, H. Ovaa, *Chembiochem.* 2013, 14:123-131.

The invention claimed is:

1. A major histocompatibility complex (MHC) molecule comprising a ligand in the peptide binding groove of the MHC molecule, where the ligand comprises an azobenzene (Abc), comprising the general Formula II:

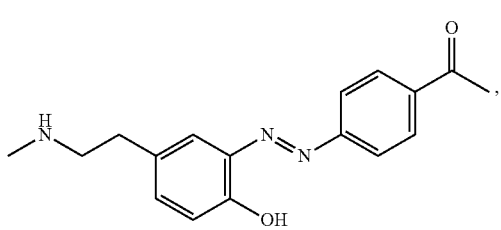

Formula II and wherein the azobenzene is connected to at least two amino acid residues separated by the azo-group of the Abc, wherein the amino acid residues are known to interact with the peptide binding groove of the MHC molecule.

2. The MHC molecule according to claim 1, wherein said ligand is an MHC peptide antigen of which amino acid residues that are located between the amino acid residues have been replaced by an Abc.

3. The MHC molecule according to claim 1, wherein the ligand comprises the general formula III

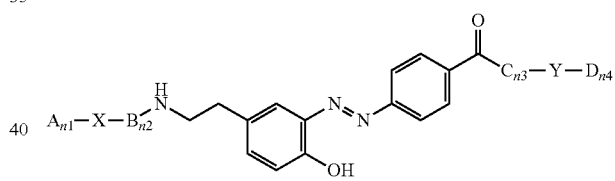

Formula III wherein,
A, B, C, D, X and Y are each independently an amino acid residue;
$n_1$, $n_2$, $n_3$ and $n_4$ are each independently 0-11; and
$n_1+n_2+n_3+n_4$ equals 2-18.

4. The MHC molecule according to claim 1, wherein said Abc is a trans-Abc.

5. The MHC molecule according to claim 3, wherein $n_2$ or $n_3$ or both are 1.

6. A complex comprising at least two MHC molecules according to claim 1.

7. A composition comprising an MHC molecule according to claim 1, and an MHC peptide antigen.

8. A method of producing an MHC molecule, the method comprising:
providing an MHC molecule and an azobenzene-containing MHC ligand, and incubating the MHC molecule with the azobenzene-containing MHC ligand under MHC folding or refolding conditions, thereby producing the MHC molecule according to claim 1;
contacting the produced MHC molecule with a reducing agent; and
contacting said MHC molecule with an MHC peptide antigen.

9. A method of detecting an MHC molecule comprising producing an MHC molecule according to the method of claim 8, and detecting the MHC molecule.

10. A method according to claim 9, wherein the MHC molecule, a peptide in the peptide binding groove of the MHC molecule, or both, comprise a label.

11. A solid surface comprising an MHC molecule according to claim 1.

12. An azobenzene of formula III

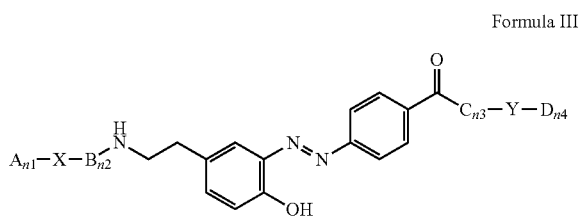

Formula III wherein,
A, B, C, D, X and Y are each independently an amino acid residue;
$n_1$, $n_2$, $n_3$ and $n_4$ are each independently 0-11; and
$n_1+n_2+n_3+n_4$ equals 2-18.

13. A method of using the azobenzene of claim 12, the method comprising:
producing an MHC molecule comprising a peptide in the MHC molecule's peptide binding groove with the azobenzene, wherein producing the MHC molecule comprises: providing an MHC molecule and an azobenzene-containing MHC ligand, and incubating the MHC molecule with the azobenzene-containing MHC ligand under MHC folding or refolding conditions, thereby producing the MHC molecule comprising a peptide in the MHC molecule's peptide binding groove with the azobenzene:
contacting the thus produced MHC molecule with a reducing agent; and
contacting the MHC molecule with an MHC peptide antigen.

* * * * *